US011932871B2

(12) United States Patent
Geiger et al.

(10) Patent No.: US 11,932,871 B2
(45) Date of Patent: Mar. 19, 2024

(54) METHODS OF CULTURING T CELLS AND USES OF SAME

(71) Applicants: Yeda Research and Development Co. Ltd., Rehovot (IL); The Medical Research, Infrastructure and Health Services Fund of the Tel Aviv Medical Center, Tel-Aviv (IL)

(72) Inventors: Benjamin Geiger, Rehovot (IL); Nir Friedman, Rehovot (IL); Shimrit Lieber, Rehovot (IL); Zelig Eshhar, Rehovot (IL); Tova Waks, Rehovot (IL); Anat Globerson Levin, Rehovot (IL)

(73) Assignees: YEDA RESEARCH AND DEVELOPMENT CO. LTD., Rehovot (IL); THE MEDICAL RESEARCH, INFRASTRUCTURE AND HEALTH SERVICES FUND OF THE TEL AVIV MEDICAL CENTER, Tel-Aviv (IL)

( * ) Notice: Subject to any disclaimer, the term of this patent is extended or adjusted under 35 U.S.C. 154(b) by 540 days.

(21) Appl. No.: 16/490,568

(22) PCT Filed: Mar. 2, 2018

(86) PCT No.: PCT/IL2018/050236
§ 371 (c)(1),
(2) Date: Sep. 2, 2019

(87) PCT Pub. No.: WO2018/158775
PCT Pub. Date: Sep. 7, 2018

(65) Prior Publication Data
US 2020/0071669 A1    Mar. 5, 2020

(30) Foreign Application Priority Data

Mar. 2, 2017 (IL) .......................................... 250916

(51) Int. Cl.
*C12N 5/0783* (2010.01)
*A61K 35/17* (2015.01)

(52) U.S. Cl.
CPC ............ *C12N 5/0636* (2013.01); *A61K 35/17* (2013.01); *C12N 2501/21* (2013.01); *C12N 2501/2306* (2013.01); *C12N 2501/515* (2013.01); *C12N 2501/58* (2013.01); *C12N 2502/1121* (2013.01); *C12N 2510/00* (2013.01)

(58) Field of Classification Search
None
See application file for complete search history.

(56) References Cited

U.S. PATENT DOCUMENTS

| 5,731,160 A | 3/1998 | Melief et al. | |
|---|---|---|---|
| 7,745,140 B2 | 6/2010 | June et al. | |
| 8,012,750 B2* | 9/2011 | Har-Noy | C12N 5/0636 435/372.3 |
| 2002/0119568 A1* | 8/2002 | Berenson | C07K 16/289 435/372 |
| 2015/0030619 A1* | 1/2015 | Milone | C12N 5/0636 435/375 |

FOREIGN PATENT DOCUMENTS

| WO | WO 2008/108794 | 9/2008 | |
|---|---|---|---|
| WO | WO 2014/048920 | 4/2014 | |
| WO | WO-2016019300 A1 * | 2/2016 | ........... A61K 31/436 |
| WO | WO 2018/158775 | 9/2018 | |
| WO | WO 2018/158775 A9 | 9/2018 | |

OTHER PUBLICATIONS

Flanagan et al., 2004, Cell. Immunol. vol. 231: 75-84.*
Castellana, 2006, Surface Scientific Reports, vol. 61: 429-444.*
International Search Report and the Written Opinion dated May 17, 2018 From the International Searching Authority Re. Application No. PCT/IL2018/050236. (20 Pages).
Office Action and Search Report dated Oct. 19, 2017 From the Israel Patent Office Re. Application No. 250916. (10 Pages).
Adutler-Lieber et al. "Engineering of Synthetic Cellular Microenvironments: Implications for Immunity", Journal of Autoimmunity, 54: 100-111, Available Online Jun. 18, 2014.
Adutler-Lieber et al. "Substrate-Bound CCL21 and ICAM1 Combined With Soluble IL-6 Collectively Augment the Expansion of Antigen-Specific Murine CD4+ T Cells", Blood Advances, XP055471974, 1(15): 1016-1030, Jun. 27, 2017.
Bromley et al. "Stimulation of Naive T-Cell Adhesion and Immunological Synapse Fromation by Chemokine-Dependent and -Independent Mechanisms", Immunology, XP055472900, 106(3): 289-298, Jul. 2002.
Deeths et al. "ICAM-1 and B7-1 Provide Similar But Distinct Costimulation for CD8+ T Cells, While CD4+ T Cells Are Poorly Costimulated by ICAM-1", European Journal of Immunology, 29(1): 45-53, Jan. 1999.
Doh et al. "Immunological Synapse Arrays: Patterned Protein Surfaces That Modulate Immunological Synapse Structure Formation in T Cells", Proc. Natl. Acad. Sci. USA, PNAS, XP055472387, 103(15): 5700-5705 Apr. 11, 2006.

(Continued)

*Primary Examiner* — Amy E Juedes
(74) *Attorney, Agent, or Firm* — Mark S. Cohen; PEARL COHEN ZEDEK LATZER BARATZ LLP

(57) ABSTRACT

Methods of culturing T cells are provided. Accordingly there is provided a method of culturing T cells comprising culturing T cells in the presence of a T cell stimulator, an exogenous CCL21 and an exogenous ICAM1, thereby culturing the T cells. Also provided are cell cultures, isolated T cells and uses of same.

10 Claims, 32 Drawing Sheets
(30 of 32 Drawing Sheet(s) Filed in Color)
Specification includes a Sequence Listing.

(56) References Cited

OTHER PUBLICATIONS

Friedman et al. "Surface-Bound Chemokines Capture and Prime T Cells for Synapse Formation", Nature Immunology, XP055472830, 7(10): 1101-1108, Published Online Sep. 10, 2006.

Maude et al. "Chimeric Antigen Receptor T Cells for Sustained Remissions in Leukemia", The New England Journal of Medicine, 371(16): 1507-1517, Oct. 16, 2014.

Redeker et al. "Improving Adoptive T Cell Therapy: The Particular Role of T Cell Costimulation, Cytokines, and Post-Transfer Vaccination", Frontiers in Immunology, XP055459807, 7(Art.345): 1-18, Sep. 6, 2018.

Tedla et al. "Phenotypic and Functional Characterization of Lymphocytes Derived From Normal and HIV-1-Infected Human Lymph Nodes", Clinical and Experimental Immunology, 117(1): 92-99, Jul. 1999.

Woolf et al. "Lymph Node Chemokines Promote Sustained T Lymphocyte Motility Without Triggering Stable Integrin Adhesiveness in the Absende of Shear Forces", Nature Immunology, 8(10: 1076-1085, Published Online Aug. 26, 2007.

Communication Pursuant to Article 94(3) EPC dated Apr. 19, 2021 From the European Patent Office Re. Application No. 18712421.9. (7 Pages).

\* cited by examiner

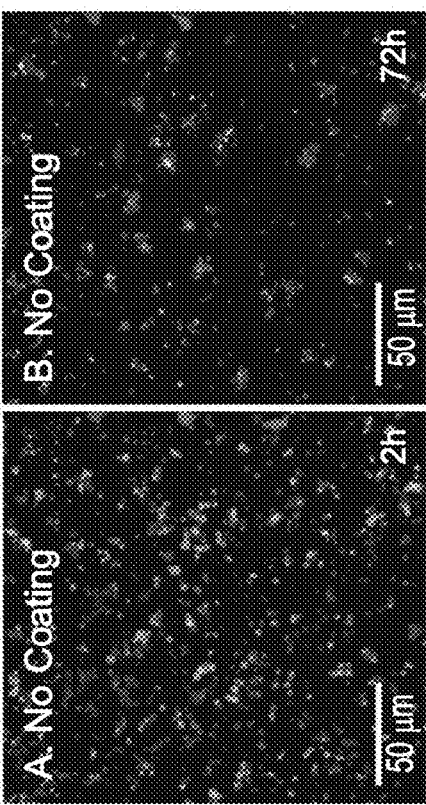
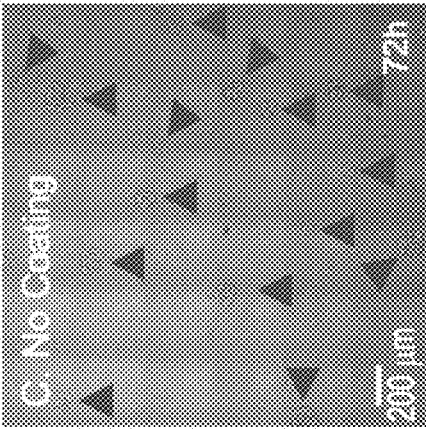
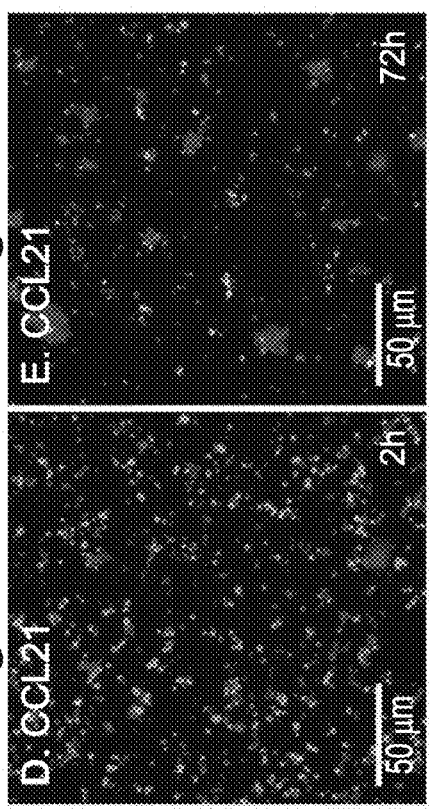
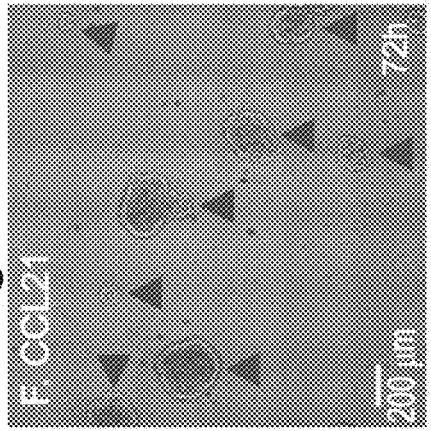

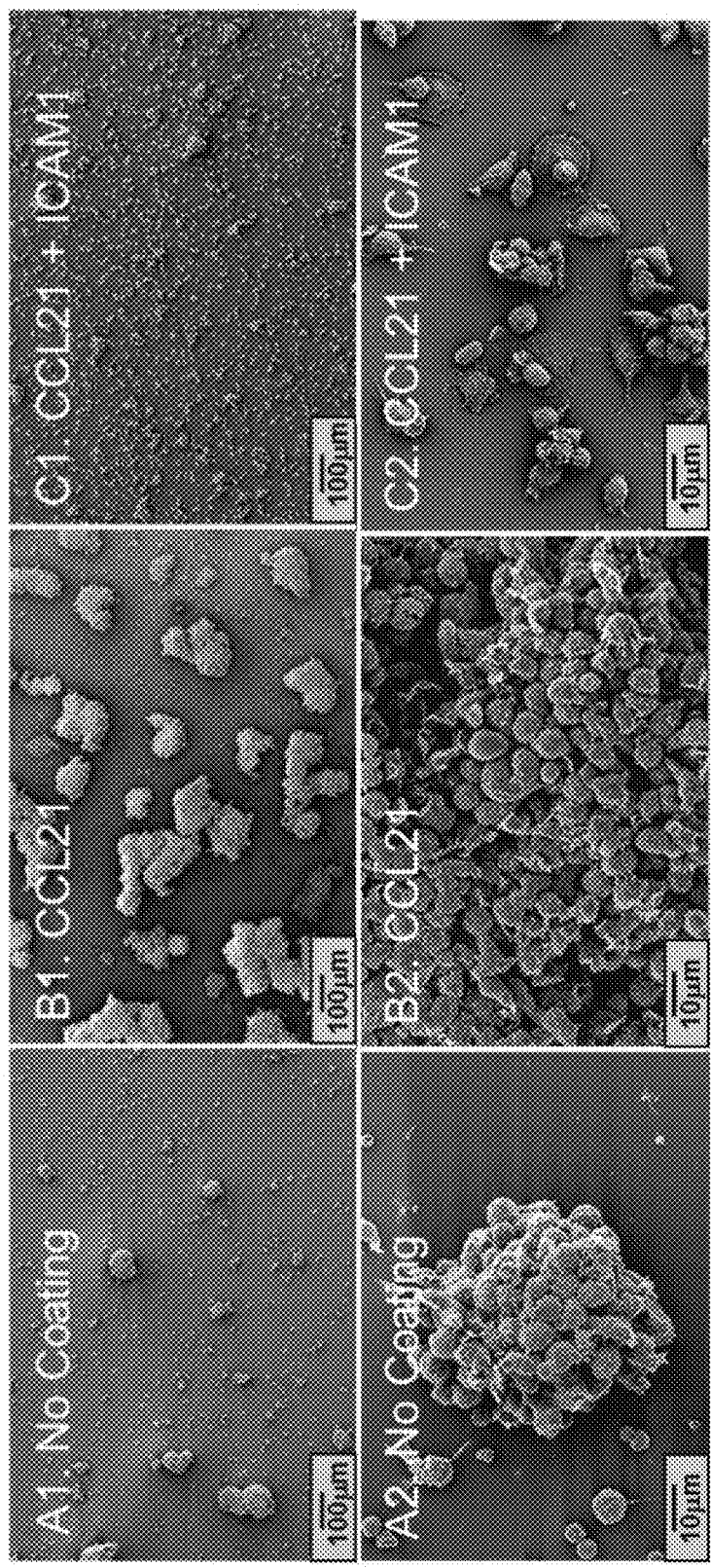

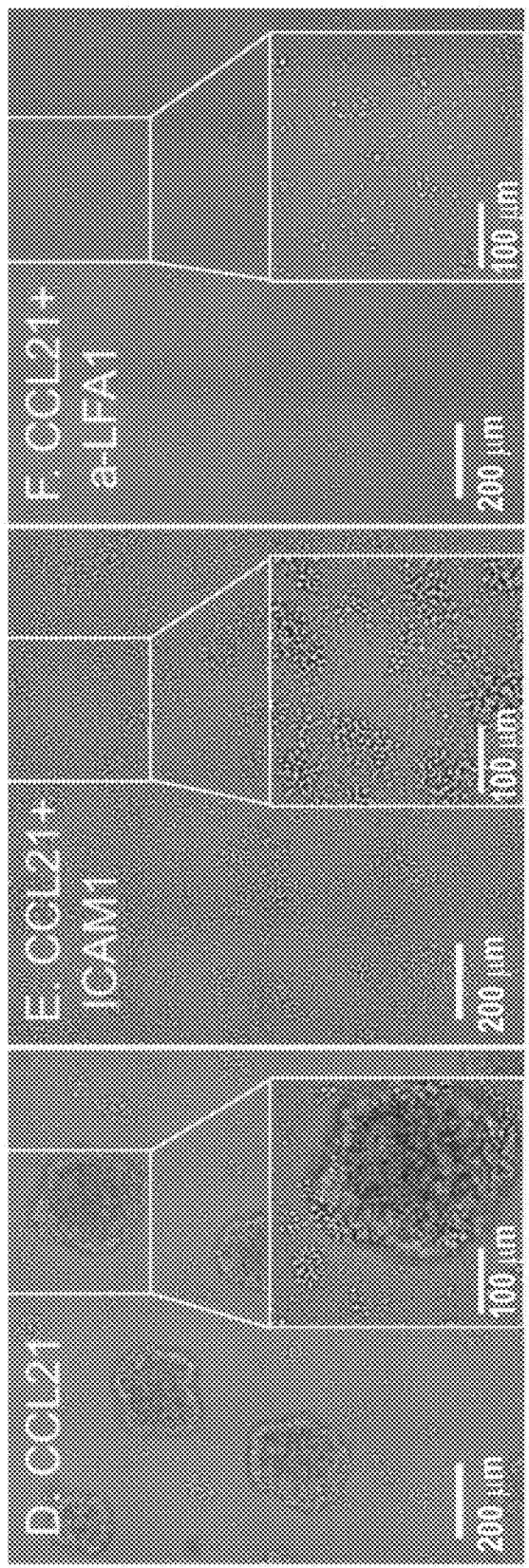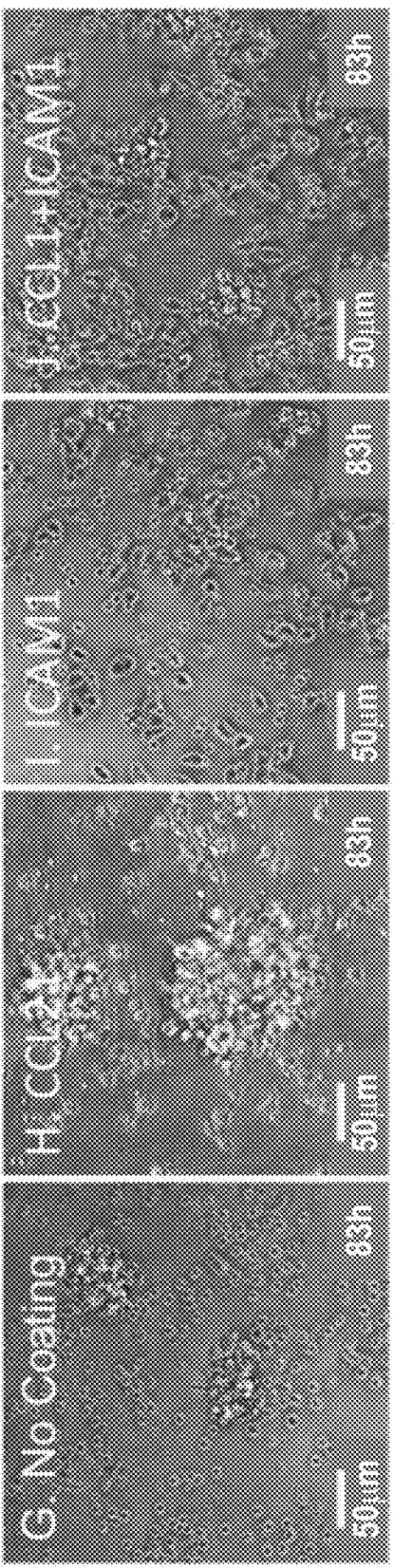

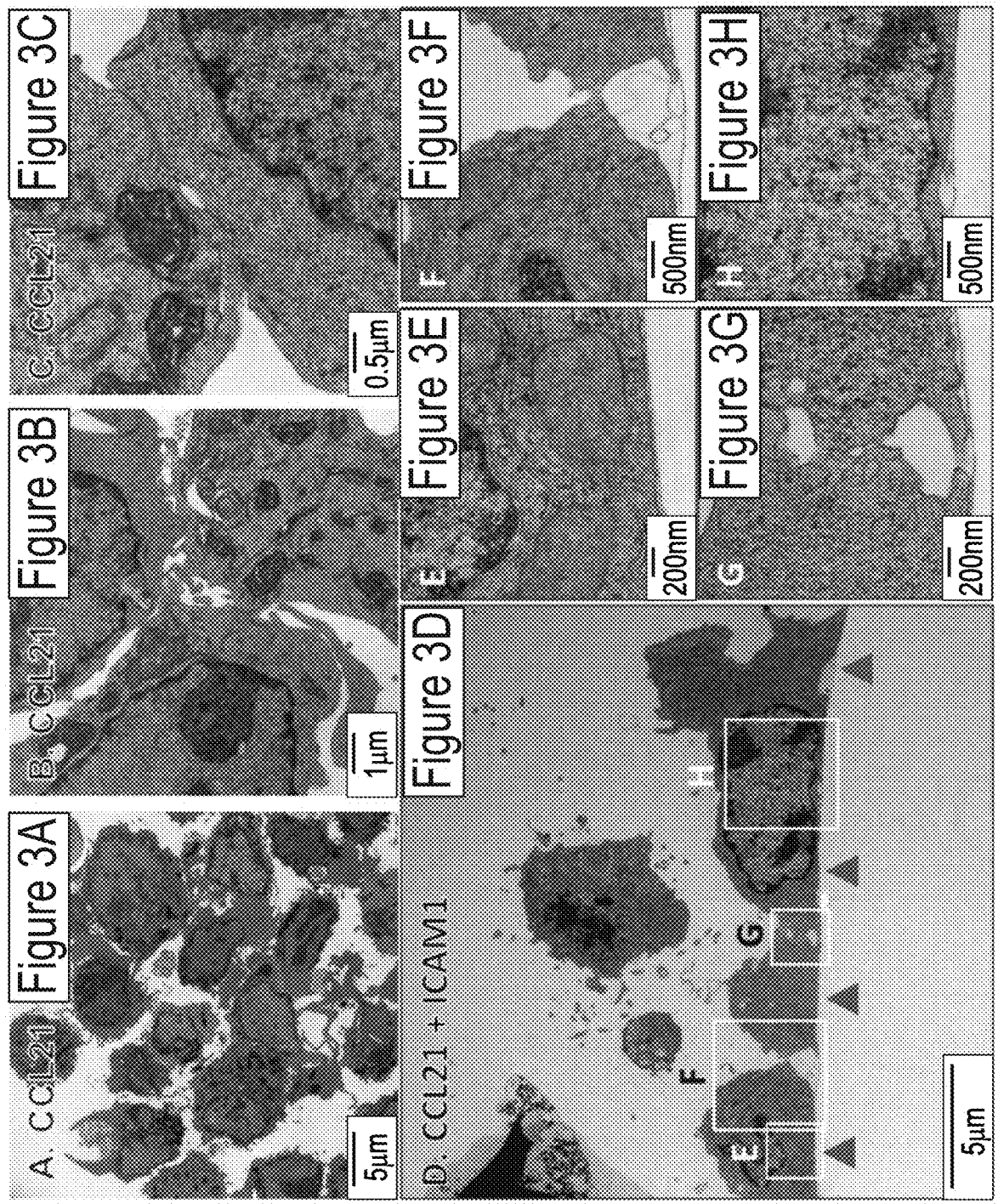

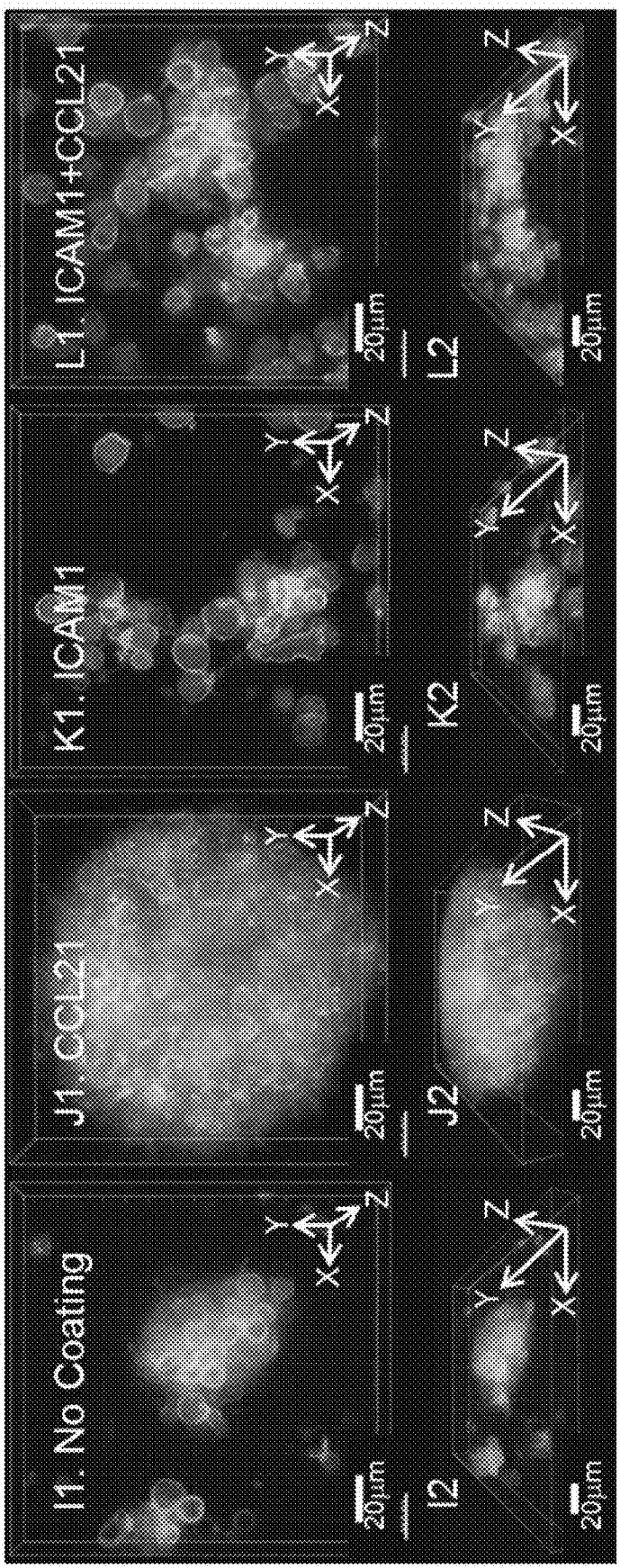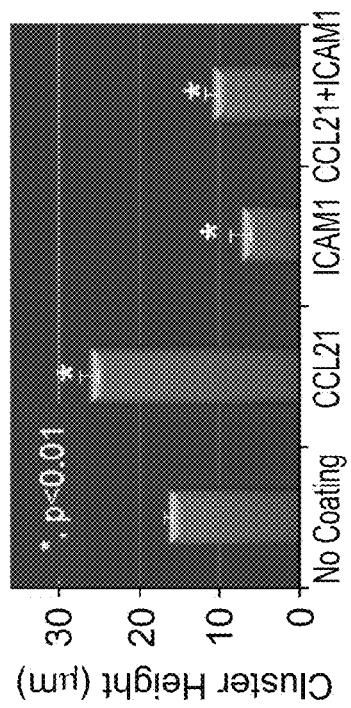

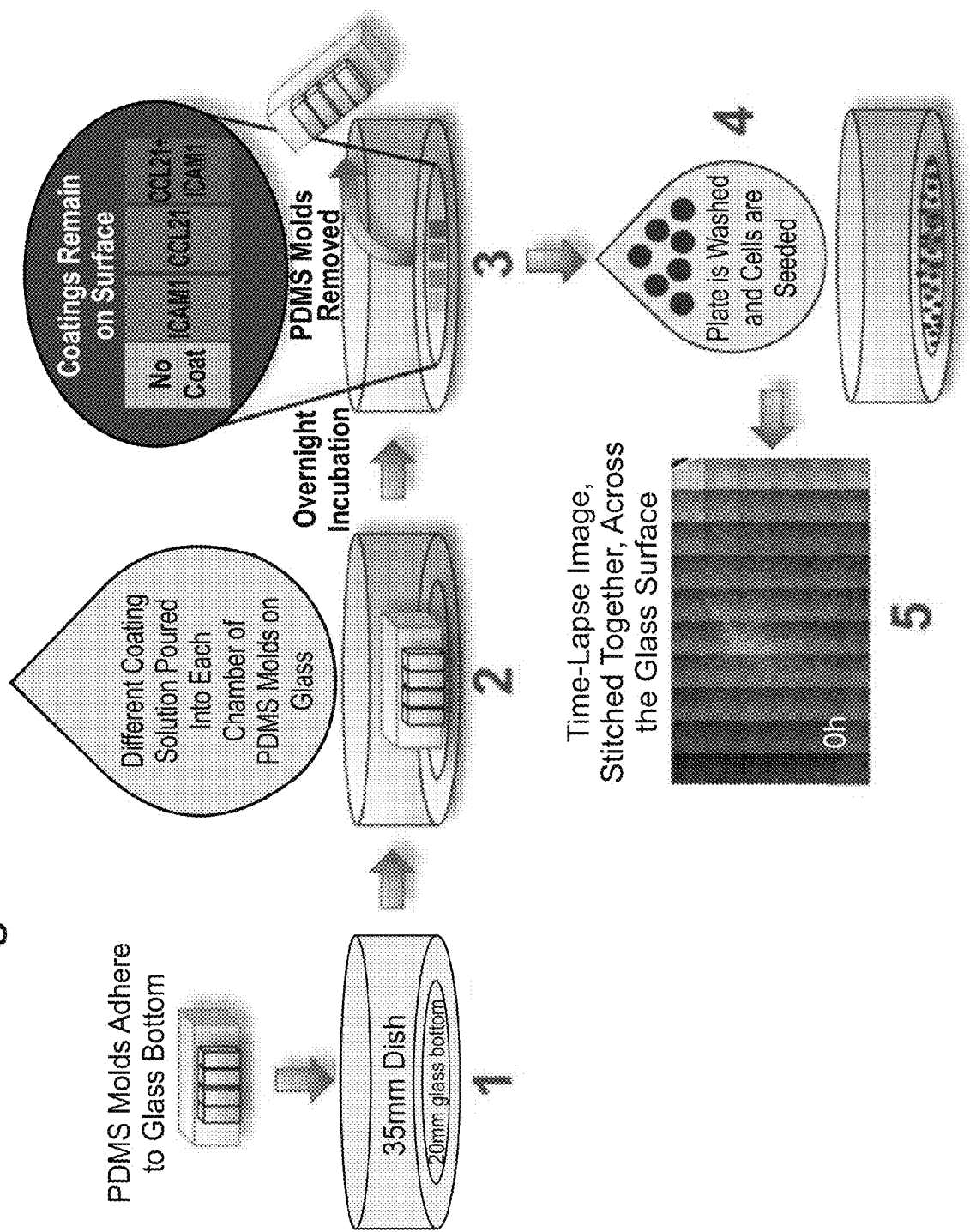

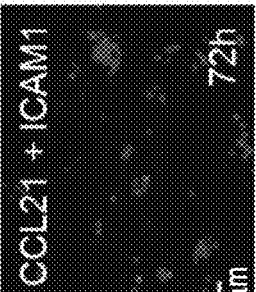
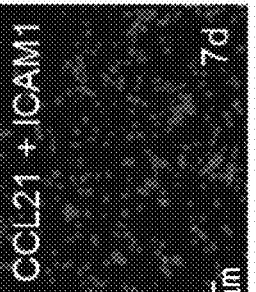
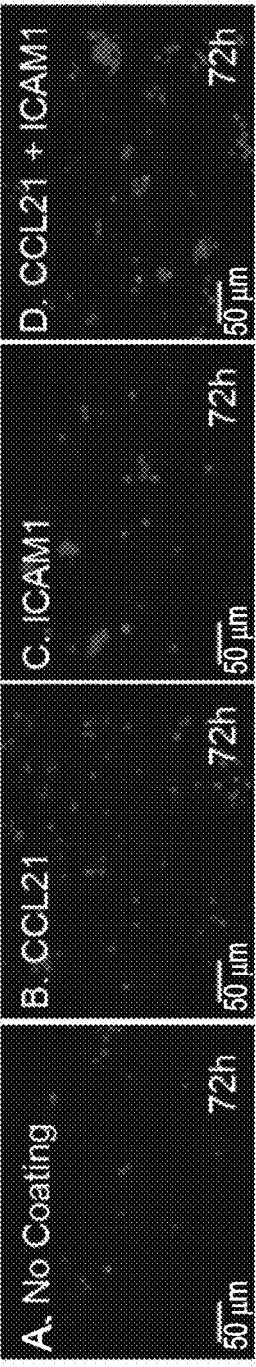
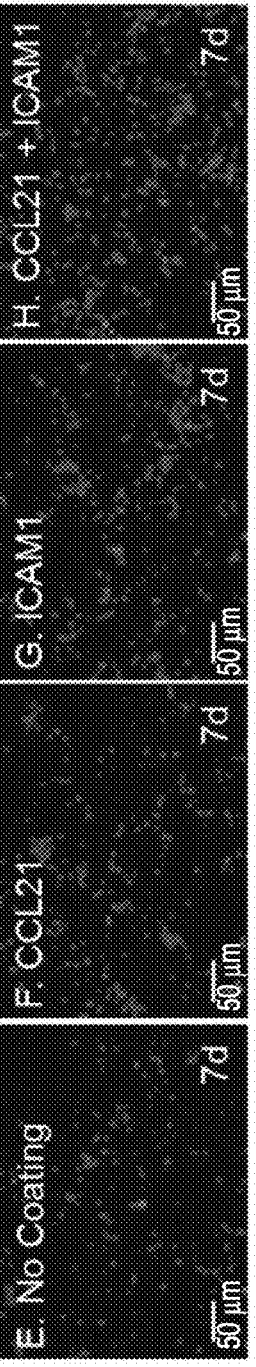
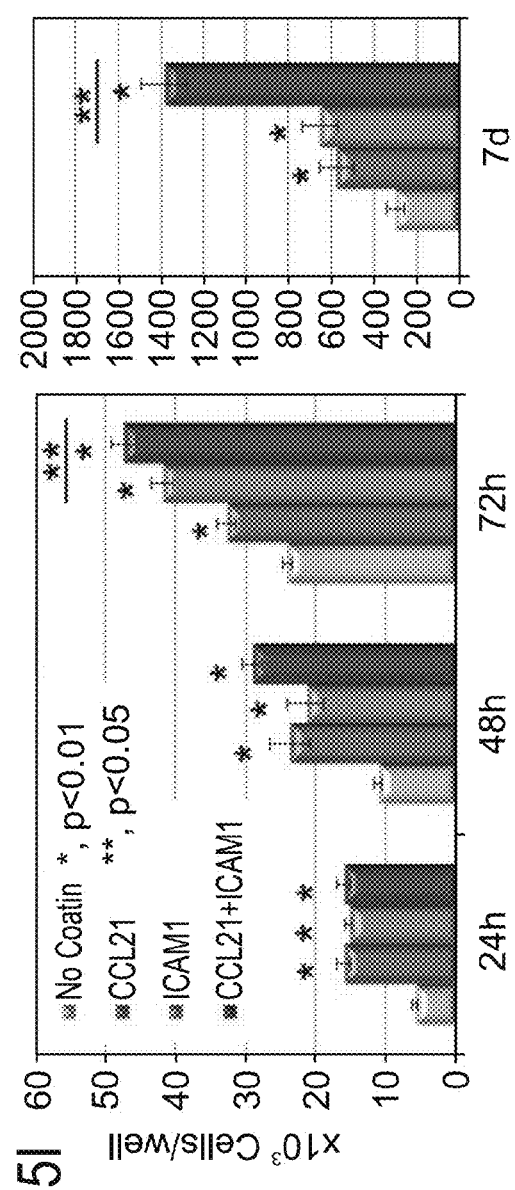

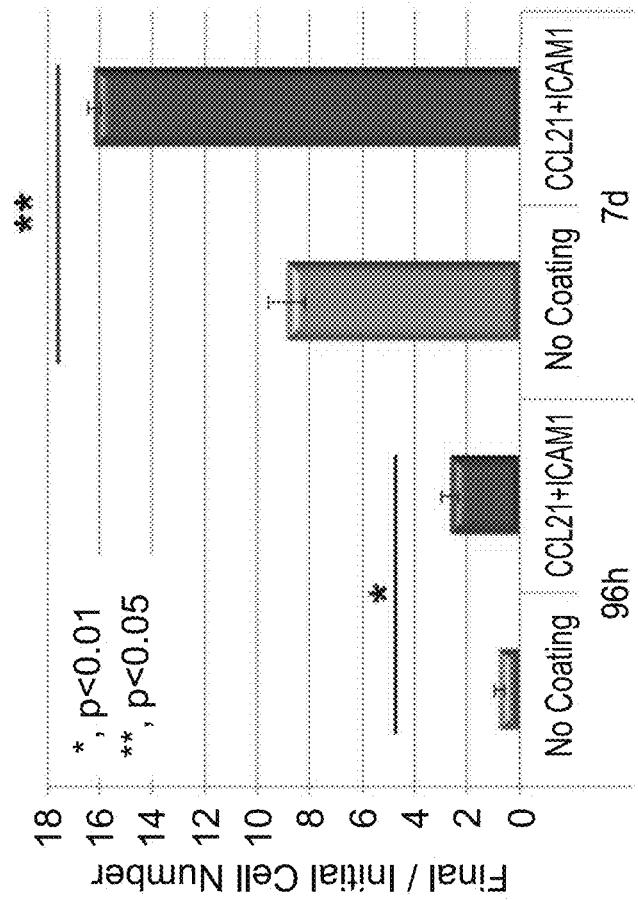
Figure 5L
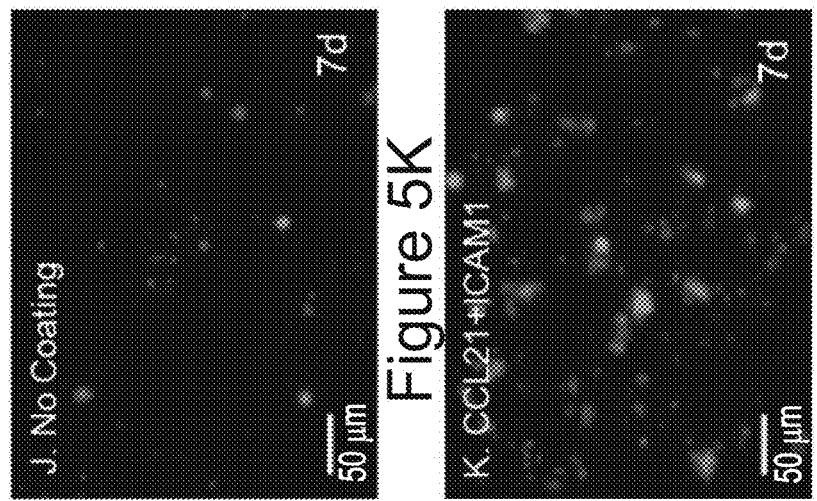
Figure 5J
Figure 5K

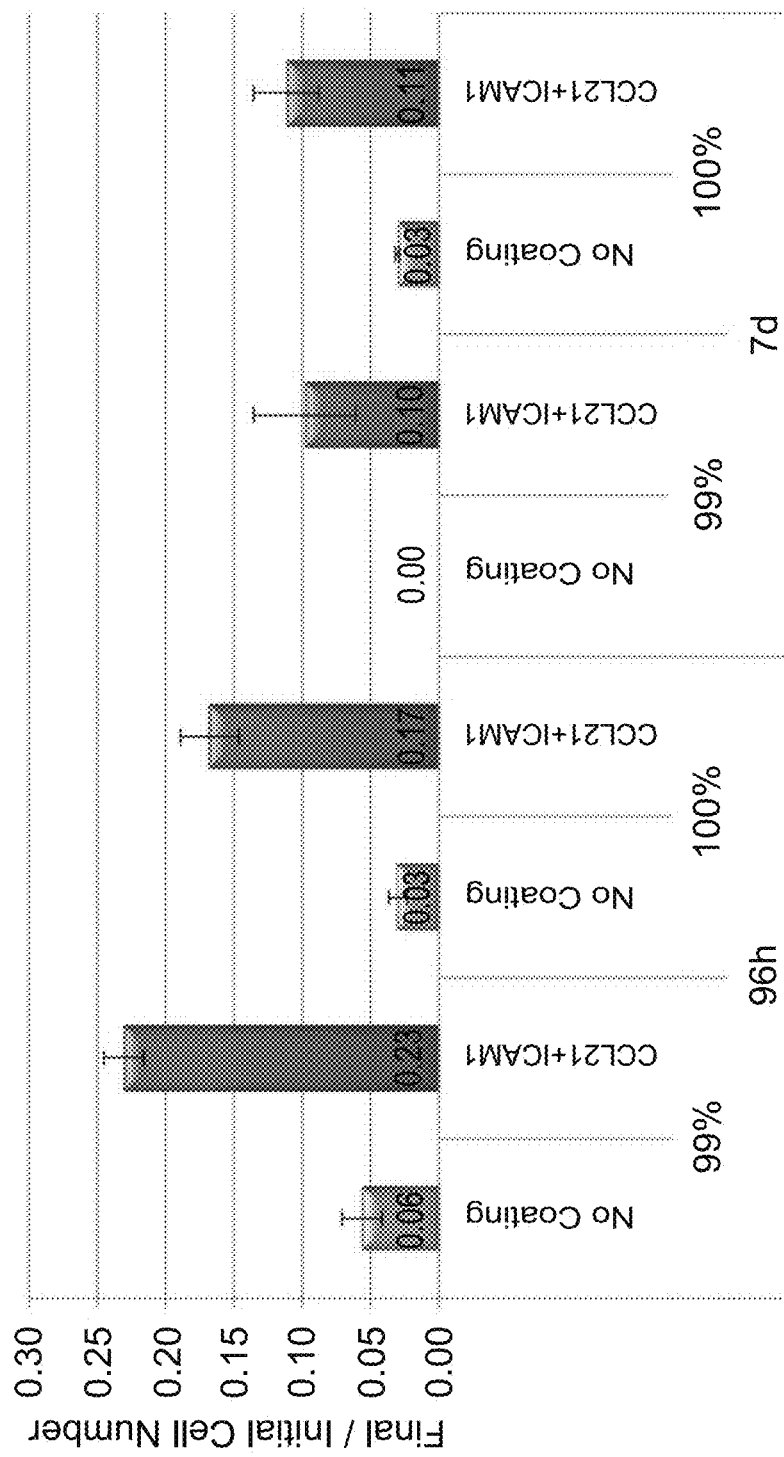

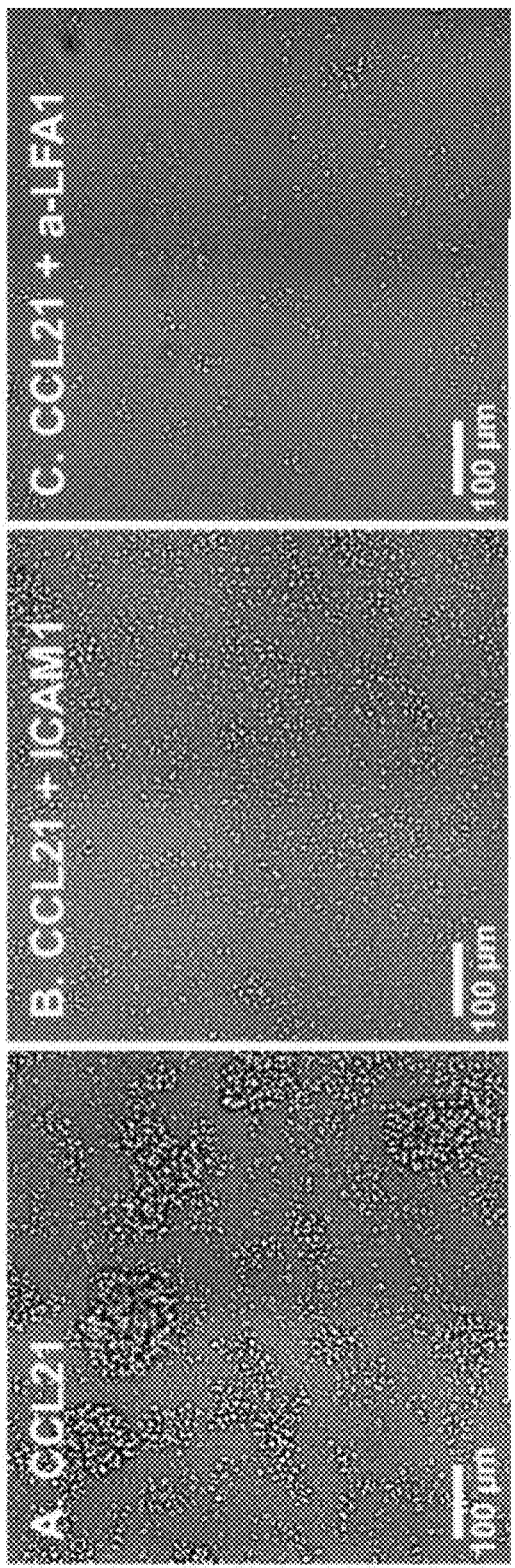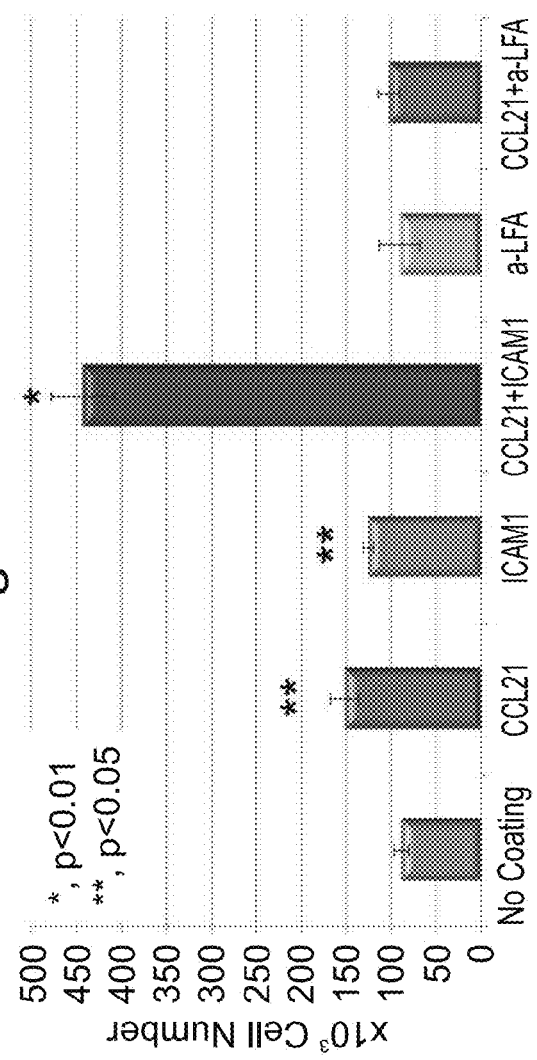

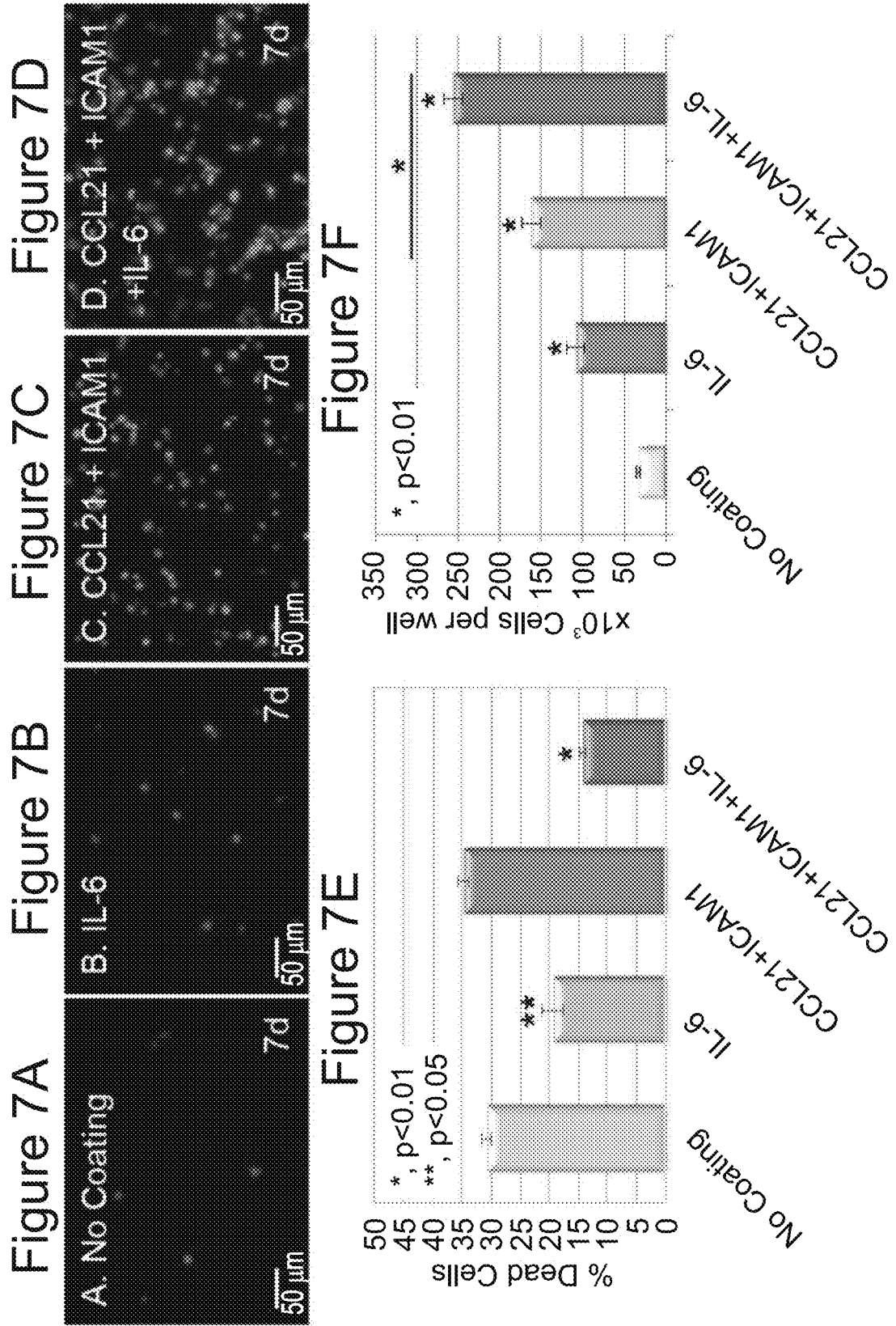

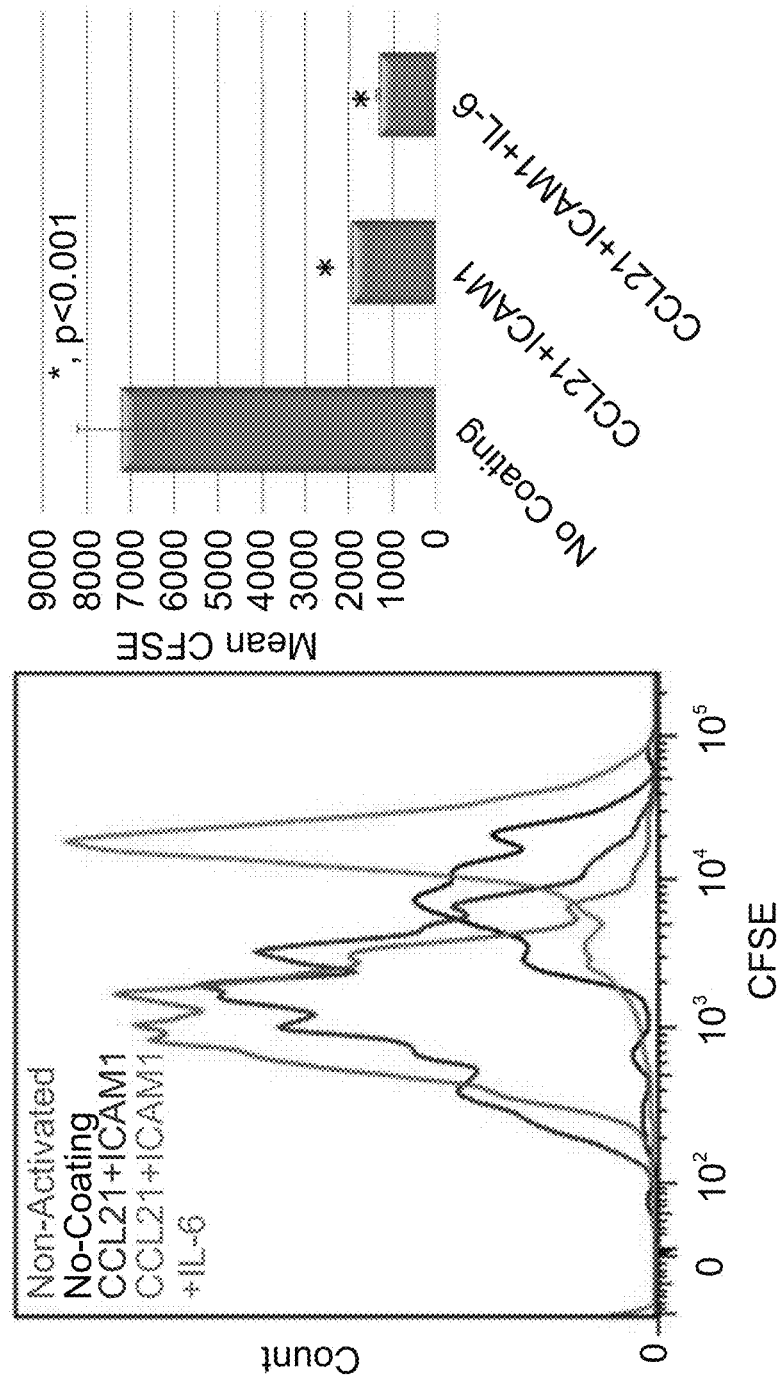

Antigen-loaded DCs Activation

Beads + IL-2 Activation

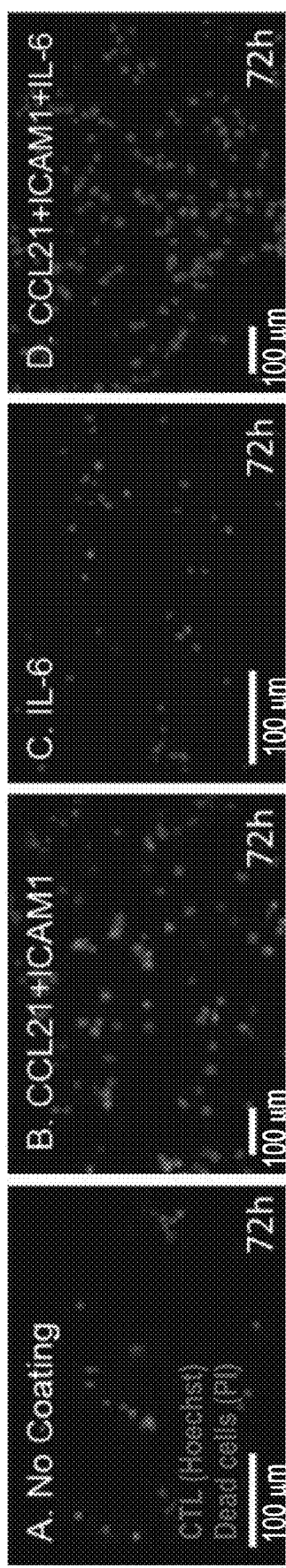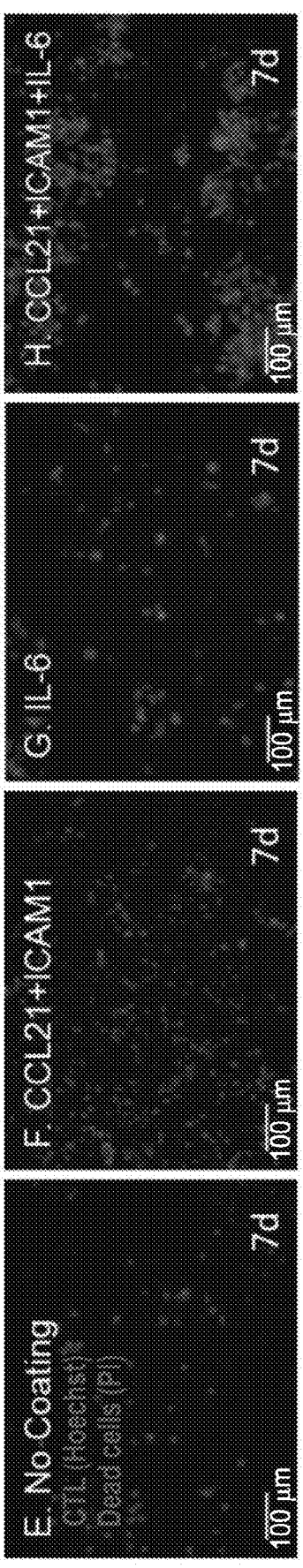

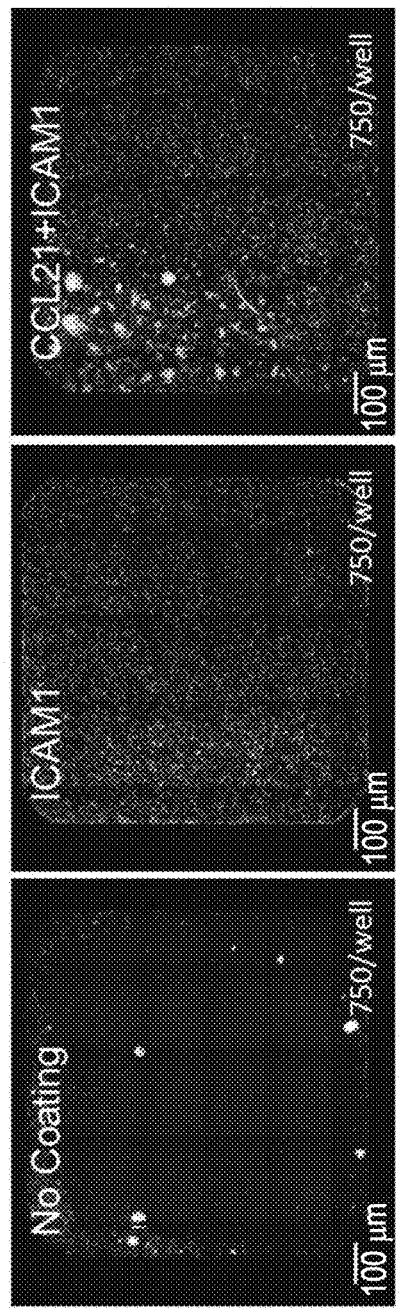

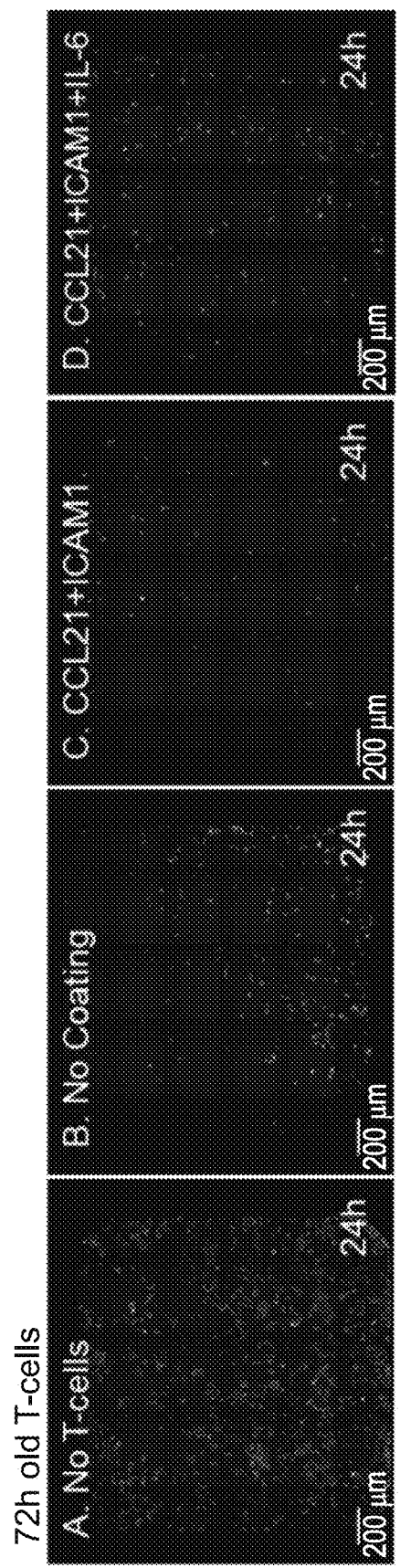
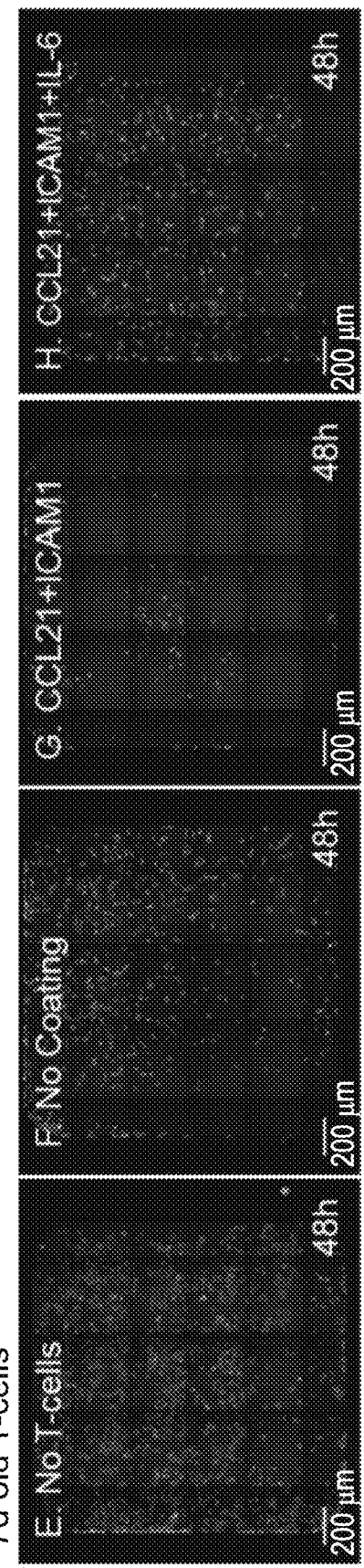

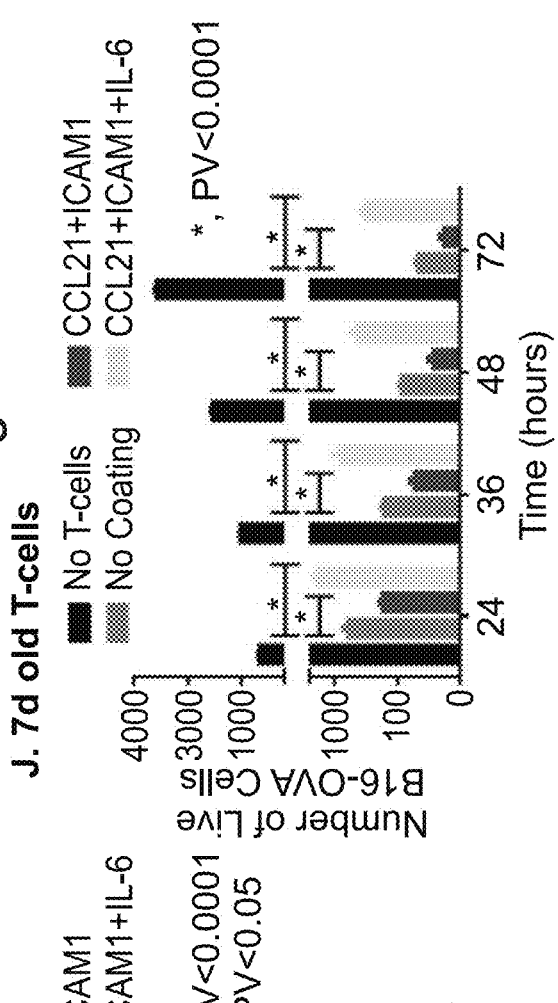
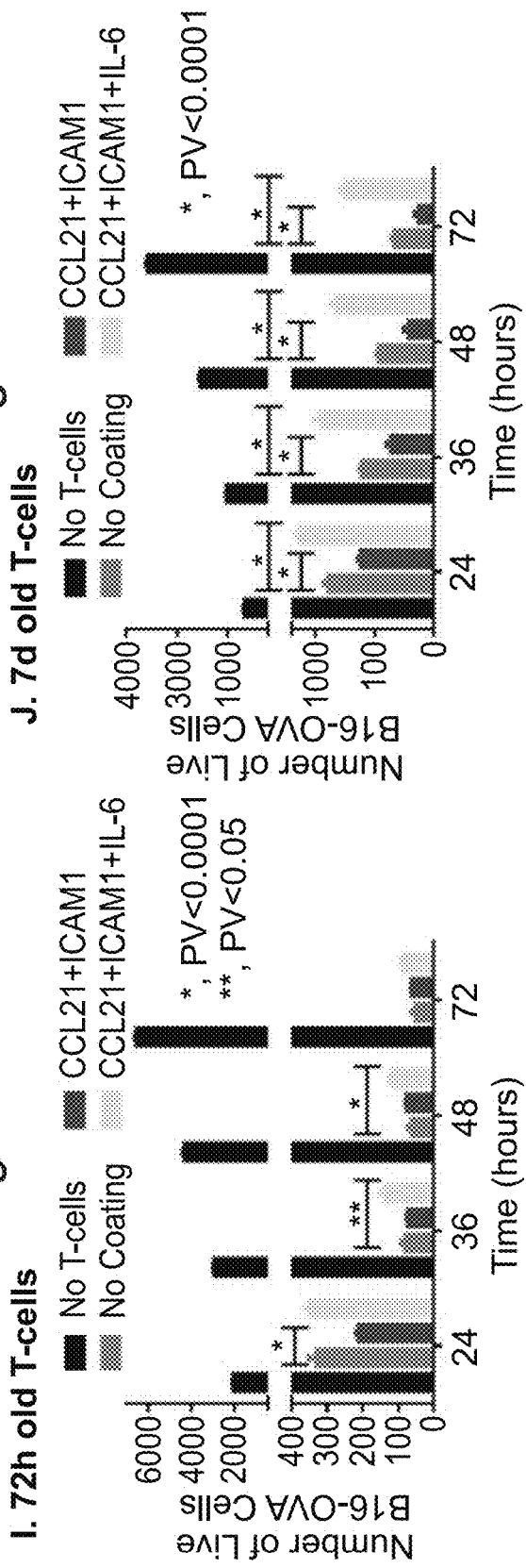
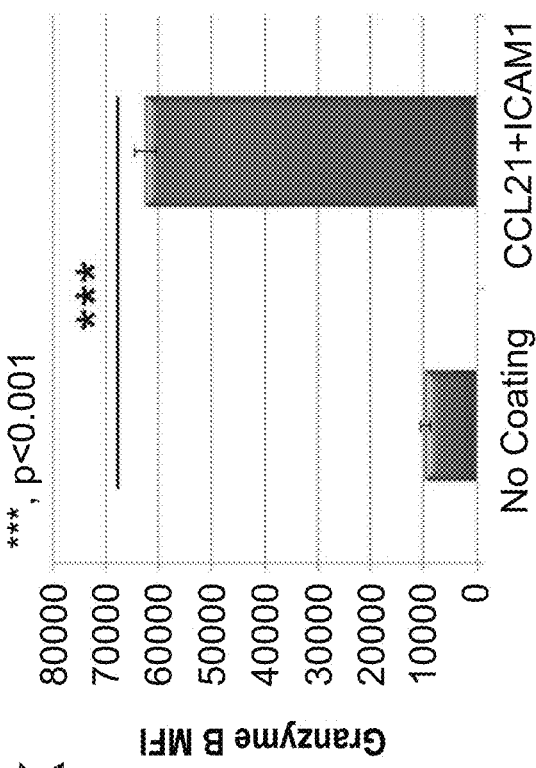
Figure 12I
Figure 12J
Figure 12K

| | | | | |
|---|---|---|---|---|
| Figure 13A1 00:00:00 | Figure 13A2 15:00:00 | Figure 13A3 18:00:00 | Figure 13A4 24:00:00 | Figure 13A5 48:00:00 |
| Figure 13B1 00:00:00 | Figure 13B2 15:00:00 | Figure 13B3 18:00:00 | Figure 13B4 24:00:00 | Figure 13B5 48:00:00 |
| Figure 13C1 00:00:00 | Figure 13C2 15:00:00 | Figure 13C3 18:00:00 | Figure 13C4 24:00:00 | Figure 13C5 48:00:00 |
| Figure 13D1 00:00:00 | Figure 13D2 15:00:00 | Figure 13D3 18:00:00 | Figure 13D4 24:00:00 | Figure 13D5 48:00:00 |

Rows:
- No OVA on target
- No coating
- CCL21 + ICAM1
- CCL21 + ICAM1 + IL-6

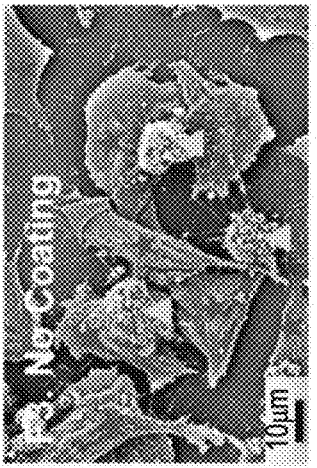
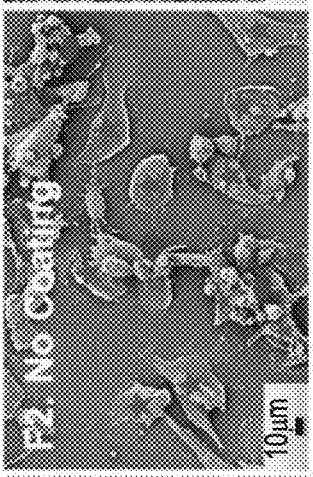
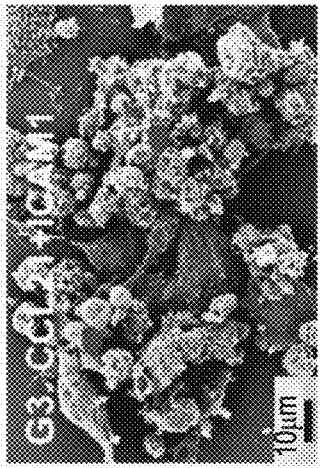
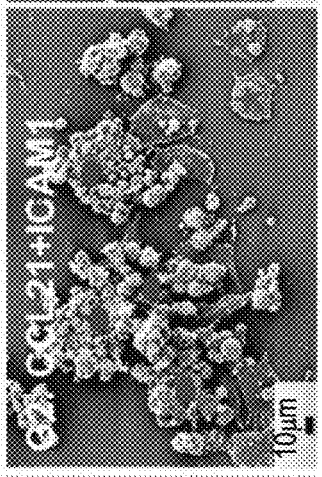

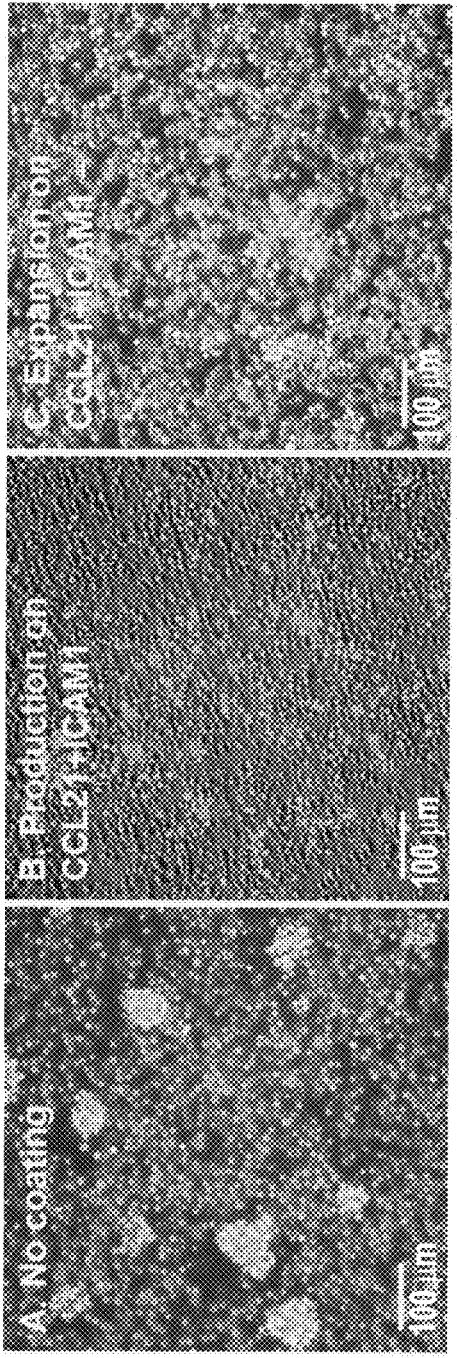
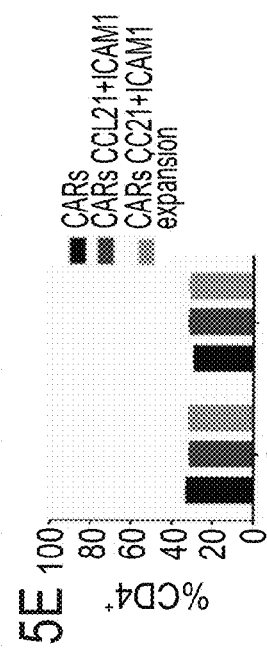
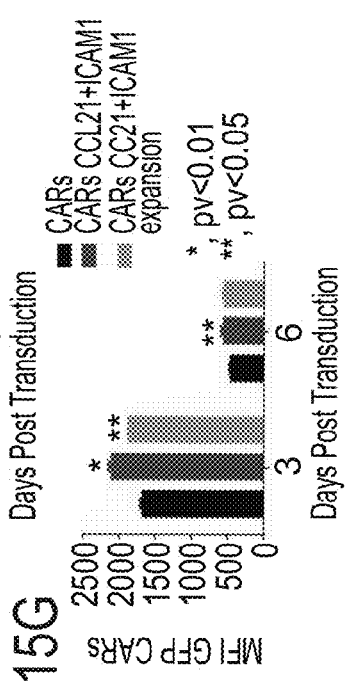
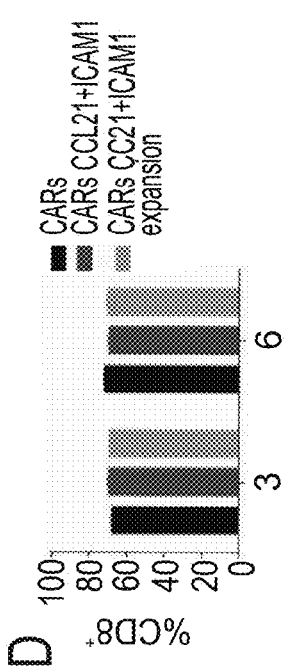
Figure 15A  Figure 15B  Figure 15C
Figure 15D  Figure 15E
Figure 15F  Figure 15G

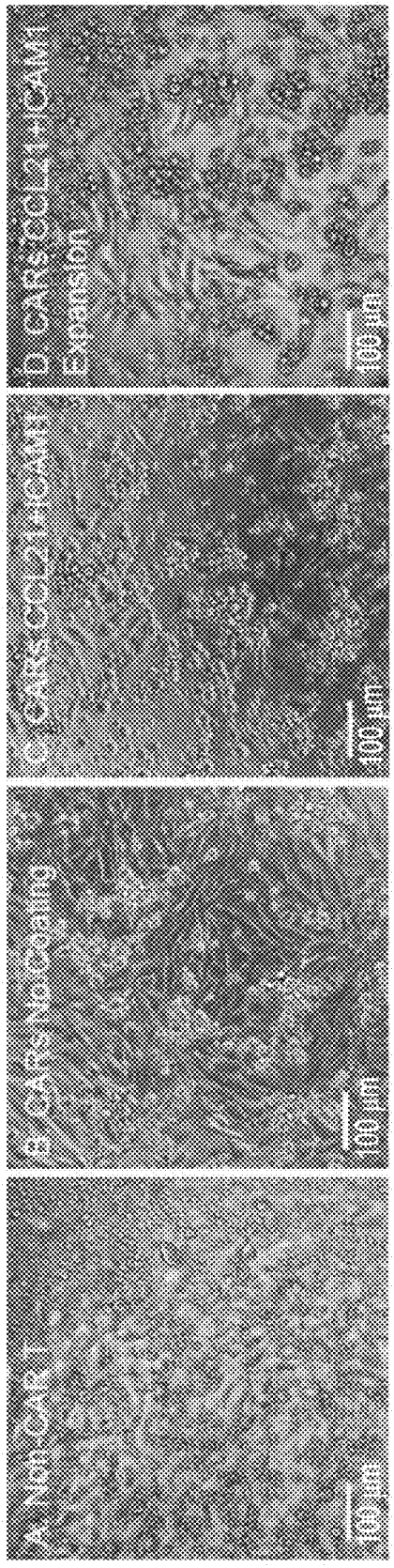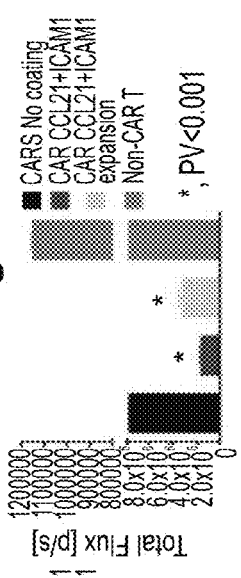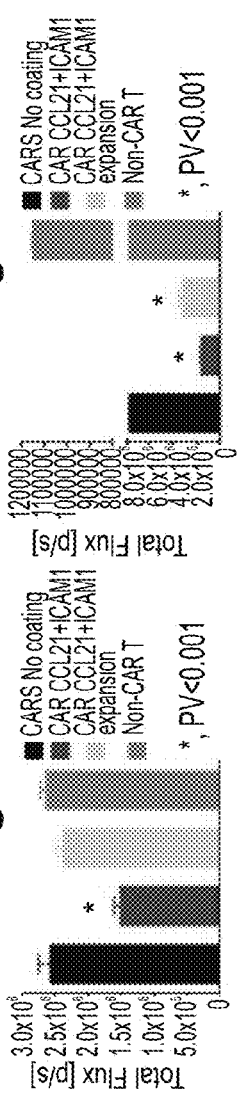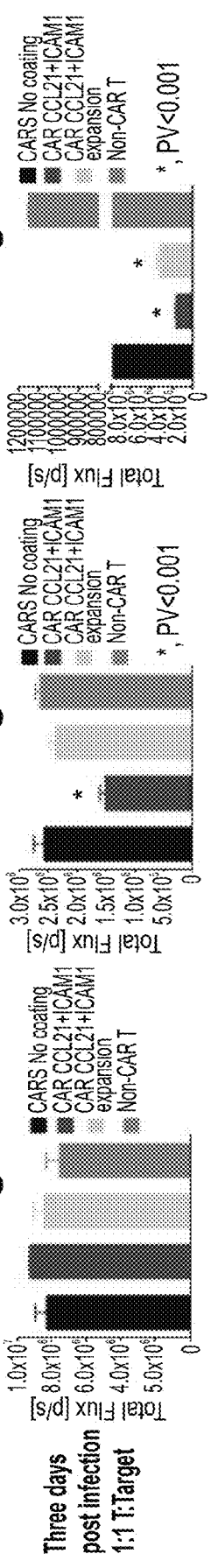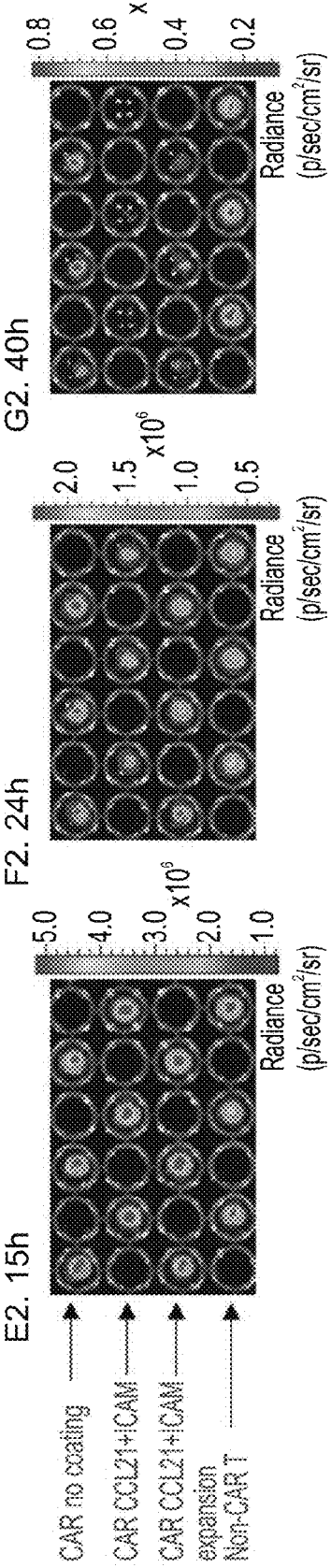

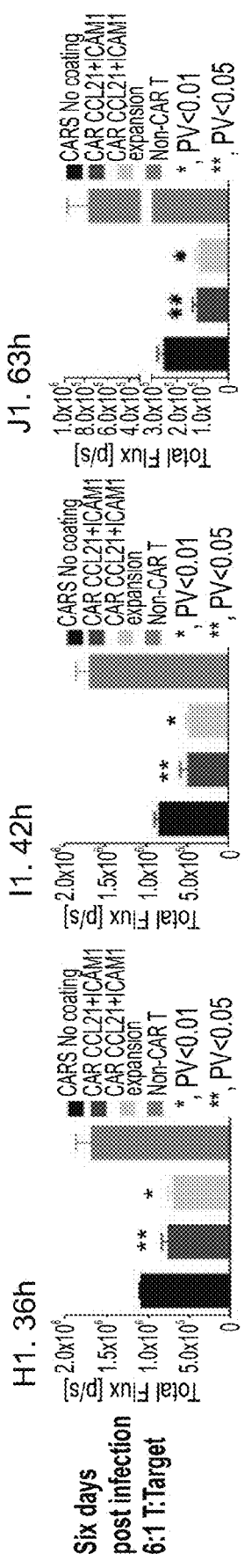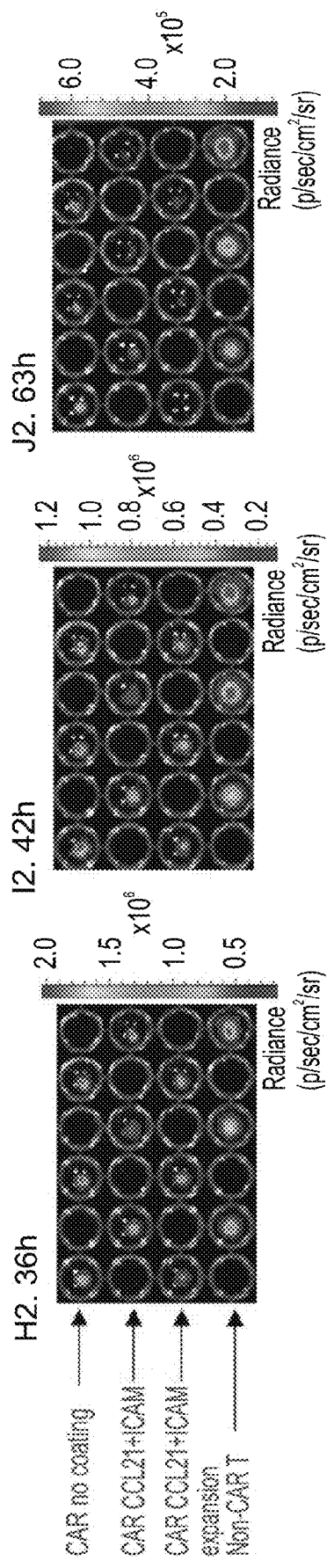
Figure 16H, Figure 16I, Figure 16J

SEQUENCE LISTING

```
<160> NUMBER OF SEQ ID NOS: 2

<210> SEQ ID NO 1
<211> LENGTH: 134
<212> TYPE: PRT
<213> ORGANISM: Homo sapiens

<400> SEQUENCE: 1

Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
```

-continued

```
                115                 120                 125
Gln Thr Pro Lys Gly Pro
    130

<210> SEQ ID NO 2
<211> LENGTH: 532
<212> TYPE: PRT
<213> ORGANISM: Homo sapiens

<400> SEQUENCE: 2

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
        35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350
```

```
-continued

Arg Ala Gln Leu Leu Lys Ala Thr Pro Glu Asp Asn Gly Arg Ser
    355                 360             365

Phe Ser Cys Ser Ala Thr Leu Glu Val Ala Gly Gln Leu Ile His Lys
    370                 375             380

Asn Gln Thr Arg Glu Leu Arg Val Leu Tyr Gly Pro Arg Leu Asp Glu
385             390             395                 400

Arg Asp Cys Pro Gly Asn Trp Thr Trp Pro Glu Asn Ser Gln Gln Thr
                405             410             415

Pro Met Cys Gln Ala Trp Gly Asn Pro Leu Pro Glu Leu Lys Cys Leu
            420             425             430

Lys Asp Gly Thr Phe Pro Leu Pro Ile Gly Glu Ser Val Thr Val Thr
        435             440             445

Arg Asp Leu Glu Gly Thr Tyr Leu Cys Arg Ala Arg Ser Thr Gln Gly
    450             455             460

Glu Val Thr Arg Lys Val Thr Val Asn Val Leu Ser Pro Arg Tyr Glu
465             470             475                 480

Ile Val Ile Ile Thr Val Val Ala Ala Ala Val Ile Met Gly Thr Ala
            485             490             495

Gly Leu Ser Thr Tyr Leu Tyr Asn Arg Gln Arg Lys Ile Lys Lys Tyr
            500             505             510

Arg Leu Gln Gln Ala Gln Lys Gly Thr Pro Met Lys Pro Asn Thr Gln
        515             520             525

Ala Thr Pro Pro
        530
```

METHODS OF CULTURING T CELLS AND USES OF SAME

RELATED APPLICATIONS

This application is a National Phase of PCT Patent Application No. PCT/IL2018/050236 having International filing date of Mar. 2, 2018, which claims the benefit of priority of Israeli Patent Application No. 250916 filed on Mar. 2, 2017. The contents of the above applications are all incorporated by reference as if fully set forth herein in their entirety.

SEQUENCE LISTING STATEMENT

The ASCII file, entitled 78813SequenceListing.txt, created on Sep. 2, 2019, comprising 6,316 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to methods of culturing T cells and uses of same.

Cell-based adoptive immune therapies involving in-vitro activation and expansion of T cells hold promise for the treatment of various diseases. For example, adoptive transfer of antigen-specific $CD8^+$ T cells can be used for the treatment of malignancies and infections, while specific regulatory T cells (Tregs) can be harnessed for suppression of autoimmune processes. A major challenge for T cell based immune therapies is the necessity to expand T cells in large quantities (e.g., 40 population doublings), while maintaining their functionality at the time of re-infusion.

Naturally occurring T cell activation is initiated by the engagement of the T cell receptor/CD3 complex (TCR/CD3) by a peptide-antigen bound to a major histocompatibility complex (MHC) molecule on the surface of an antigen-presenting cell (APC). While this is the primary signal in T cell activation, other receptor-ligand interactions between APCs and T cells are required for complete activation. In-vivo, T cell activation involves complex cellular processes, intercellular interactions and paracrine stimulations that occur in specific sites within the lymphatic system, commonly referred to as "immune niches". Mimicry of such niches by engineering artificial lymphoid tissues or synthetic immune niches (SIN) is an emerging field, with important implications for adoptive therapies. The development of SINs for the selective stimulation of specific T cells is a particularly challenging mission, as it must encompass the broad diversity of natural immune niches, and the complex interplay between the stromal and immune cell types that reside within them.

Several SIN engineering approaches based on various geometries, physical and chemical parameters produced valuable insights into the molecular complexity and various factors within natural immune niches [see e.g. Shimrit Adutler-Lieber et al. Journal of Autoimmunity 54 (2014) 100-111; Tedla et al. Clin Exp Immunol. (1999) 117: 92-99; Deeths et al. Eur J. Immunol. (1999) 29: 45-53; International Application Publication Nos. WO2014048920 and WO2008108794; and U.S. Pat. Nos. 7,745,140 and 5,731,160]. However, despite growing interest and progress in this field, a SIN which reproduces complex immune responses in-vitro and enables obtaining large amounts of functioning specific T cells for immune therapy remains a challenge.

SUMMARY OF THE INVENTION

According to an aspect of some embodiments of the present invention there is provided a method of culturing T cells, the method comprising culturing T cells in the presence of a T cell stimulator, an exogenous CCL21 and an exogenous ICAM1, thereby culturing the T cells.

According to some embodiments of the invention, each of the CCL21 and ICAM1 are immobilized.

According to an aspect of some embodiments of the present invention there is provided a cell culture comprising T cells, a T cell stimulator, an immobilized CCL21 and an immobilized ICAM1.

According to some embodiments of the invention, the cell culture further comprising a cytokine in a level above the level obtained in the cell culture without addition of the cytokine.

According to some embodiments of the invention, the culture is up to 7 days old.

According to some embodiments of the invention, the culture is up to 6 days old.

According to some embodiments of the invention, the T cells comprise engineered T cells transduced with a nucleic acid encoding an expression product of interest.

According to an aspect of some embodiments of the present invention there is provided a method of producing engineered T cells, the method comprising transducing T cells with a nucleic acid encoding an expression product of interest in the presence of an exogenous chemokine and an exogenous adhesion molecule, thereby producing the engineered T cells.

According to some embodiments of the invention, the expression product of interest is a T cell receptor (TCR) or a chimeric antigen receptor (CAR)

According to some embodiments of the invention, the transducing is effected for 1-3 days.

According to some embodiments of the invention, the method further comprising culturing the T cells in the presence of a T cell stimulator, an exogenous chemokine and an exogenous adhesion molecule prior to the transducing.

According to some embodiments of the invention, the culturing is effected for about 2 days.

According to some embodiments of the invention, the method further comprising culturing the engineered T cells in the presence of a T cell stimulator, an exogenous chemokine and an exogenous adhesion molecule following the transducing.

According to some embodiments of the invention, the culturing is effected for 3-7 days.

According to some embodiments of the invention, the culturing is effected for 3-6 days.

According to some embodiments of the invention, each of the chemokine and adhesion molecule are immobilized.

According to some embodiments of the invention, the chemokine is CCL21.

According to some embodiments of the invention, the adhesion molecule is ICAM1.

According to some embodiments of the invention, the method further comprising adding a cytokine to the culture.

According to some embodiments of the invention, the T cells seeding concentration comprises less than $5 \times 10^4$ cells/ml culture medium.

According to some embodiments of the invention, the T cells are human T cells.

According to some embodiments of the invention, the T cells comprise CD4+ T cells.

According to some embodiments of the invention, the T cells comprise CD8+ T cells.

According to some embodiments of the invention, the cytokine is IL-6.

According to some embodiments of the invention, the cytokine is not IL-6.

According to some embodiments of the invention, the T cells comprise CD4+ T cells and the cytokine is IL-6.

According to some embodiments of the invention, the T cells comprise CD8+ T cells and the cytokine is not IL-6.

According to some embodiments of the invention, the T cell stimulator is an antigen-specific stimulator.

According to some embodiments of the invention, the antigen-specific stimulator comprises a dendritic cell loaded with the antigen.

According to some embodiments of the invention, the T cell stimulator is an antigen non-specific stimulator.

According to some embodiments of the invention, the antigen non-specific stimulator comprises anti-CD3 and anti-CD28 antibodies.

According to some embodiments of the invention, there is provided an isolated T cells obtainable by the method.

According to some embodiments of the invention, there is provided a method of adoptive T cells transfer, the method comprising administering to a subject in need thereof a therapeutically effective amount of the T cells of the present invention, thereby adoptively transferring the T cells to the subject.

According to some embodiments of the invention, there is provided a use of the T cells of the present invention for the manufacture of a medicament identified for adoptive T cell therapy.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1G:
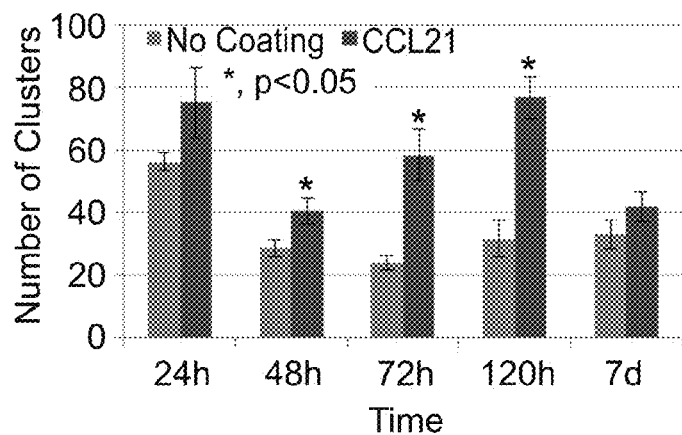
Figure 1H:
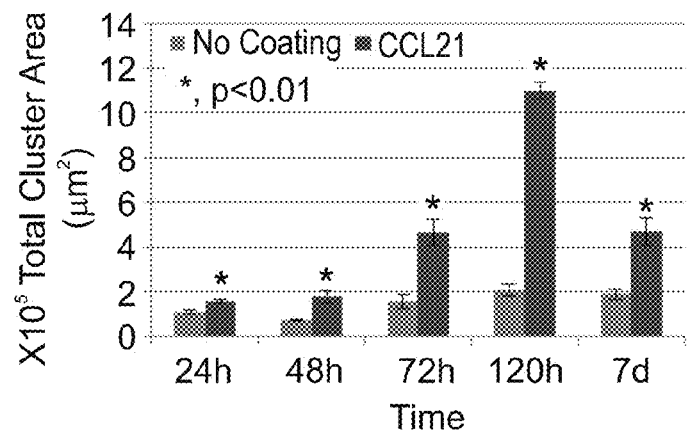
Figure 1I:
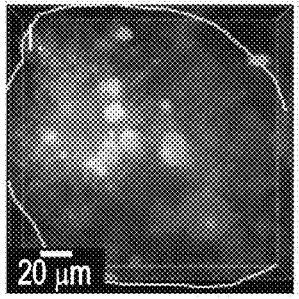
Figure 1J:
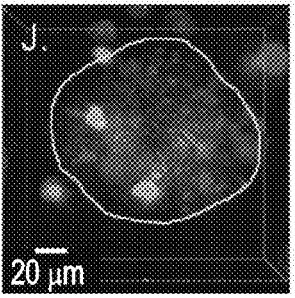
Figure 1K:
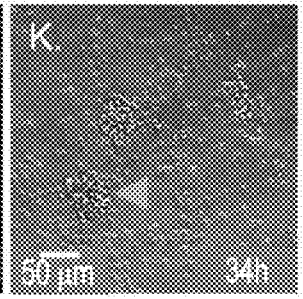
Figure 1L:
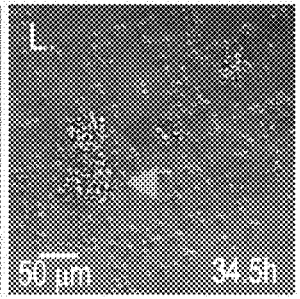
Figure 1M:
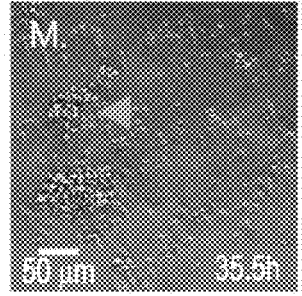
Figure 1N:
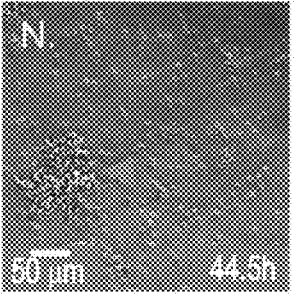
Figure 1O:
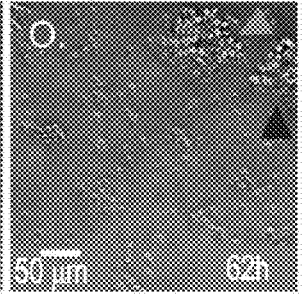
Figure 1P:
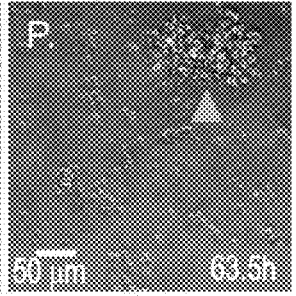
Figure 1Q:
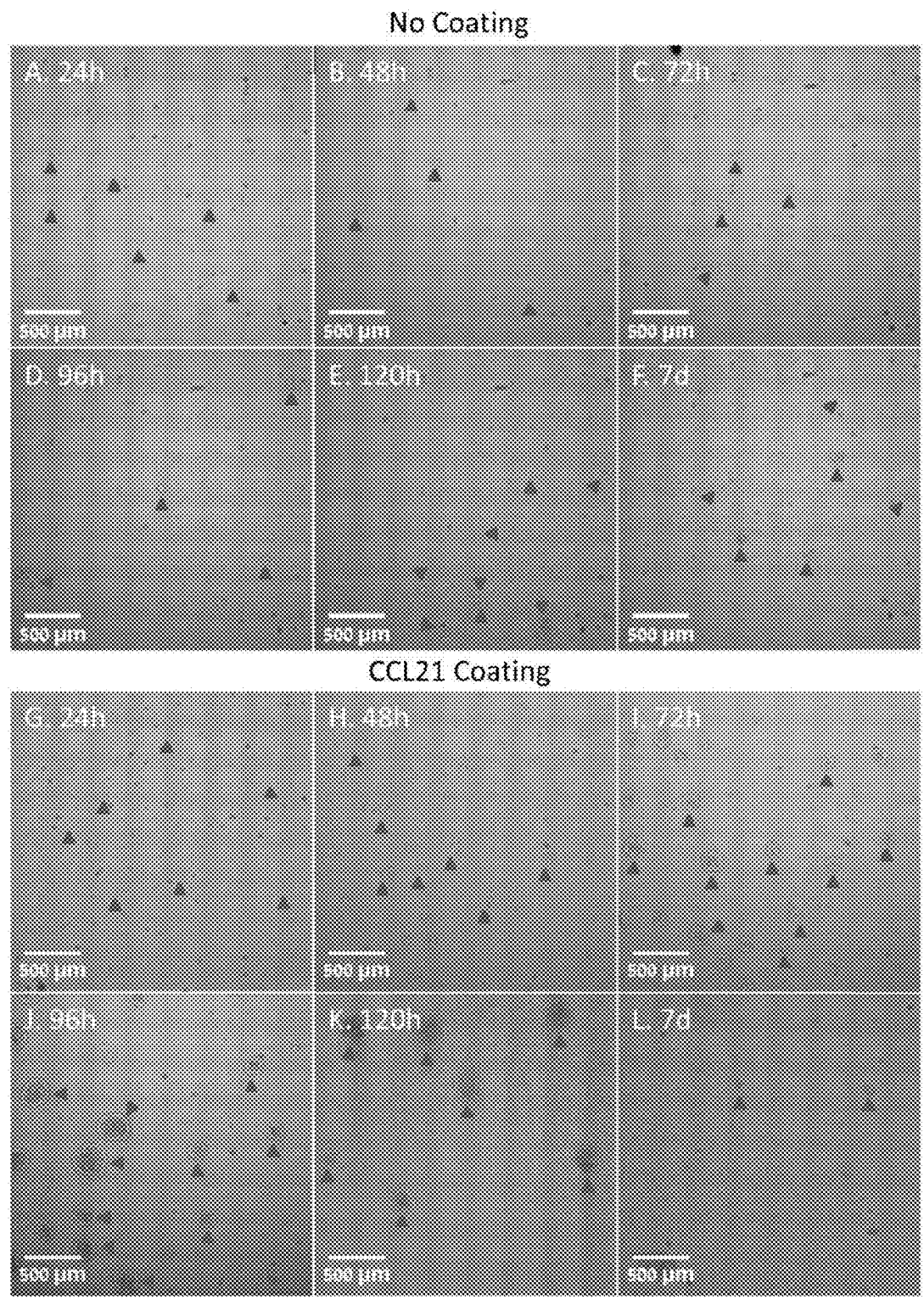
Figure 1R:
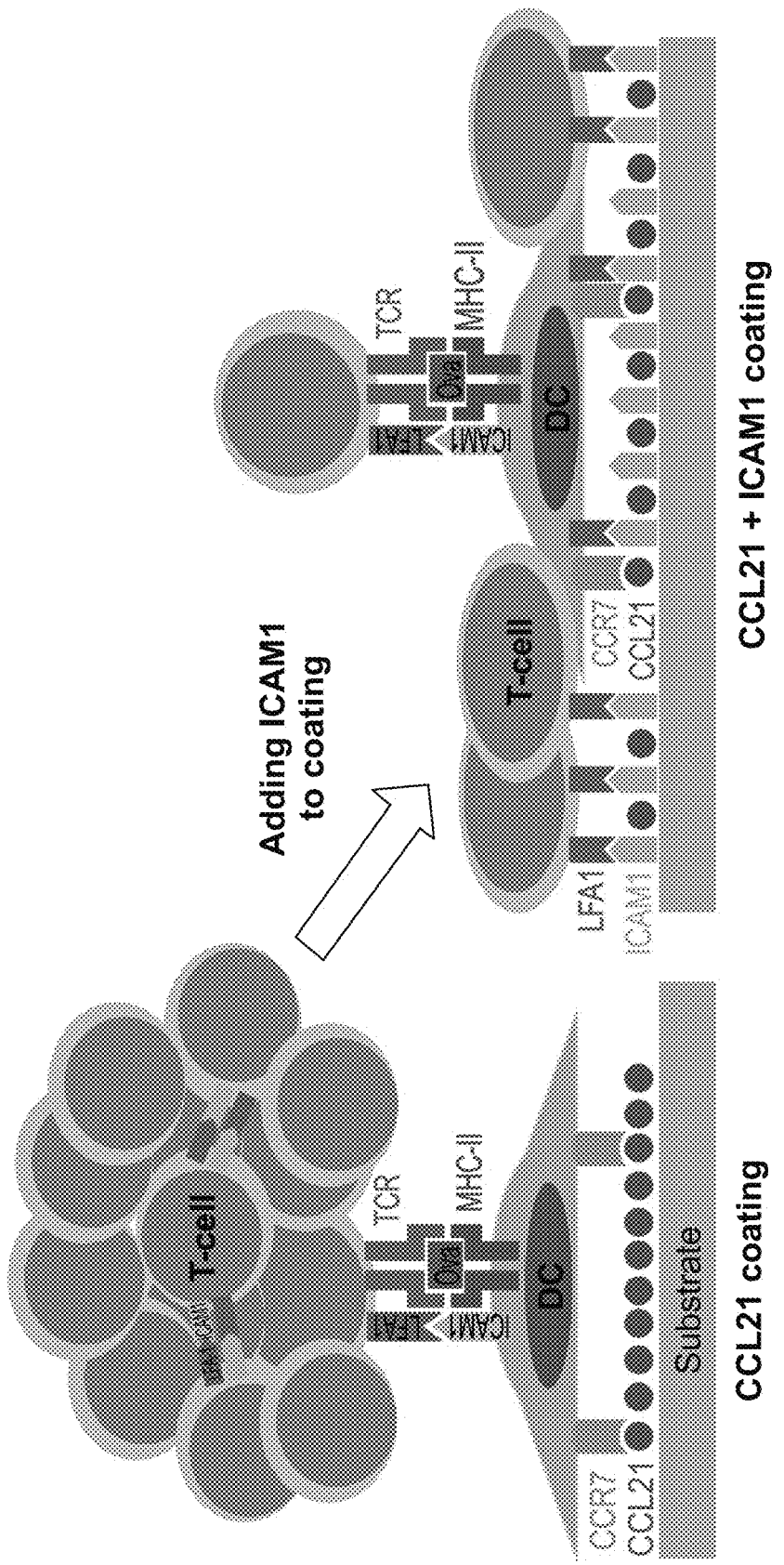

FIGS. 1A-R demonstrate that in-vitro activation of CD4+ T cells with antigen loaded dendritic cells (DCs) on a CCL21 coated surface increases the number and size of T cells clusters as compared to activation on an uncoated surface. FIGS. 1A-F are representative images of OT-II CD4+ T cells and ovalbumin-loaded DCs labeled prior to seeding with membrane-permeable dyes and co-cultured on an uncoated surface (FIGS. 1A-C) or on a CCL21-coated surface (FIGS. 1D-F) for the indicated time period. Red arrows in FIGS. 1C and 1F indicate the clusters. In FIGS. 1A-B and 1D-E, blue cells indicate CD4+ T cells, green cells indicate DC and red cells indicate dead cells. FIGS. 1G-H are bar graphs summarizing the number and total projected areas of clusters formed on uncoated and CCL21-coated surfaces following the indicated culturing times (n=5; error bars represent standard error of the mean). Note that CCL21 increased the number and projected areas of T cell clusters. FIGS. 1I-J are two representative examples of projected images of Z-stack series of single clusters formed on CCL21-coated surfaces (the cluster borders are denoted by a yellow line) demonstrating that the clusters formed are polyclonal. OT-II CD4+ T cells were labeled prior to seeding with membrane-permeable dyes, green, blue or red, mixed in equal numbers and co-cultured with antigen-loaded DCs on CCL21-coated surfaces for 72 hours. The clusters formed were polyclonal, as evidenced by the fact that they contain cells tagged by all three colors. FIGS. 1K-P are time-lapse frames depicting the dynamic properties of the clusters formed on CCL21-coated surfaces. As shown, clusters can merge and single cells can leave existing clusters and join new ones. Cluster merger events are color-coded as follows: red+pink (FIGS. 1K-L)=dark green (FIG. 1M); dark green+light green (FIG. 1M)=light blue (FIG. 1N); light blue+dark blue (FIG. 1O)=purple (FIG. 1P). FIG. 1Q show stitched images (8×8) of the same OT-II CD4+ T cells cultures activated with antigen-loaded DCs on uncoated and CCL21-coated surfaces at the indicated time points. Note that CCL21 coating induced very large clusters as compared to those formed on uncoated controls. The growth in cluster size persisted for 120 hours and decreased dramatically from 7 days onwards. Representative clusters are marked with red arrows. FIG. 1R is a schematic representation of the in-vitro antigen-specific activation on CCL21 and/or ICAM1 coated surfaces model.

FIGS. 2A-J demonstrate that in-vitro activation of CD4+ T cells with antigen loaded DCs on an ICAM1 coated surface reduces T cell clustering and induces their spreading on the culture surface as compared to activation on an uncoated or a CCL21 coated surface. FIGS. 2A-C are representative scanning electron micrographs images, showing T cell clusters formed in cultures without surface coating (FIG. 2A) and in cultures coated with CCL21 (FIG. 2B) or CCL21+ICAM1 (FIG. 2C). Note that coating with ICAM1 induced cell spreading, resulting in significantly smaller and flatter clusters. FIGS. 2D-F are representative transmitted light microscopy images, depicting cell spreading and a decrease in cluster size following culturing on a CCL21+ICAM1 coated surface (FIG. 2E), compared to CCL21 coated surface (FIG. 2D). Addition of anti-LFA1 blocking antibodies to the culture medium of cells cultured on CCL21-coated surfaces inhibited cluster formation (FIG. 2F). FIGS. 2G-J are representative phase contrast images, showing cells at 83 hours following their seeding on uncoated or coated surfaces. Note that the non-clustered cells on an uncoated surface are mostly round, with hardly any cell-cell contacts (FIG. 2G), while cells cultured on CCL21-coated surfaces commonly display an elongated morphology (FIG. 2H); the majority of cells cultured on ICAM1 coated surfaces are elongated, with multiple cell-cell contacts (FIGS. 2I-J).

FIGS. 3A-M demonstrate that in-vitro activation of CD4+ T cells with antigen loaded DCs on an ICAM1 coated surface decreases culture height as compared to activation on an uncoated or a CCL21 coated surface. FIGS. 3A-C are representative transmission electron microscopy images of T cell clusters formed on surfaces coated with CCL21 demonstrating loosely packed clusters, despite multiple membrane contacts between cells within the cluster. FIGS. 3D-H are representative transmission electron microscopy images of transverse sections of T cells stimulated on a CCL21+ICAM1-coated surface (surface marked with red arrows in FIG. 3D) demonstrating that the T cells formed multiple, non-continuous membrane contacts, both with the coated surface (FIGS. 3D, 3E and 3H) and with neighboring cells (FIGS. 3D, 3F and 3G). FIGS. 3I-L are representative fluorescent Z-stack projected images of single T cell clusters formed on the indicated surface coatings. T cell membranes are live-stained green, and cell nuclei are live-stained red. Top views are shown in the top panel and the matching side views are shown in the bottom panel. FIG. 3M is a bar graph summarizing the culture heights on the indicated surface coatings calculated based on Z-stack deconvolution imaging (n=10 replicates; error bars indicate standard error of the mean). Note that clusters formed on surfaces coated with ICAM1, either with or without CCL21, are thinner as compared to those formed on uncoated surfaces; while very large and thick clusters are induced by coating with CCL21.

Figure 4B:
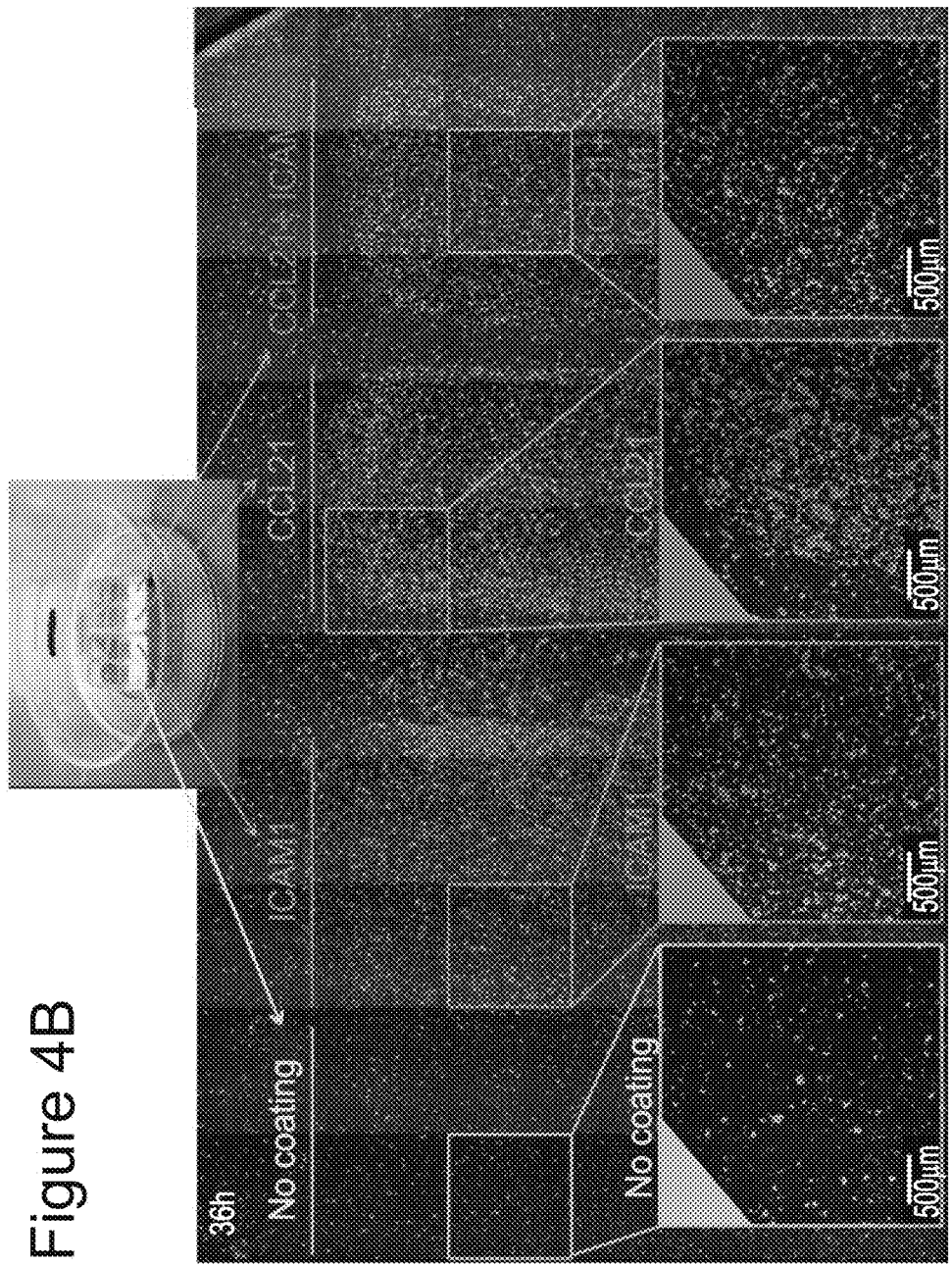
Figure 4C:
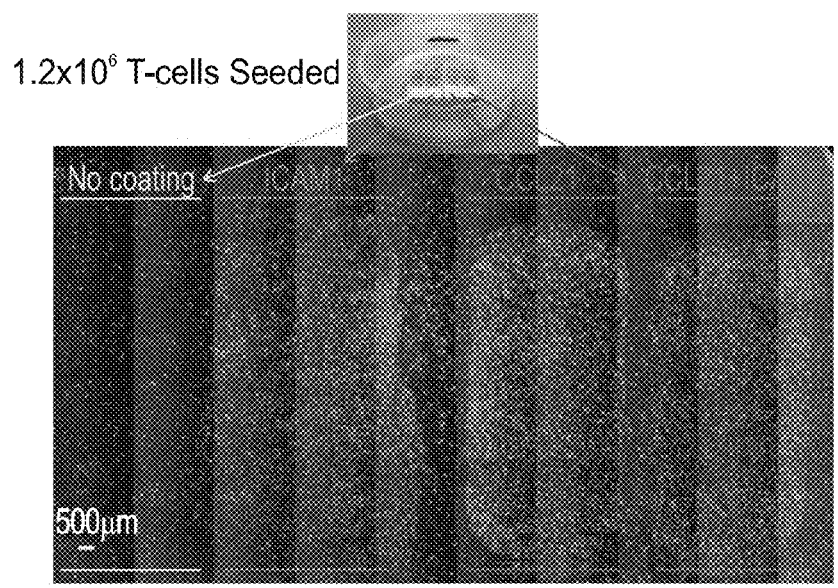
Figure 4D:
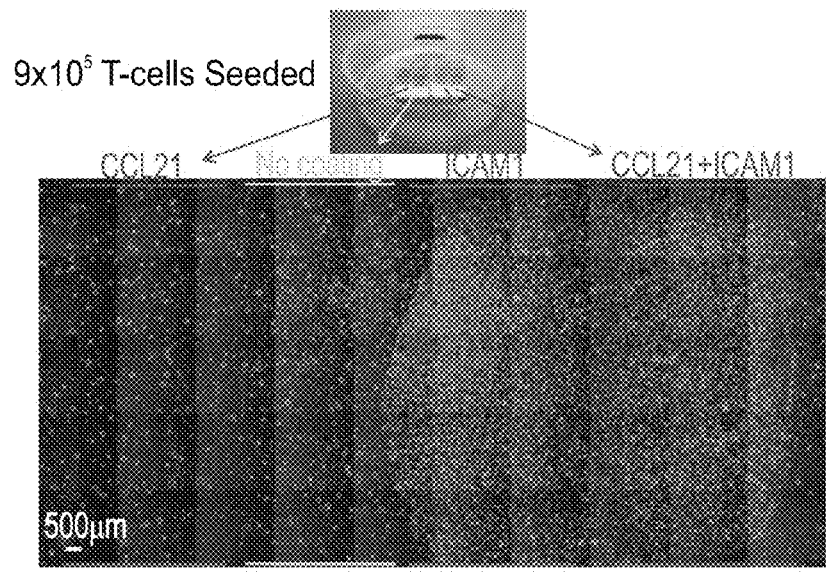
Figure 4E:
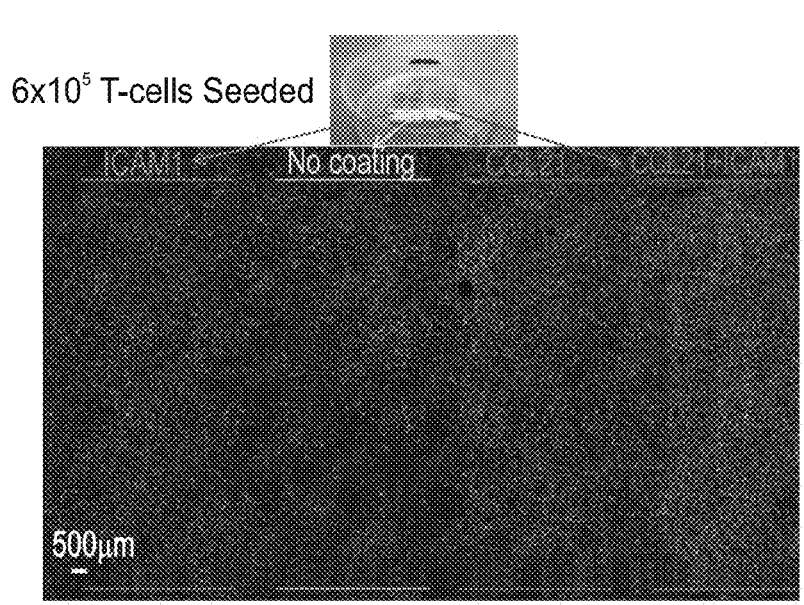

FIGS. 4A-E demonstrate that the effects of CCL21 and ICAM1 on cell morphology are confined to functionalized areas along the surface. FIG. 4A is a schematic representation of the experimental layout. FIGS. 4B-E are stitched images of the surface with cultured T cells ($1.2 \times 10^6$ cells; $1.2 \times 10^6$ cells; $9 \times 10^5$ cells and $6 \times 10^5$ cells in FIG. 4B-E, respectively), taken at 36 hours post seeding, in which each area is marked underneath the horizontal lines: no coating is marked in yellow; ICAM1 in blue; CCL21 in green; and CCL21+ICAM1 in purple. Magnified single fields are shown for each area in FIG. 4B.

FIGS. 5A-M demonstrate that in-vitro activation of CD4$^+$ T cells by antigen loaded DCs on CCL21+ICAM1 coated surfaces increases viable cell numbers of antigen-specific T cells as compared to activation on a surface coated with CCL21 only or ICAM1 only. FIGS. 5A-H are representative fluorescent images of T cells grown on different coated surfaces following breaking down of the clusters and their spin-down. Images were taken following 72 hours (FIGS. 5A-D) and 7 days (FIGS. 5E-H) of culture. Cell nuclei are stained blue in all cells, and red only in dead cells. FIG. 5I shows bar graphs demonstrating viable cell numbers, as quantified using automated image analysis (n=3 replicates; 20 fields of view in each. Error bars represent standard error of the mean). FIG. 5J-M demonstrate that the combined effect of CCL21 and ICAM1 coating on cell number is restricted to antigen-specific T cells, and does not affect non-specific T cells. Seeded T cells consisted of 1% OT-II CD4$^+$ T cells expressing ubiquitin-GFP (green), and 99% non-ova-specific CD4$^+$ T cells. FIGS. 5J-K are representative fluorescent images of cells cultured for 7 days on an uncoated surface (FIG. 5J) or on a surface coated with CCL21+ICAM1 (FIG. 5K), following breaking down of the clusters and their spin-down. All cell nuclei are stained blue, dead cell nuclei in red. FIG. 5L is a bar graph summarizing the ratio of viable OT-II T cells to the originally seeded cell number, as quantified by automated image analysis (n=6 replicates; 20 fields of view in each; error bars represent standard error of the mean). FIG. 5M is a bar graph summarizing the ratio of viable non-ova T cells to the originally seeded cell number as quantified by automated image analysis (n=6 replicates; 20 fields of view in each; error bars represent standard error), in cultures with non-ova T cells alone (marked as 100%) or with 1% OT-II T cells expressing ubiquitin-GFP (marked as 99%). Note that unlike the enrichment of ova-specific T cells (FIG. 5L), the ratio of the final number of non-specific cells to the originally seeded cell number was low (0.03-0.23), indicating no significant proliferation and massive cell death of the non-specific T cells.

FIGS. 6A-D demonstrate that increased CD4$^+$ T cell expansion on CCL21 and ICAM1 coated surfaces depends on ICAM1-LFA1 signaling. In this experimental setting, OT-II CD4$^+$ T cells were activated for 24 hours with antigen-loaded DCs and reseeded for an additional 48 hours on the different surface coatings. FIGS. 6A-C are representative images and FIG. 6D is a bar graph summarizing live cell number, calculated using a metabolic cell viability assay (n=4 replicates; error bars represent standard error of the mean).

FIGS. 7A-H demonstrate that IL-6 augments the combined effect of CCL21 and ICAM1 on viable cell number by increasing cell survival. FIGS. 7A-D are representative images of OT-II CD4$^+$ T cells expressing ubiquitin-GFP (green) activated with antigen-loaded DCs on the different indicated surfaces for 7 days, following breaking down of the clusters and their spin-down. Dead cell nuclei are stained in red. FIGS. 7E-F are bar graphs summarizing the percentage of dead cells (FIG. 7E) and the number of viable cells (FIG. 7F), as quantified using automated image analysis (n=5 replicates; 20 fields of view in each; error bars represent standard error of the mean). FIG. 7G shows representative histograms and FIG. 7H is a bar graph summarizing the mean fluorescence intensity of a CFSE proliferation assay of OT-II CD4$^+$ T cells activated with antigen-loaded DCs on the different indicated surfaces, demonstrating the increase in cell proliferation induced by coating with CCL21+ICAM11 with and without IL-6 (n=3 replicates; error bars represent standard error of the mean).

Figure 8A:
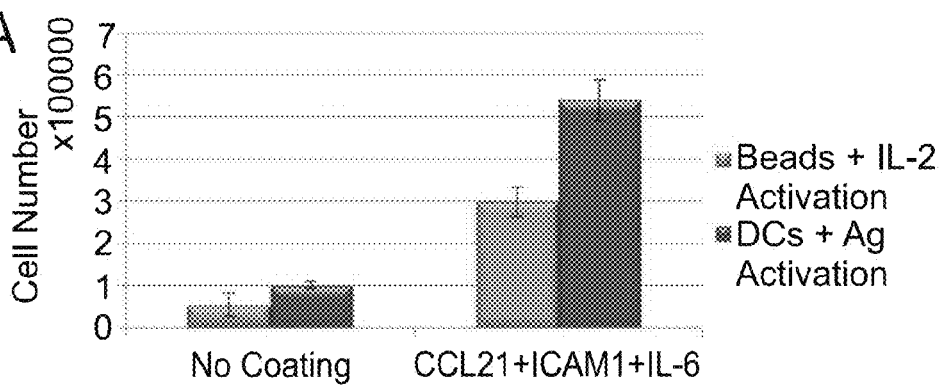
Figures 8B, 8C:
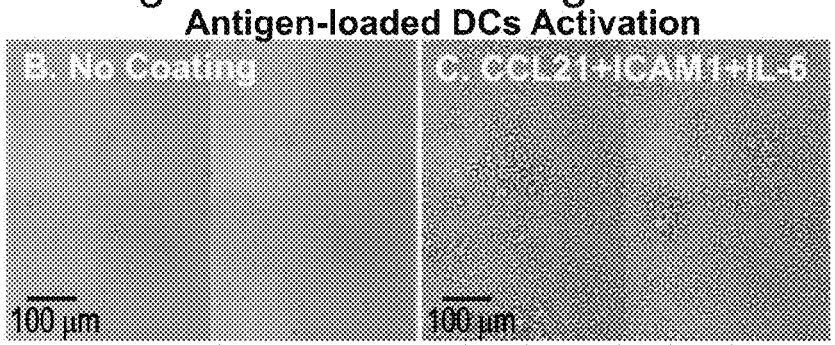
Figures 8D, 8E:
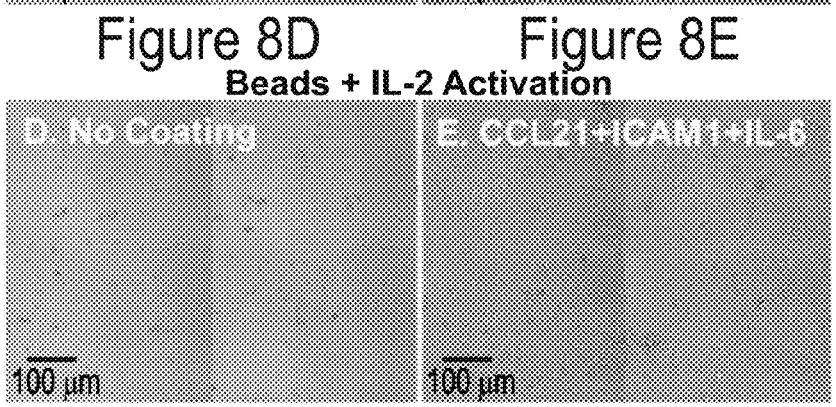
Figure 8F:
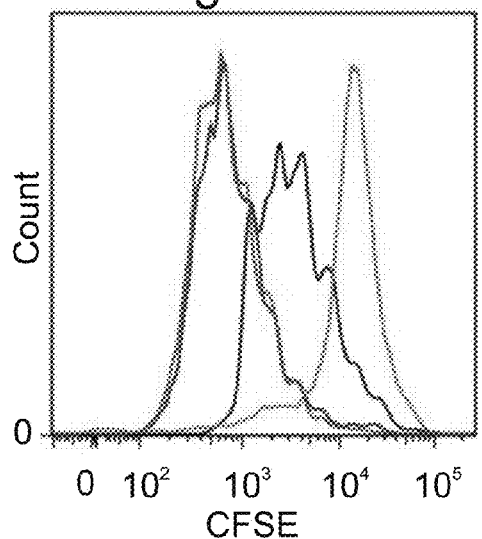
Figure 8G:
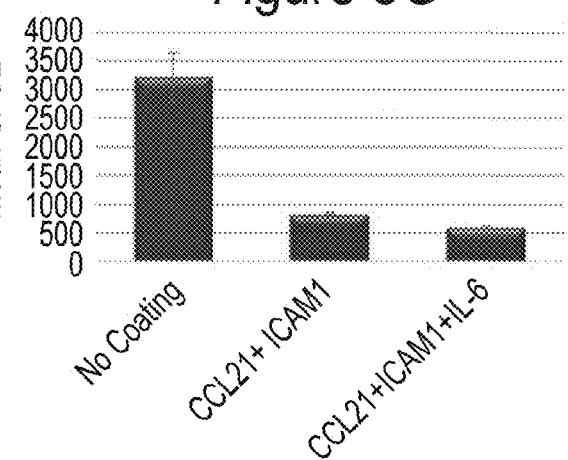

FIGS. 8A-G demonstrate that in-vitro activation of CD4$^+$ T cells with non-specific anti-CD3 and anti-CD28 beads on CCL21 and ICAM1 coated surfaces increases proliferation and viable cell numbers as compared to activation on an uncoated surface. FIG. 8A is a bar graph demonstrating live cell number, calculated using a metabolic cell viability assay (n=4 replicates; error bars represent standard error of the mean), of T cells activated with either antigen-loaded DCs or anti-CD3 and anti-CD28 activation beads on uncoated or CCL21+ICAM1 coated surfaces in the presence of IL-6. FIGS. 8B-E are representative images demonstrating the higher cell density in cultures on CCL21+ICAM1 coated surfaces as compared to uncoated surfaces in both activation methods, i.e. antigen-loaded DCs (FIGS. 8B-C) and anti-CD3 and anti-CD28 activation beads (FIGS. 8D-E). FIG. 8F shows representative histograms and FIG. 8G is a bar graph summarizing the mean fluorescence intensity of a CFSE proliferation assay of OT-II CD4$^+$ T cells activated with anti-CD3 and anti-CD28 activation beads on the different indicated surfaces, demonstrating the increase in cell proliferation induced by coating with CCL21+ICAM1 with and without IL-6 (n=3 replicates; error bars represent standard error of the mean).

Figure 9A:
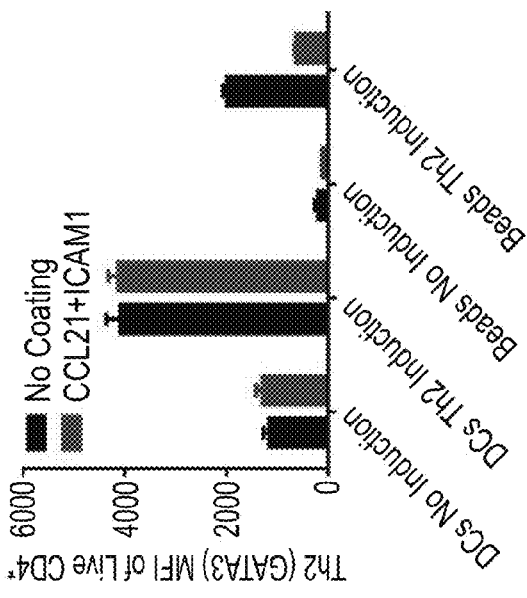
Figure 9B:
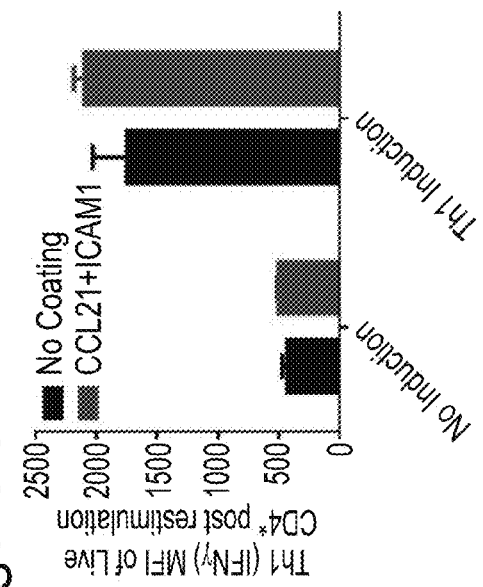
Figure 9C:
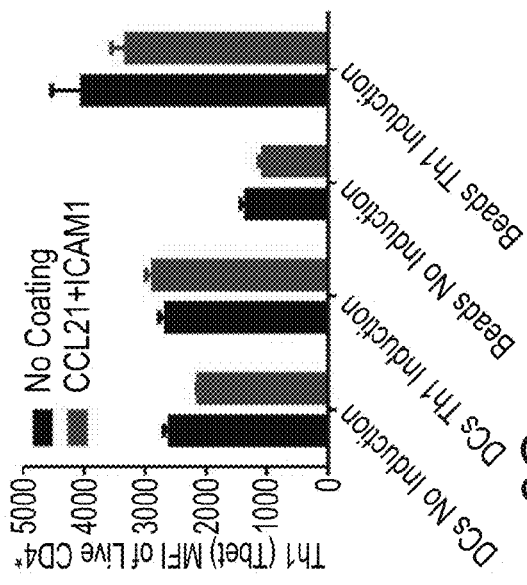
Figure 9D:
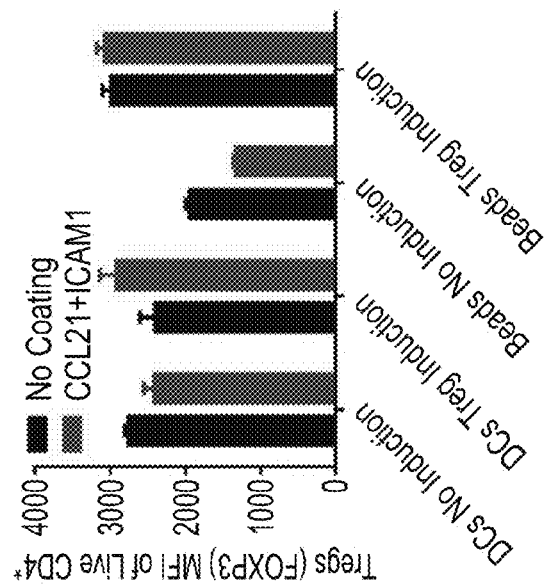

FIGS. 9A-D demonstrate that in-vitro activation of CD4$^+$ T cells on a CCL21 and ICAM1 coated surface do not significantly affect their sub-differentiation compared to activation on an uncoated surface. FIGS. 9A-C are bar graphs summarizing the proportions of Th1 (FIG. 9A), Th2 (FIG. 9B) and Tregs (FIG. 9C) following activation with antigen-loaded DCs or anti-CD3 anti-CD28 activation beads with and without induction of sub-differentiation (n=3 replicates; Error bars represent standard error of the mean). FIG. 9D is a bar graph summarizing the mean fluorescent intensity of IFNγ staining of T cells following re-stimulation. Cells were activated using antigen-loaded DCs and cultured on an uncoated or a CCL21+ICAM1 coated surface with or without induction of Th1 sub-differentiation (n=3 replicates; error bars represent standard error of the mean).

Figure 10B:
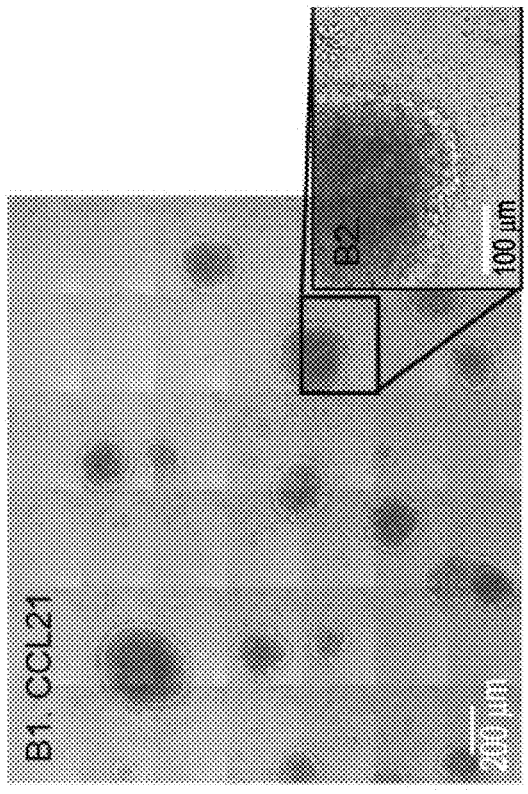
Figure 10D:
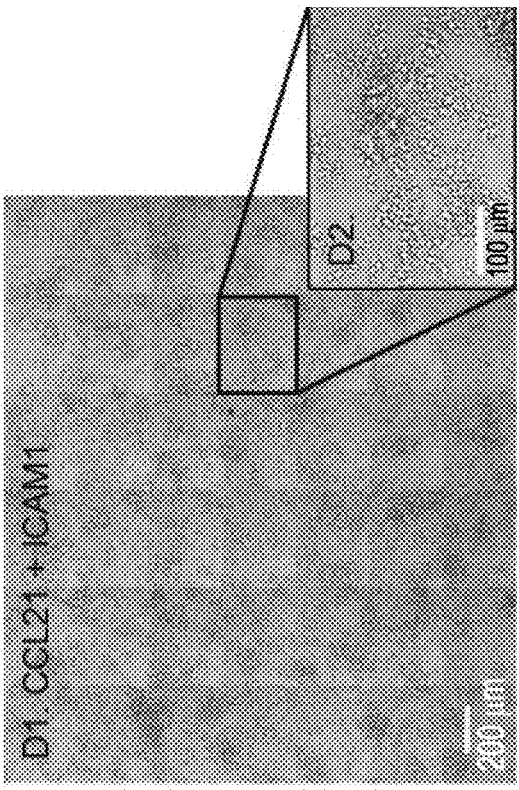

FIGS. 10A-D demonstrate that in-vitro activation of $CD8^+$ T cells on a CCL21 coated surface increases the size of $CD8^+$ T cell clusters while activation on a ICAM1 coated surface transforms the clusters into surface-attached monolayers. Shown are transmitted light microscopy images, depicting topological changes in co-cultures of OT-I $CD8^+$ T cells and ovalbumin-loaded DCs on either uncoated surface (FIG. 10A), CCL21 coated surface (FIG. 10B), ICAM1 coated surface (FIG. 10C) or CCL21+ICAM1 coated surface (FIG. 10D). Black squares denoted as A2, B2, C2 and D2 show the marked enlarged area in A1, B1, C1 and D1, respectively.

FIGS. 11A-L demonstrate that in-vitro activation of $CD8^+$ T cells with antigen loaded DCs on a CCL21+ICAM1 coated surface increases viable cell numbers of antigen-specific T cells as compared to activation on a surface coated with CCL21 only or ICAM1 only. FIGS. 11A-H are representative fluorescent images of T cells grown on the indicated coated surfaces with or without soluble IL-6 for 72 hours (FIGS. 11A-D) or 7 days (FIG. 11E-H) following breaking down of clusters and spin-down. Cell nuclei are stained blue in all cells and red in dead cells only. FIGS. 11I-L are bar graphs summarizing viable cell numbers and percentage of dead cells at 72 hours (FIGS. 11I-J) and 7 days (FIGS. 11K-L) as quantified using automated image analysis (n=5 replicates; 20 fields of view in each; error bars represent standard error of the mean).

Figure 11J:
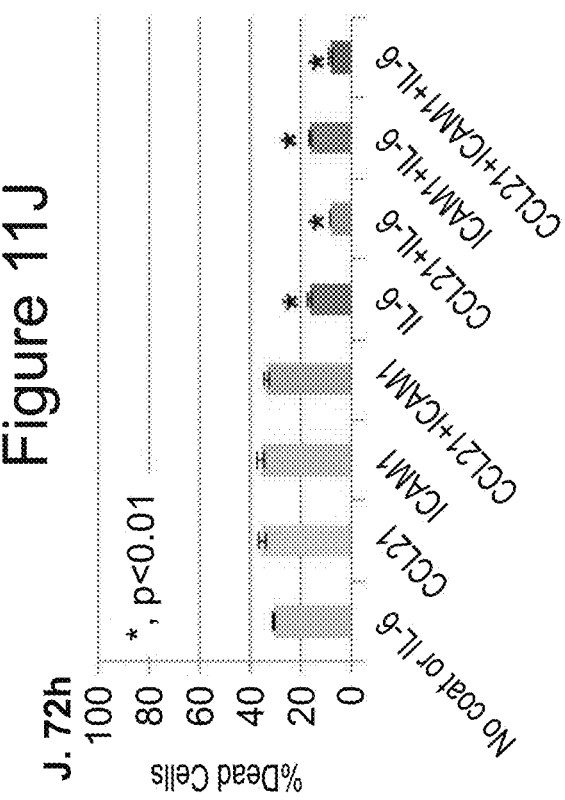
Figure 11L:
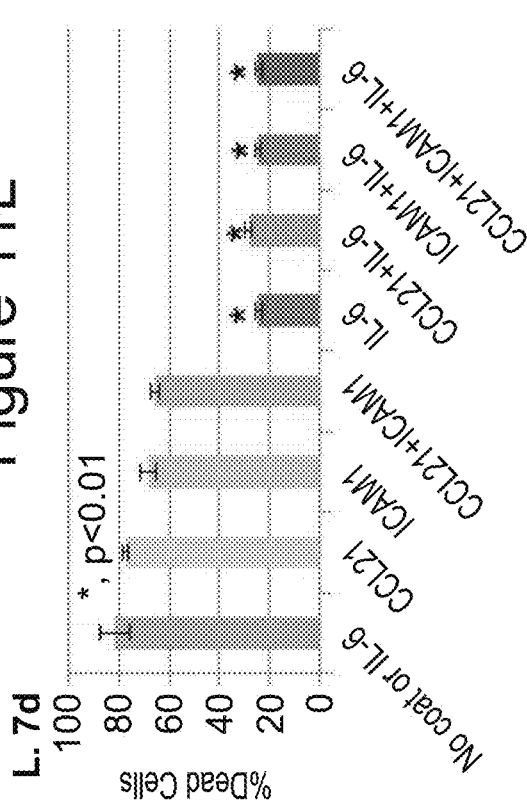
Figure 11I:
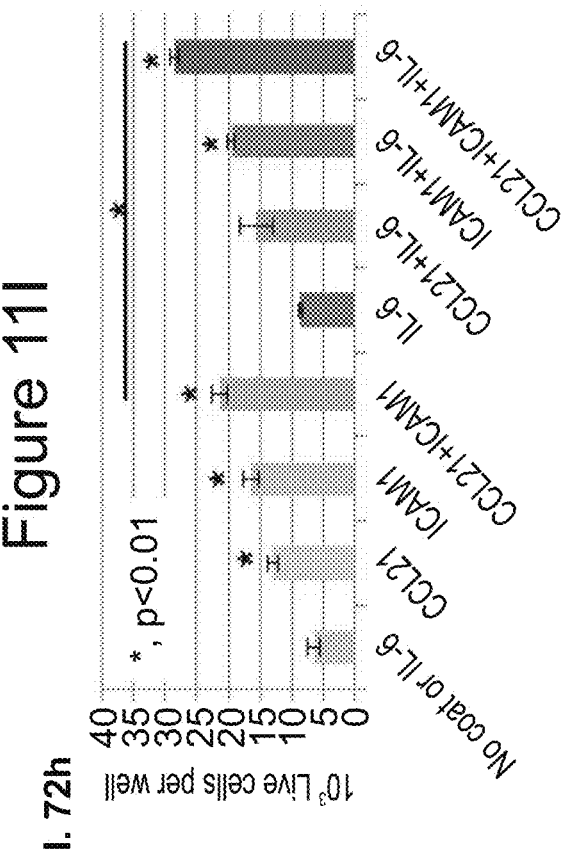
Figure 11K:
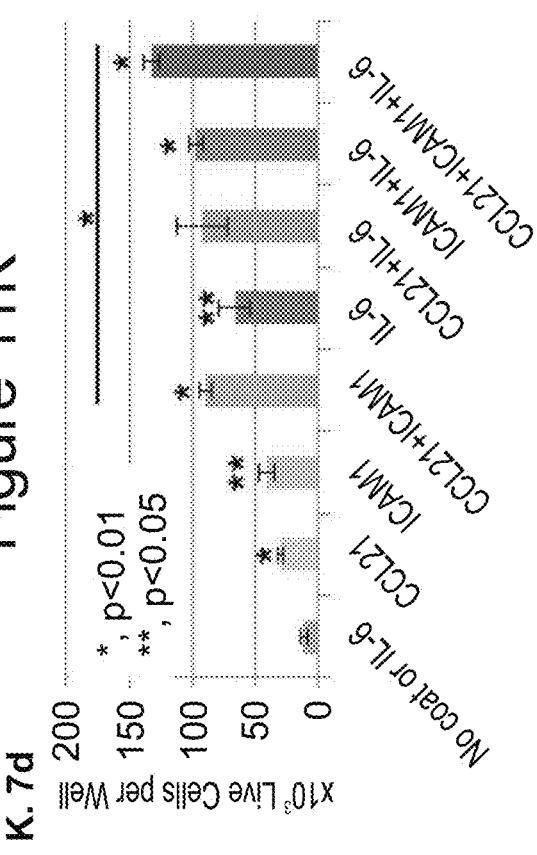
Figure 11M:
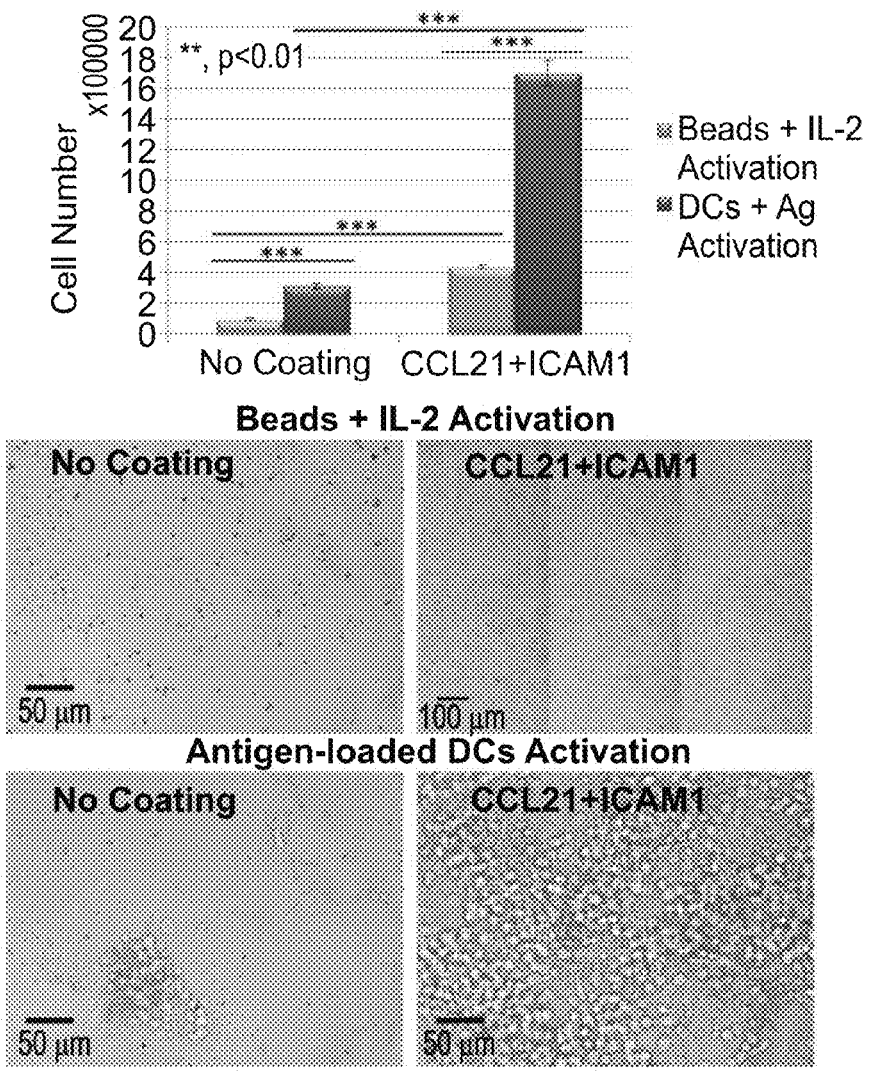
Figure 11N:
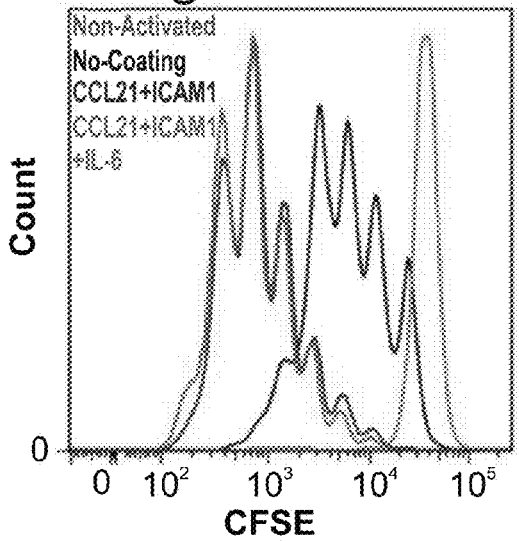
Figure 11O:
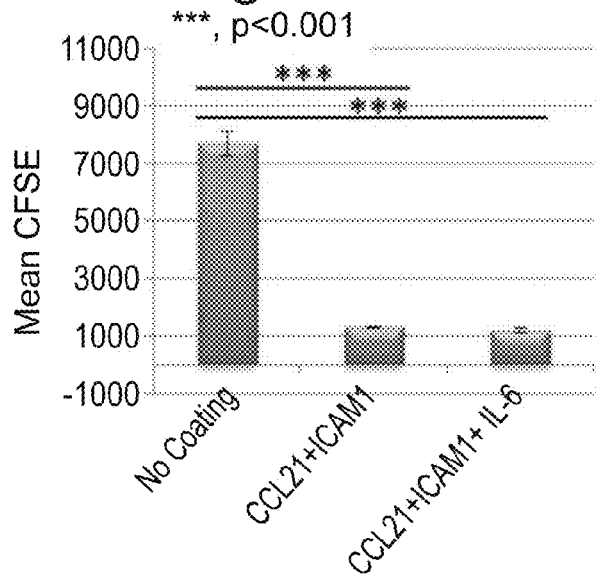

FIGS. 11M-O demonstrate that in-vitro activation of $CD8^+$ T cells with non-specific anti-CD3 and anti-CD28 beads on CCL21 and ICAM1 coated surfaces increases proliferation and viable cell numbers as compared to activation on an uncoated surface. FIG. 11M show a bar graph demonstrating live cell number, calculated using a metabolic cell viability assay (n=4 replicates; error bars represent standard error of the mean), of T cells activated with either antigen-loaded DCs or anti-CD3 and anti-CD28 activation beads on uncoated or CCL21+ICAM1 coated surfaces; and representative images demonstrating the higher cell density in cultures on CCL21+ICAM1 coated surfaces as compared to uncoated surfaces in both activation methods, i.e. antigen-loaded DCs and anti-CD3 and anti-CD28 activation beads. FIG. 11N shows representative histograms and FIG. 11O is a bar graph summarizing the mean fluorescence intensity of a CFSE proliferation assay of OT-I $CD8^+$ T cells activated with anti-CD3 and anti-CD28 activation beads on the different indicated surfaces, demonstrating the increase in cell proliferation induced by coating with CCL21+ICAM1 with and without IL-6 (n=4 technical replicates; error bars represent standard error of the mean).

FIGS. 11P-U are representative stitched fluorescent images of entire 384-wells seeded with low concentrations of T cells grown on either uncoated surfaces (FIGS. 1P and 11S), ICAM1 coated (FIGS. 11Q and 11T) or CCL21+ICAM1 (FIGS. 11R and 11U) for 72 hours. Stained nuclei are seen in white. T cells seeding concentrations were: 7500/ml (750 cells/well, FIGS. 11P-R) or 3250/ml (325 cells/well FIGS. 11S-U).

FIGS. 12A-K demonstrate that in-vitro activation of $CD8^+$ T cells with antigen loaded DCs on a CCL21+ICAM1 coated surface for 7 days increases their killing compared to activation on an uncoated surface. $CD8^+$ T cells, activated for 72 hours (FIGS. 12A-D and 12I) or 7 days (FIGS. 12E-H and 12J), were subsequently co-cultured with B16-OVA-GFP cells for the indicated times. FIGS. 12A-H are representative fluorescent stitched images showing an entire well in a 384-wells plate following 24 hours (FIGS. 12A-D) or 48 hours (FIGS. 12E-H) of the activated T cells with the B16-OVA-GFP cells. B16 expressing GFP cells are seen in white. FIGS. 12I-J are bar graphs summarizing the number of viable (e.g. GFP expressing) B16-OVA cells, as quantified using automated image analysis (n=10 replicates/wells; error bars represent standard error of the mean). FIG. 12K is a bar graph demonstrating the increase in mean fluorescent intensity of granzyme B in cytotoxic T cells following their incubation for 24 hours with B16-OVA target cells (n=4 technical replicates/wells; error bars represent standard error of the mean).

FIGS. 13A1-G3 demonstrate that $CD8^+$ T cells activated in-vitro with antigen loaded DCs on a CCL21+ICAM1 coated surface form larger clusters on target cells and kill the target cells more rapidly compared to cells activated on an uncoated surface. FIGS. 13A1-D5 are representative overlays of time-lapse phase contrast and florescent imaging. OT-I $CD8^+$ T cells (unstained), were pre-cultured for 7 days prior to co-culturing on an uncoated surface (FIGS. 13A1-A5 and 13B1-B5), on a CCL21+ICAM1 coated surface (FIGS. 13C1-C5), or a CCL21+ICAM1 coated surface with soluble IL-6 (FIGS. 13D1-D5). The T cells were then co-cultured with either B16-GFP cells (FIGS. 13A1-A5) or B16-0VA-GFP cells (FIGS. 13B1-D5), both shown in green when alive. Note that the B16-GFP cells which do not express ovalbumin were not killed by the OT-I T cells (FIGS. 13A1-A5). The time stamp indicates hh:mm:ss. FIGS. E1-G3 are representative scanning electron micrographs of B16-0VA-GFP cells (large cells spread on the surface) cultured alone (FIGS. 13E1-E3) or co-cultured for 16 hours with OT-I T cells pre-activated on an uncoated surface (FIGS. 13F1-F3), or on a CCL21+ICAM1 coated surface (FIGS. 13G1-G3). Representative target cells are marked with red stars; representative T cell clusters are marked with blue ellipsoids; and representative single T cells are marked with yellow triangles.

Figure 14A:
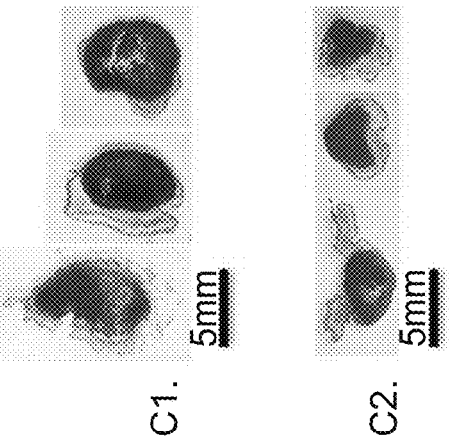
Figure 14B:
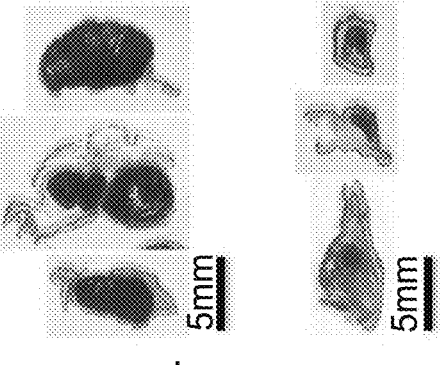
Figure 14C:
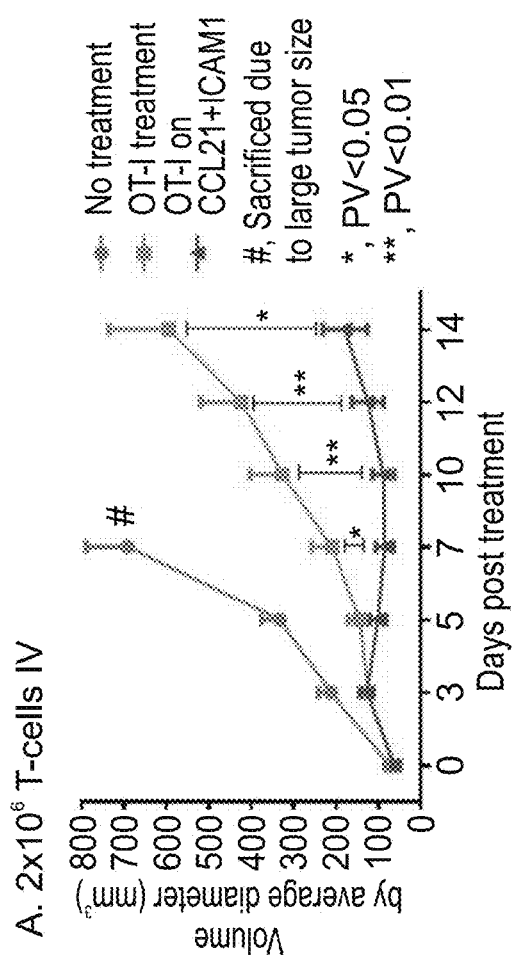
Figure 14D:
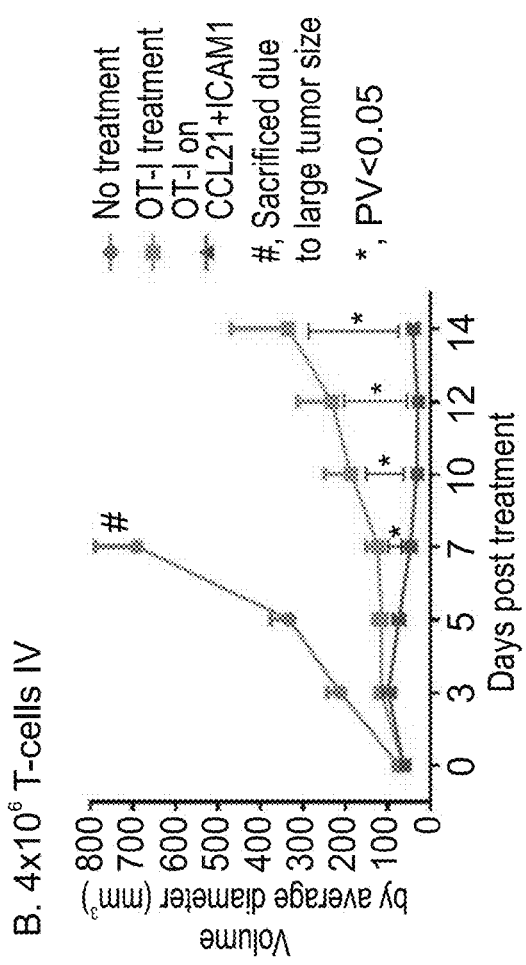

FIGS. 14A-D demonstrate that in-vitro activation of $CD8^+$ T cells with antigen loaded DCs on a CCL21+ICAM1 coated surface increase their in-vivo tumor suppression activity compared to activation on an uncoated surface. C57BL/6 mice were injected ortopically into the flank skin, with $2\times10^6$B 16 cells expressing ovalbumin coupled with GFP. Seven days later, tumor bearing mice were split into treatment groups with similar average and size distribution and injected each intravenously with $2\times10^6$ or $4\times10^6$ activated OT-I $CD8^+$ T cells in PBS. Tumor volume was assessed every 2-3 days using a caliper. FIGS. 14A-B are bar graphs demonstrating averages of tumors volumes, using non-activated $CD8^+$ T cells (grey) or pre-activated $CD8^+$ T cells on an uncoated surface (blue) or on a CCL21+ICAM1 coated surface (pink). Two doses of T cells are shown—mice treated with $2\times10^6$ T cells (FIG. 14B) or $4\times10^6$ T cells (FIG. 14B). n=10 mice; error bars represent standard error of the mean. FIGS. 14C-D are histology sections images of representative tumors of mice treated with $2\times10^6$ (FIG. 14C) or $4\times10^6$ (FIG. 14D) OT-I T cells pre-activated on an uncoated surface (marked as C1 and D1, respectively) or on a CCL21+ICAM1 coated surface (marked as C2 and D2, respectively).

FIGS. 15A-G demonstrate that in-vitro production and activation of human CAR T cells on a CCL21+ICAM1 coated surface reduce T cell clustering, induce cell spreading and increase their expression of HER2-CAR as compared to production and activation on an uncoated surface. FIGS. 15A-C are representative overlays of phase contrast and fluorescent imaging of human T cells, three days following retroviral transduction with a chimeric receptor against a human HER2 protein (HER2-CAR), coupled with GFP. The HER2-CAR T cells were produced and expanded either on an uncoated surface (FIG. 15A), on a CCL21+ICAM1 coated surface (FIG. 15B) or only expanded (i.e., not produced) on a CCL21+ICAM1 coated surface (FIG. 15C). Cells successfully transduced with the HER2-CAR-GFP are seen in green. FIGS. 15D-E are bar graph summarizing the percentages of human T cells expressing CD8 (FIG. 15D), CD4 (FIG. 15E) or HER2-CAR (FIG. 15F) and mean florescent intensity of HER2-CAR-GFP (FIG. 15G) as measured by flow cytometry, at 3 and 6 days following retroviral transduction with HER2-CAR-GFP. N=2 well replicates; error bars represent standard error of the mean. Note, that culturing on a CCL21+ICAM1 coated surface did not affect the percentage of $CD8^+$ (FIG. 15D, ~65%), $CD4^+$ (FIG. 15E, ~30%) or HER2-CAR$^+$ T cells (FIG. 15F, ~65%), but increased the level of HER2-CAR expression (FIG. 15G, ~25%), measured by the mean fluorescent intensity.

FIGS. 16A-J demonstrate that in-vitro production and activation of human CAR T cells on a CCL21+ICAM1 coated surface as well as only expanding CAR T cells on CCL21+ICAM1 coated surface increase killing efficiency of the T cells as compared to production and activation on an uncoated surface. FIG. 16A-D are representative phase contrast images of HER2-Luciferase expressing Renca cells (Target cells), co-cultured with human HER2-CAR T cells, at a ratio of 1:1 for 36 hours. T cells are seen as small, round, mostly clustered cells and target cells are large, elongated, fibroblast-looking and spread cells. FIGS. 16E-G show images of cultured wells (marked as E2, F2 and G2) and bar graphs (marked as E1, F1 and G1) summarizing the measured luminescence and radiance color-map of matching cultured wells of HER2-Luciferase expressing Renca cells, co-cultured 3 days post transduction with human HER2-CAR T cells, at a ratio of 1:1 for 15 hours (FIG. 16E) 24 hours (FIG. 16F) and 40 hours (FIG. 16G). FIGS. 16H-J show images of cultured wells (marked as H2, I2 and J2) and bar graphs (marked as H1, I1 and J1) summarizing the measured luminescence and radiance color-map of matching cultured wells of HER2-Luciferase expressing Renca cells, co-cultured 6 days post transduction with human HER2-CAR T cells, at a ratio of 1:6 for 36 hours (FIG. 16H) 42 hours (FIG. 16I) and 63 hours (FIG. 16J). n=3; error bars represent standard error of the mean.

DESCRIPTION OF SPECIFIC EMBODIMENTS OF THE INVENTION

The present invention, in some embodiments thereof, relates to methods of culturing T cells and uses of same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Cell-based adoptive immune therapies, involving in-vitro activation and expansion of T cells, can be used for the treatment of various diseases including malignancies infections and autoimmune diseases. In-vivo, T cell activation involves complex cellular processes, intercellular interactions and paracrine stimulations that occur in specific sites within the lymphatic system, commonly referred to as "immune niches". Mimicry of such niches by engineering artificial lymphoid tissues or synthetic immune niches (SIN) is an emerging field, with important implications for adoptive therapies. However, despite growing interest and progress in this field, a SIN which reproduces complex immune responses in-vitro and enables obtaining large amounts of functional T cells for immune therapy remains a challenge.

Whilst reducing the present invention to practice, the present inventors have now devised an ex-vivo environment for the efficient expansion of functional $CD4^+$ and/or $CD8^+$ T cells by activating and culturing the T cells in the presence of the chemokine CCL21 and the adhesion molecule ICAM1.

As is illustrated hereinbelow and in the Examples section, which follows, the present inventors demonstrate that in-vitro culturing of specifically or non-specifically activated mouse or human engineered helper ($CD4^+$) and/or cytotoxic ($CD8^+$) T cells in the presence of immobilized CCL21 and ICAM1 induces organization and morphological changes and increases T cell proliferation while not significantly affecting cells survival (Examples 1-2 and 4, FIGS. 1A-R, 2A-J, 3A-M, 4A-E, 5A-M, 6A-D, 7A-H, 8A-H, 9A-D, 10A-D, 11A-O and 15A-G). The combined effect of CCL21 and ICAM1 on T cells expansion was further enhanced by the addition of soluble IL-6 (Examples 1-2, FIGS. 7A-H and 11I-L). Interestingly, the effect of CCL21+ICAM1 coating on organization and morphology was in a direct, local manner limited to the coated area, but not affecting cells in adjacent, non-coated areas (Example 1, FIGS. 4A-E). Furthermore, this effect seems to depend on genuine ICAM1-LFA1 interactions (Example 1, FIGS. 2F and 6A-D). The present inventors further demonstrate that in-vitro activation of the cells on the CCL21+ICAM1 coated surface has an even greater effect on cell density in the culture when the number of T cells ($CD8^+$ T cells) seeded is low (e.g. 3250 cells/ml and 7500 cells/ml) (Example 2, FIGS. 11P-U), an effect clinically significant when only a low number of e.g. tumor infiltrating T cells are isolated from a given tumor for adoptive cell therapy. Moreover, the present inventors show that CCL21+ICAM1 coating did not affect $CD4^+$ T cell sub-differentiation and function (Example 1, FIGS. 9A-D); while it had a combined improved effect on $CD8^+$ T cells in-vitro killing efficiency (Examples 3-4, FIGS. 12A-K, 13A1-G3 and 16A-J) and in-vivo tumor suppression (Example 3, FIGS. 14A-D). Most importantly, the results indicate that the effects induced by the CCL21+ICAM1 coated surface on T cell proliferation and function last several days following the end of exposure to the coating, indicating that a continuous CCL21 and ICAM1 signal at the e.g. tumor site is unnecessary.

Furthermore, in the CAR model (Example 4, FIGS. 15A-G, 16A-J), the effect of in-vitro activation of human HER2-CAR cells on a CCL21+ICAM1 coated surface was more pronounced when the cells were cultured on the CCL21+ICAM1 coated surface at all stages of CARs production and expansion as compared to when cultured on a CCL21+ICAM1 coated surface only at cell expansion and not during induction, indicating an advantage of producing the CAR T cells in a SIN environment.

Taken together, both antigen-specific and non-specific activation of T cells in this newly developed synthetic ex-vivo environment induces a dramatic shift in the organization and morphology of the T cells, as well as greatly improves their expansion and in the case of CD8+ T cells also the in-vitro killing efficiency and in-vivo tumor suppression. Consequently, the present teachings further suggest the use of this developed synthetic in-vitro activation and expansion system in the production of cells used for adoptive T cells therapies for e.g. malignancies, infections, autoimmune and graft rejection diseases. In addition, the synthetic in-vitro activation and expansion system can provide a novel tool for basic research into the mechanisms underlying immunological processes, by enabling the controlled regulation and perturbation of specific factors potentially involved in cell-cell or cell-matrix interactions.

Thus, according to a first aspect of the present invention, there is provided a method of culturing T cells, the method comprising culturing T cells in the presence of a T cell stimulator, an exogenous CCL21 and an exogenous ICAM1, thereby culturing the T cells.

According to another aspect of the present invention, there is provided a cell culture comprising T cells, a T cell stimulator, an immobilized CCL21 and an immobilized ICAM1.

"CCL21" also known as Chemokine (C-C motif) ligand 21, 6Ckine, exodus-2 and secondary lymphoid-tissue chemokine (SLC). CCL21 can bind the chemokine receptor CCR7. According to specific embodiments, the CCL21 protein refers to the human protein, such as provided in the following GenBank Number NP_002980 (SEQ ID NO: 1).

The term also encompasses functional homologues (naturally occurring or synthetically/recombinantly produced), orthologs (from other species) which exhibit the desired activity (i.e., binding CCR7, increasing expansion and at least maintaining activity of T cells such as in combination with ICAM1). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NO: 1 or 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same (as further described hereinbelow).

Sequence identity or homology can be determined using any protein or nucleic acid sequence alignment algorithm such as Blast, ClustalW, and MUSCLE.

The functional homologs also refer to functional portions of CCL21 which maintain the activity of the full length protein (i.e. binding CCR7, increasing expansion and at least maintaining activity of T cells such as in combination with ICAM1).

According to specific embodiments, the CCL21 is a recombinant CCL21.

CCL21 can be commercially obtained from e.g. R&D Systems.

According to specific embodiments, the level of CCL21 in the cultures and methods of the present invention is above the level obtained in a cell culture comprising T cells of the same origin under the same culture conditions without the addition of CCL21.

According to specific embodiments, the concentration of CCL21 in the cultures and methods of the present invention is 100 ng/ml culture medium—1000 µg/ml culture medium, 100 ng/ml culture medium—100 µg/ml culture medium, 500 ng/ml culture medium—500 µg/ml culture medium, 1 µg/ml culture medium—100 µg/ml culture medium or 1 µg/ml culture medium—10 µg/ml culture medium.

According to specific embodiments, the concentration of CCL21 in the cultures and methods of the present invention is about 5 µg/ml culture medium.

According to specific embodiments, the CCL21 is immobilized to a solid support.

"ICAM1" also known as Intercellular Adhesion Molecule 1 and CD54. ICAM1 can bind the CD11a/CD18 or CD11b/CD18 integrins. According to specific embodiments, the ICAM1 protein refers to the human protein, such as provided in the following GenBank Number NP_000192 (SEQ ID NO: 2).

The term also encompasses functional homologues (naturally occurring or synthetically/recombinantly produced), orthologs (from other species) which exhibit the desired activity (i.e., binding CD11a/CD18 or CD11b/CD18 integrins, increasing expansion and at least maintaining activity of T cells such as in combination with CCL21). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NO: 2 or 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same (as further described hereinbelow).

The functional homologs also refer to functional portions of ICAM1 which maintain the activity of the full length protein (i.e. binding CD11a/CD18 or CD11b/CD18 integrins, increasing expansion and at least maintaining activity of T cells such as in combination with CCL21).

According to specific embodiments, the ICAM1 is a recombinant ICAM1.

ICAM1 can be commercially obtained from e.g. R&D Systems.

According to specific embodiments, the level of ICAM1 in the cultures and methods of the present invention is above the level obtained in a cell culture comprising T cells of the same origin under the same culture conditions without the addition of ICAM1.

According to specific embodiments, the concentration of ICAM1 in the cultures and methods of the present invention is 100 ng/ml culture medium—1000 µg/ml culture medium, 100 ng/ml culture medium—100 µg/ml culture medium, 500 ng/ml culture medium—500 µg/ml culture medium, 1 µg/ml culture medium—500 µg/ml culture medium or 1 µg/ml culture medium—100 µg/ml culture medium.

According to specific embodiments, the concentration of ICAM1 in the cultures and methods of the present invention is about 50 µg/ml culture medium.

According to specific embodiments, the CCL21 is immobilized to a solid support.

According to a specific embodiment, the ICAM1 and CCL21 are both human and are optionally both immobilized.

An immobilized molecule or agent disclosed by the present invention may be attached or coupled to the culture vessel or to a matrix within the culture vessel by a variety of chemistries known and available in the art. The attachment may be covalent or noncovalent, electrostatic, or hydrophobic and may be accomplished by a variety of attachment means, including for example, chemical, mechanical, enzymatic, or other means whereby the molecule or the agent is capable of stimulating the T cells.

As used herein, the term "cell culture" or "culture" refers to at least T cells and medium in an ex-vivo, in-vitro environment.

The cell culture is maintained under conditions necessary to support growth and survival, for example, an appropriate temperature (e.g., 37° C.) and atmosphere (e.g., air plus 5% $CO_2$).

The culture may be in a glass, plastic or metal vessel that can provide an aseptic environment for cell culturing. According to specific embodiments, the culture vessel includes dishes, plates, flasks, bottles, vials, bags, bioreactors or any device that can be used to grow cells.

According to specific embodiment, the culture vessel is coated with a synthetic matrix and/or a biological matrix that can increase stimulation and proliferation, such as, but not limited to a synthetic hydrogel, polycarbonate fibers, synthetic spongers and polymers, synthetic ECM, PLGA, PGA, natural ECM materials, agarose, gelatin, laminin, fibrin, collagen chitosan, protosan, and mixtures thereof. Examples for such matrices are provided e.g. in Shimrit Adutler-Lieber et al. Journal of Autoimmunity 54 (2014) 100-111, the contents of which are fully incorporated herein by reference.

According to specific embodiments, the culture vessel is pre-coated (i.e. prior to culturing and/or transducting) with the T cells stimulator, the chemokine (e.g. CCL21) and/or the adhesion molecule (e.g. ICAM1). Coating can be done simultaneously or in a sequential manner as long as the cells are subjected to the factors for a sufficient time and concentration to allow expansion while maintaining the desired phenotype.

According to specific embodiments, the culture vessel is a commercially available culture vessel coated with the T cells stimulator, such as but not limited to anti-CD3/anti-CD28 coated culture vessel such as can be obtained from e.g. Miltenyi Biotech.

According to specific embodiments, the culture vessel is pre-coated (i.e. prior to culturing and/or transducing) with the chemokine (e.g. CCL21) and/or the adhesion molecule (e.g. ICAM1).

The culture medium used by the present invention can be a water-based medium which includes a combination of substances such as salts, nutrients, minerals, vitamins, amino acids, nucleic acids and/or proteins such as cytokines, growth factors and hormones, all of which are needed for cell proliferation and survival. For example, a culture medium can be a synthetic tissue culture medium such as RPMI 1640 medium (can be obtained from e.g. Biological Industries), DMEM (can be obtained from e.g. Biological Industries), MEM (can be obtained from e.g. Biological Industries), AIM-V (can be obtained from e.g. ThermoFisher Scientific), X-Vivo 15 (can be obtained from e.g. Lonza) and X-Vivo 20 (can be obtained from e.g. Lonza), supplemented with the necessary additives as is further described hereinunder. Preferably, all ingredients included in the culture medium of the present invention are substantially pure, with a tissue culture grade.

According to some embodiments of the invention, the culture medium is devoid of any animal contaminants, i.e., animal cells, fluid or pathogens (e.g., viruses infecting animal cells), i.e., being xeno-free.

According to some embodiments of the invention, the culture medium comprises antibiotics (e.g., penicillin, streptomycin, gentamicin), anti-fungal agents (e.g. amphotericin B), L-glutamine or NEAA (non-essential amino acids).

According to a specific embodiment, the medium comprises serum and antibiotics.

According to a specific embodiment, the medium comprises RPMI 1640 medium supplemented with serum, penicillin, streptomycin, glutamine, HEPES, sodium pyruvate and $\beta$-mercaptoethanol.

It should be noted that the culture medium may be periodically refreshed to maintain sufficient levels of supplements and to remove metabolic waste products that can damage the cells. According to specific embodiments, the culture medium is refreshed every 12-96 hours, every 24-72 hours or every 24-48 hours.

According to specific embodiments, the T cells seeding concentration in the culture is $10^3$-$10^6$ cells/ml culture medium, $10^3$-$5\times10^5$ cells/ml culture medium or $10^3$-$10^5$ cells/ml culture medium.

According to specific embodiments, the T cells seeding concentration in the culture is less than $5\times10^4$ cells/ml culture medium.

According to specific embodiments, the T cells seeding concentration in the culture is $10^3$-$5\times10^4$ cells/ml culture medium.

According to specific embodiments, the T cells seeding concentration in the culture is $2\times10^3$-$10^4$ cells/ml culture medium.

According to specific embodiments, the T cells seeding concentration in the culture is about 7500 cells/ml culture medium.

According to specific embodiments, the T cells seeding concentration in the culture is about 3250 cells/ml culture medium.

As the T cells cultured according to the methods of the present invention proliferate during culturing, according to specific embodiments the T cells are serially splitted so as to maintain the desired cell concentration.

According to specific embodiments, the T cells concentration in the culture medium is $10^3$-$10^7$ cells/ml culture medium, $10^3$-$5\times10^6$ cells/ml culture medium or $10^3$-$1\times10^6$ cells/ml culture medium As used herein, the term "T cell" refers to a differentiated lymphocyte with a $CD3^+$, T cell receptor $(TCR)^+$ having either $CD4^+$ or $CD8^+$ phenotype. The T cell may be a naïve, activated or memory T cell. The T cell may be either an effector or a regulatory T cell.

According to specific embodiments, the T cells comprise effector T cells.

As used herein, the term "effector T cell" refers to a T cell that activates or directs other immune cells e.g. by producing cytokines or has a cytotoxic activity e.g., $CD4^+$, Th1/Th2, $CD8^+$ cytotoxic T lymphocyte.

According to other specific embodiments the T cells comprise regulatory T cells.

As used herein, the term "regulatory T cell" or "Treg" refers to a T cell that negatively regulates the activation of other T cells, including effector T cells, as well as innate immune system cells. Treg cells are characterized by sustained suppression of effector T cell responses. According to a specific embodiment, the Treg is a $CD4^+CD25^+Foxp3^+$ T cell.

According to specific embodiments, the T cells comprise $CD4^+$ T cells. According to specific embodiments, the T cells comprise $CD8^+$ T cells.

According to specific embodiments, the T cells are memory T cells. Non-limiting examples of memory T cells include effector memory $CD4^+$ T cells with a $CD3^+/CD4^+/CD45RA^-/CCR7^-$ phenotype, central memory $CD4^+$ T cells with a $CD3^+/CD4^+/CD45RA^-/CCR7^+$ phenotype, effector memory CD8$^+$ T cells with a CD3$^+$/CD8$^+$/CD45RA$^-$/CCR7$^-$ phenotype and central memory CD8$^+$ T cells with a CD3$^+$/CD8$^+$/CD45RA$^-$/CCR7$^+$ phenotype.

According to a specific embodiment, the T cells are human T cells.

According to another specific embodiment, the T cells are mouse or rat T cells.

T cells can be obtained from a number of sources, including peripheral blood mononuclear cells (PBMCs), bone marrow, body tissue (such as lymph node tissue, spleen tissue, and tumors) or cells from tissue fluids. According to specific embodiments, T cells can be obtained from a unit of blood collected from a subject using any number of techniques known to the skilled artisan, as further disclosed hereinbelow. According to other specific embodiments, the T cells are obtained from a tumor tissue obtained from a subject. T cell lines are also available in the art. Thus, according to specific embodiments, any number of T cell lines available in the art, may be used.

As used herein the term "subject" refers to a mammal (e.g., human being) at any age or of any gender.

According to specific embodiments, the subject is a healthy subject.

According to specific embodiments, the subject is diagnosed with a disease or is at risk of to develop a disease.

According to specific embodiments, the subject is a donor subject (synegeneic or non-syneneic e.g., allogeneic).

According to other specific embodiments, the subject is a recipient subject.

According to specific embodiments, the T cells are obtained from a healthy subject.

According to specific embodiments, the T cells are obtained from a subject suffering from a pathology.

Thus, for example, a peripheral blood sample is collected from a subject by methods well known in the art such as drawing whole blood from the subject and collection in a container containing an anti-coagulant (e.g. heparin or citrate); and apheresis. Following, according to specific embodiments, at least one type of T cell is purified from the peripheral blood. There are several methods and reagents known to those skilled in the art for purifying T cells from whole blood such as leukapheresis, sedimentation, density gradient centrifugation (e.g. ficoll), centrifugal elutriation, fractionation, chemical lysis of e.g. red blood cells (e.g. by ACK), selection of specific cell types using cell surface markers (using e.g. FACS sorter or magnetic cell separation techniques such as are commercially available e.g. from Invitrogen, Stemcell Technologies, Cellpro, Advanced Magnetics, or Miltenyi Biotec.), and depletion of specific cell types by methods such as eradication (e.g. killing) with specific antibodies or by affinity based purification based on negative selection (using e.g. magnetic cell separation techniques, FACS sorter and/or capture ELISA labeling). Such methods are described for example in THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 2000).

According to specific embodiment, the cell culture comprises at least 50% at least 60%, at least 70%, at least 80%, at least 90% or at least 95% T cells.

According to specific embodiments, the T cells comprise more than 5%, more than 10%, more than 20%, more than 30%, more than 40%, more than 50%, more than 60%, more than 70%, more than 80%, more than 90% or more than 95% T cells with specific antigen-specificity. Thus, for examples, antigen-specific T cells can be isolated by contacting the T cells with antibodies specific for T cell activation markers.

According to specific embodiments, the T cells comprise engineered T cells transduced with a nucleic acid sequence encoding an expression product of interest.

According to specific embodiments, the expression product of interest is a T cell receptor (TCR) or a chimeric antigen receptor (CAR).

As used herein the phrase "transduced with a nucleic acid sequence encoding a TCR" or "transducing with a nucleic acid sequence encoding a TCR" refers to cloning of variable α- and β-chains from T cells with specificity against a desired antigen presented in the context of MHC. Methods of transducing with a TCR are known in the art and are disclosed e.g. in Nicholson et al. Adv Hematol. 2012; 2012:404081; Wang and Rivière Cancer Gene Ther. 2015 March; 22(2):85-94); and Lamers et al, Cancer Gene Therapy (2002) 9, 613-623.

As used herein, the phrase "transduced with a nucleic acid sequence encoding a CAR" or "transducing with a nucleic acid sequence encoding a CAR" refers to cloning of a nucleic acid sequence encoding a chimeric antigen receptor (CAR), wherein the CAR comprises an antigen recognition moiety and a T-cell activation moiety. A chimeric antigen receptor (CAR) is an artificially constructed hybrid protein or polypeptide containing an antigen binding domain of an antibody (e.g., a single chain variable fragment (scFv)) linked to T-cell signaling or T-cell activation domains. Method of transducing with a CAR are known in the art and are disclosed e.g. in Davila et al. Oncoimmunology. 2012 Dec. 1; 1(9):1577-1583; Wang and Rivière Cancer Gene Ther. 2015 March; 22(2):85-94); Maus et al. Blood. 2014 Apr. 24; 123(17):2625-35; Porter D L *The New England journal of medicine*. 2011, 365(8):725-733; Jackson H J, *Nat Rev Clin Oncol.* 2016; 13(6):370-383; Globerson-Levin et al. *Mol Ther.* 2014; 22(5):1029-1038 and in the Examples section which follows.

According to specific embodiments, the T cells are transduced with a suicide gene.

As shown in the Examples section which follows (Example 4, FIGS. 15A-G, 16A-J), in the CAR model, the effect of in-vitro activation of human HER2-CAR cells on a CCL21+ICAM1 surface was more pronounced when the cells were also produced on a coated surface as compared to when expanded on a CCL1+ICAM1 coated surface only following production.

Thus, according to an aspect of the present invention, there is provided a method of producing engineered T cells, the method comprising transducing T cells with a nucleic acid sequence encoding an expression product of interest (e.g. TCR or a CAR) in the presence of an exogenous chemokine and an exogenous adhesion molecule, thereby producing the engineered T cells.

Typically, to express an exogenous expression product of interest (e.g. TCR or CAR) in mammalian cells, the T cells are transduced with a nucleic acid expression vector (i.e. construct) encoding the expression product of interest suitable for mammalian cell expression. Such an expression vector includes a promoter sequence for directing transcription of the polynucleotide sequence in the cell in a constitutive or inducible manner. According to specific embodiments, the promoter utilized by the expression vector is active in the specific cell population transformed. Examples of cell type-specific promoters include promoters such as lymphoid specific promoters [Calame et al., (1988) Adv. Immunol. 43:235-275]; in particular promoters of T-cell receptors [Winoto et al., (1989) EMBO J. 8:729-733].

The expression vector of some embodiments of the invention includes additional sequences which render this vector suitable for replication and integration in prokaryotes, eukaryotes, or preferably both (e.g., shuttle vectors). In addition, a cloning vector may also contain a transcription and translation initiation sequence, transcription and translation terminator, a polyadenylation signal, an enhancer element, restriction element, integration element, an eukaryotic replicon and/or internal ribosome entry site (IRES). By way of example, such expression vector typically includes a 5' LTR, a tRNA binding site, a packaging signal, an origin of second-strand DNA synthesis, and a 3' LTR or a portion thereof.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A⁺, pMTO10/A⁺, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

The ability to select suitable vectors is well within the capabilities of the ordinary skilled artisan and as such no general description of selection consideration is provided herein.

According to specific embodiments, the expression vector is the retrovector pBullet/pMSGV plasmids.

Various methods can be used to introduce the expression vector of some embodiments of the invention into T cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors (e.g. adenoviruses, AAV, lentiviruses, retroviruses). In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Thus, according to specific embodiments, the transduction is effected with a viral vector (i.e. by incubating the T cells with the viral vector).

The transduction step can be effected for a couple of hours and up to a couple of days.

According to specific embodiments, the transduction is effected for at least 12 hours, at least 24 hours, at least 36 hours or at least 48 hours.

According to specific embodiments the transduction is effected for 1-3 days.

According to specific embodiments, the transduction is effected for about 2 days.

According to specific embodiments, the transduction is effected in the presence of a RetroNectin reagent (e.g. using RetroNectin coated-plates, such as commercially available from Takara Bio, Mountain View, CA, USA).

According to specific embodiments, the transduction is effected in the presence of exogenous IL-2.

According to specific embodiments, the transduction is effected on activated T cells.

According to specific embodiments, the transduction is effected on in-vitro activated T cells.

According to specific embodiments, the transduction is effected on T cells pre-cultured in the presence of a T cell stimulator, CCL21 and ICAM1, according to the present invention.

According to specific embodiments, the method of producing engineered T cells, further comprising culturing the T cells in the presence of a T cell stimulator, an exogenous chemokine and an exogenous adhesion molecule prior to the transducing.

According to specific embodiments, the culturing is effected for 1-7 days, 2-7 days, 1-5 days, 2-5 days or 1-3 days.

According to specific embodiments, the culturing is effected for about 2 days.

As noted, according to specific embodiments, the transduction is effected in the presence of an exogenous chemokine and an exogenous adhesion molecule.

As used herein the term "chemokine" refers to a chemotactic cytokine which is secreted by cells and induces direct chemotaxis of nearby responsive cells (e.g. T cells). Typically, chemokines are classified into four main subfamilies: CXC, CC, CX3C and XC. Non-limiting examples of chemokines include CCL14, CCL19, CCL20, CCL21, CCL25, CCL27, CXCL12, CXCL13, CXCL-8, CCL2, CCL3, CCL4, CCL5, CCL11 and CXCL10.

According to specific embodiments, the chemokine is CCL21.

According to specific embodiments, the chemokine is a recombinant chemokine.

According to specific embodiments, the chemokine is immobilized to a solid support.

As used herein the term "adhesion molecule" refers to a protein capable of mediating cell-cell or cell-substrate binding. In general, cell adhesion molecules are divided into two groups: molecules involved in cell-cell adhesion (i.e. intercellular adhesion) and molecules involved in cell-extracellular matrix adhesion (i.e. cell-substrate adhesion).

According to specific embodiments, the adhesion molecule is an intercellular adhesion molecule.

According to specific embodiments, the adhesion molecule belongs to the Ig (immunoglobulin) suferfamily of adhesion molecule.

Non-limiting examples of adhesion molecules include, but are not limited to, LFA-1, mac-1, CD11c/CD18, ICAM1, ICAM2, ICAM3, VCAM1, VLA1, VLA4, CD2, LFA3, CD44, CD62 (E, L and P), CD106, other integrin-family members, extracellular matrix molecules like fibronectin, and laminin, fibrinogen, and cytohesin-1.

According to specific embodiments, the adhesion molecule is ICAM1.

According to specific embodiments, the adhesion molecule is a recombinant adhesion molecule.

According to specific embodiments, the adhesion molecule is immobilized to a solid support.

Following the production of the engineered T cells, the cells may be further cultured, activated and expanded.

Thus, according to specific embodiments, the methods of the present invention further comprising culturing the engineered T cells in the presence of a T cell stimulator, an exogenous chemokine and an exogenous adhesion molecule following the transducing.

The cultures and methods of specific embodiments of the present invention comprise a T cell stimulator.

As used herein, the phrase "T cell stimulator" refers to an agent capable of activating a T cell resulting in cellular proliferation, maturation, cytokine production and/or induction of regulatory or effector functions.

Methods of evaluating T cell activation or function are well known in the art and also disclosed in the Examples section which follow and include, but are not limited to, proliferation assays such as CFSE, BRDU and thymidine incorporation, cytotoxicity assays such as chromium release and evaluating cell killing by microscopic evaluation, cytokine secretion assays such as intracellular cytokine staining, ELISPOT and ELISA, expression of activation markers such as CD25, CD69 and CD44 using flow cytometry.

The T cell stimulator can activate the T cells in an antigen-dependent or -independent (i.e. polyclonal) manner.

According to specific embodiments, the T cell stimulator is an antigen-specific stimulator.

Non-limiting examples of antigen specific T cell stimulators include antigen-loaded antigen presenting cell [APC, e.g. dendritic cell] and peptide loaded recombinant MHC.

Thus, for example, The T cells stimulator can be a dendritic cell preloaded with a desired antigen (e.g. a tumor antigen) or transfected with mRNA coding for the desired antigen.

According to specific embodiments, the antigen-specific stimulator comprises a dendritic cell loaded with the antigen.

According to specific embodiments, the antigen is a cancer antigen.

As used herein, the term "cancer antigen" refers to an antigen is overexpressed or solely expressed by a cancerous cell as compared to a non-cancerous cell. A cancer antigen may be a known cancer antigen or a new specific antigen that develops in a cancer cell (i.e. neoantigens).

Non-limiting examples for known cancer antigens include MAGE-AI, MAGE-A2, MAGE-A3, MAGE-A4, MAGE-AS, MAGE-A6, MAGE-A7, MAGE-AS, MAGE-A9, MAGE-AIO, MAGE-All, MAGE-A12, GAGE-I, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), MAGE-Cl/CT7, MAGE-C2, NY-ESO-1, LAGE-1, SSX-1, SSX-2(HOM-MEL-40), SSX-3, SSX-4, SSX-5, SCP-1 and XAGE, melanocyte differentiation antigens, p53, ras, CEA, MUCI, PMSA, PSA, tyrosinase, Melan-A, MART-I, gplOO, gp75, alphaactinin-4, Bcr-Abl fusion protein, Casp-8, beta-catenin, cdc27, cdk4, cdkn2a, coa-l, dek-can fusion protein, EF2, ETV6-AML1 fusion protein, LDLR-fucosyltransferaseAS fusion protein, HLA-A2, HLA-All, hsp70-2, KIAA0205, Mart2, Mum-2, and 3, neo-PAP, myosin class I, OS-9, pml-RAR alpha fusion protein, PTPRK, K-ras, N-ras, Triosephosphate isomerase, GnTV, Herv-K-mel, NA-88, SP17, and TRP2-Int2, (MART-I), E2A-PRL, H4-RET, IGH-IGK, MYL-RAR, Epstein Ban virus antigens, EBNA, human papillomavirus (HPV) antigens E6 and E7, TSP-180, MAGE-4, MAGE-5, MAGE-6, p185erbB2, plSOerbB-3, c-met, nm-23H1, PSA, TAG-72-4, CA 19-9, CA 72-4, CAM 17.1, NuMa, K-ras, alpha.-fetoprotein, 13HCG, BCA225, BTAA, CA 125, CA 15-3 (CA 27.29\BCAA), CA 195, CA 242, CA-50, CAM43, CD68\KP1, CO-029, FGF-5, 0250, Ga733 (EpCAM), HTgp-175, M344, MA-50, MG7-Ag, MOV18, NB\170K, NYCO-I, RCASI, SDCCAG16, TA-90 (Mac-2 binding protein\cyclophilin C-associated protein), TAAL6, TAG72, TLP, TPS, tyrosinase related proteins, TRP-1, or TRP-2.

According to specific embodiments, the tumor antigen is a HER2 peptide.

Other tumor antigens that may be expressed include out-of-frame peptide-MHC complexes generated by the non-AUG translation initiation mechanisms employed by "stressed" cancer cells (Malarkannan et al. Immunity 1999).

Other tumor antigens that may be expressed are well-known in the art (see for example W000/20581; Cancer Vaccines and Immunotherapy (2000) Eds Stern, Beverley and Carroll, Cambridge University Press, Cambridge). The sequences of these tumor antigens are readily available from public databases but are also found in WO 1992/020356 AI, WO 1994/005304 AI, WO 1994/023031 AI, WO 1995/020974 AI, WO 1995/023874 AI & WO 1996/026214 AI.

For EBV-associated lymphoma, EBV-specific antigens can be used as the cancer antigen.

Alternatively, or additionally, a tumor antigen may be identified using cancer cells obtained from the subject by e.g. biopsy. For example, a method as described herein may comprise the step of identifying a tumor antigen which is displayed by one or more cancer cells in a sample obtained from the subject.

According to specific embodiments, the T cell stimulator is an antigen non-specific stimulator.

An antigen non-specific stimulator is an agent capable of binding to a T cell surface structure and induce the polyclonal stimulation of the T cell, such as but not limited to anti-CD3 antibody in combination with a co-stimulatory protein such as anti-CD28 antibody. Other non-limiting examples include anti-CD2, anti-CD137, anti-CD134, Notch-ligands, e.g. Delta-like 1/4, Jagged1/2 either alone or in various combinations with anti-CD3. Other agents that can induce polyclonal stimulation of T cells include, but not limited to mitogens, PHA, PMA-ionomycin, CEB and CytoStim (Miltenyi Biotech).

According to specific embodiments, the antigen non-specific stimulator comprises anti-CD3 and anti-CD28 antibodies.

According to specific embodiments, the T cell stimulator comprises anti-CD3 and anti-CD28 coated beads, such as the CD3CD28 MACSiBeads obtained from Miltenyi Biotec.

Methods of determining the amount of T cell stimulator and the ratio between the T cell stimulator and the T cells are well within the capabilities of the skilled in the art and thus are not specified herein. Nonetheless, exemplary ratios are presented in the Examples section which follows.

According to specific embodiments, the cultures and the methods of the present invention further comprise an exogenous cytokine.

Thus, according to specific embodiments, the method comprises adding a cytokine to the culture.

According to specific embodiments, the cytokine is added in a level above the level obtained by culturing T cells of the same origin under the same culture conditions without addition of the cytokine.

Hence, according to specific embodiments, the cell culture comprises a cytokine in a level above the level obtained in the cell cultures described herein without addition of the cytokine.

According to specific embodiments, the cytokine is capable of inducing activation and/or proliferation of a T cell.

Non-limiting examples of cytokines that can be used according to specific embodiments of the present invention include IL-2, IL-6, IL-4, IFNα, IL-12, IFN-gamma, TNF-a, IL-15, IL-1, IL-21 and GM-CSF.

According to specific embodiments, the cytokine is IL-2.

According to specific embodiments, the concentration of IL-2 in the cultures and methods of the present invention is 10-500 U/ml, 20-200 U/ml or 30-100 U/ml.

According to specific embodiments, the cytokine is IL-6.

According to specific embodiments, the concentration of IL-6 in the cultures and methods of the present invention is 1-500 ng/ml, 5-250 ng/ml, 10-200 ng/ml or 20-100 ng/ml.

According to specific embodiments, the cytokine is not IL-6.

According to specific embodiments, the method does not comprise adding IL-6 to the culture.

According to specific embodiments, the culture does not comprise IL-6 in a level above the level obtained in the cell cultures and methods described herein without addition of IL-6.

The present inventors have shown that cytokines added to the cell cultures induce differential effects on $CD4^+$ and $CD8^+$ T cells (Table 1, in the Examples section which follows).

According to specific embodiment, the T cells comprise $CD4^+$ T cells and the cytokine is IL-6.

According to specific embodiment, the T cells comprise $CD8^+$ T cells and the cytokine is not IL-6.

According to specific embodiments, the cytokine is soluble.

According to specific embodiments, the cytokine is immobilized to a solid support.

According to specific embodiments, the cytokine is added to the culture within 24 hours of cell seeding.

According to specific embodiments, the cytokine is added to the culture at the time of cell seeding.

According to specific embodiments, the culture does not comprise more than 10, more than 8, more than 6, more than 5, or more than 4 recombinant factors.

According to specific embodiments, the T cell culture of the present invention has a morphological appearance, which can be determined by e.g. microscopic evaluation, that is characterized by at least one of:
  (i) The culture topology is a monolayer of cells;
  (ii) The T cells are elongated; demonstrating cell spreading;
  (iii) The T cells have extended and tight membrane contacts with the surface, along with peripheral interactions with neighboring cells;
  (iv) Detaching the T cells from the surface is difficult even with vigorous pipetting;
  (v) Each T cell cluster originates from multiple clones of specifically activated T-cells;
  (vi) The T cell clusters are dynamic, i.e. merging, splitting, and exchanging cells with other clusters;
  each possibility represents a separate embodiment of the present invention.

According to specific embodiments, the T cell culture of the present invention may be characterized by one, two, three, four, five or all of (i)-(vi).

According to specific embodiments, the T cell culture of the present invention is characterized by at least (i)+(ii), (ii)+(iii), (iii)+(iv), (ii)+(iii)+(iv), (v)+(vi) and/or (i)+(iv)/

According to a specific embodiment, the T cell culture of the present invention is characterized by (i)+(ii)+(iii)+(iv)+(v)+(vi).

According to specific embodiments, the microscopic evaluation is effected following labeling of the cells by e.g. a membrane-permeable dye.

According to specific embodiments, the T cell culture of the present invention presents different morphological appearance as compared to T cells of the same origin under the same culture conditions without addition of the chemokine (e.g. CCL21) and the adhesion molecule (e.g. ICAM1), wherein the combination of the chemokine (e.g. CCL21) and the adhesion molecule (e.g. ICAM1) has at least an additive effect as compared to the addition of only one of the chemokine (e.g. CCL21) and the adhesion molecule (e.g. ICAM1), as further discussed in the details in the Examples section which follows.

According to specific embodiments, the combination of the chemokine (e.g. CCL21) and the adhesion molecule (e.g. ICAM1) has a synergistic effect as compared to the addition of only one of the chemokine (e.g. CCL21) and the adhesion molecule (e.g. ICAM1).

As mentioned, the chemokine (e.g. CCL21) and the adhesion molecule (e.g. ICAM1) used in the methods of the present invention improves the in-vitro stimulation of T-cells by increasing expansion of the cells while at least maintaining their functionality.

As used herein, the term "expansion" and "proliferation" are interchangeably used and refer to an increase in the number of cells in a population by means of cell division. Methods of evaluating expansion are well known in the art and include, but not limited to, proliferation assays such as CFSE and BrDU and determining cell number by direct cell counting and microscopic evaluation.

As used herein, "increased expansion" or "increasing expansion" refers to an increase of at least 5% in T cell expansion, as compared to same in the absence of the exogenous chemokine (e.g. CCL21) and the adhesion molecule (e.g. ICAM1), as may be manifested e.g. in cell proliferation or cell number. According to a specific embodiment, the increase is in at least 10%, 20%, 30%, 40% or even higher say, 50%, 60%, 70%, 80%, 90% or more than 100%. According to specific embodiments the increase is at least 1.5 fold, at least 2 fold, at least 3 fold, at least 5 fold, at least 10 fold, or at least 20 fold as compared to same in the absence of the exogenous chemokine (e.g. CCL21) and the adhesion molecule (e.g. ICAM1).

As used herein a "functionality of a T cell" refers to the ability of a T cell to proliferate, mature, produce and/or secrete cytokine, induce regulatory functions and/or induce effector functions such as cytotoxic activity. Methods of evaluating functionality of a T cell are well known in the art and also disclosed hereinabove and in the Examples section which follow.

According to specific embodiments, the chemokine (e.g. CCL21) and the adhesion molecule (e.g. ICAM1) used in the methods of the present invention improves T cells functionality, e.g. in-vitro killing efficiency, expression of granzyme B, in-vivo activity against e.g. a tumor, wherein the combination of the chemokine (e.g. CCL21) and the adhesion molecule (e.g. ICAM1) has at least an additive effect as compared to the presence of only one of the chemokine (e.g. CCL21) and the adhesion molecule (e.g. ICAM1).

As used herein, "improves T cells functionality" refers to an increase of at least 5% in T cell function, as compared to same in the absence of the exogenous chemokine (e.g. CCL21) and the adhesion molecule (e.g. ICAM1), as may be manifested e.g. in cytokine secretion and/or cytotoxic activity. According to a specific embodiment, the increase is in at least 10%, 20%, 30%, 40% or even higher say, 50%, 60%, 70%, 80%, 90% or more than 100%. According to specific embodiments the increase is at least 1.5 fold, at least 2 fold, at least 3 fold, at least 5 fold, at least 10 fold, or at least 20 fold as compared to same in the absence of the exogenous chemokine (e.g. CCL21) and the adhesion molecule (e.g. ICAM1).

As shown in the Examples section which follows, the morphology of the cultures, T cells expansion and functionality is culture time dependent.

Thus, according to specific embodiments, the culturing is effected for 3-10, 3-7, 3-6, 4-7, 5-7, 4-6 or 5-6 days.

According to specific embodiments, the culture is up to 7 days old.

According to specific embodiments, the culture is up to 6 days old.

According to specific embodiments, the culturing is effected for at least 3 days.

According to specific embodiments, the culturing is effected for 3-7 days.

According to specific embodiments, the culturing is effected for 3-6 days.

According to a specific embodiment, the T cells are expanded by 2-200 fold following 3-7 days of culture.

Following culturing and/or transducing, a specific population of cells can be further subjected to purification. Methods of purifying a desired population of cells are well known in the art and are further described hereinabove.

Thus, according to specific embodiments, the method further comprises purifying the T cells following the culturing.

According to specific embodiments, the method further comprises purifying the T cells following the transducing.

According to specific embodiments, the T cells are purified from the T cell stimulator.

According to specific embodiments, the T cells are purified from the chemokine (e.g. CCL21) and the adhesion molecule (e.g. ICAM1).

According to specific embodiments, the specific population of T cells effective to the treatment of a disease is purified.

Thus, the present invention also contemplates isolated T cells obtainable according to the methods of the present invention.

According to specific embodiments, the cells used and/or obtained according to the present invention can be freshly isolated, stored e.g., cryopresereved (i.e. frozen) at e.g. liquid nitrogen temperature at any stage (e.g. following their retrieval, following culturing, following transduction or following purification) for long periods of time (e.g., months, years) for future use; and cell lines.

Methods of cryopreservation are commonly known by one of ordinary skill in the art and are disclosed e.g. in International Patent Application Publication Nos. WO2007054160 and WO 2001039594 and US Patent Application Publication No. US20120149108.

According to specific embodiments, the cells obtained according to the present invention can be stored in a cell bank or a depository or storage facility.

According to specific embodiments, the cells are freshly isolated (i.e., not more than 24 hours after retrieval, culturing, transduction and/or purification and not subjected to preservation processes).

Consequently, the present teachings further suggest the use of the isolated cells and the methods of the present invention for, but not limited to:
1. Pre-clinical and basic research providing a novel tool for studying e.g. the mechanisms underlying immunological processes;
2. A source for adoptive T cells therapies for e.g. malignancies, infections, autoimmune, allergies and graft rejection diseases.

Thus, according to specific embodiments, there is provided a method of adoptive T cells transfer, the method comprising administering to a subject in need thereof a therapeutically effective amount of the T cells obtainable according to the methods of the present invention, thereby adoptively transferring the T cells to the subject.

According to specific embodiments, there is provided a use of the T cells obtainable according to the methods of the present invention for the manufacture of a medicament identified for adoptive T cell therapy.

The cells used according to specific embodiments of the present invention may be autologous or non-autologous; they can be syngeneic or non-synegeneic: allogeneic or xenogeneic to the subject. Each possibility represents a separate embodiment of the present invention.

As used herein, the term "autologous" means that the donor subject is the recipient subject. Thus, in autologous transplantation the cells have been removed and re-introduced e.g., re-infused to the subject.

As used herein, the term "non-autologous" means that the donor subject is not the recipient subject.

As used herein, the term "syngeneic" means that the donor subject is essentially genetically identical with the recipient subject. Examples of syngeneic transplantation include transplantation of cells derived from the subject (also referred to in the art as "autologous"), a clone of the subject, or a homozygotic twin of the subject As used herein, the term "allogeneic" means that the donor is of the same species as the recipient, but which is substantially non-clonal with the recipient. Typically, outbred, non-zygotic twin mammals of the same species are allogeneic with each other. It will be appreciated that an allogeneic donor may be HLA identical or HLA non-identical with respect to the subject As used herein, the term "xenogeneic" means that the donor subject is from a different species relative to the recipient subject.

The term "treating" or "treatment" refers to inhibiting, preventing or arresting the development of a pathology (disease, disorder, or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

The teachings described herein are relevant for obtaining cells effective for the treatment of diseases such as, but not limited to, cancer, infectious diseases, allergies and graft rejection disease.

According to specific embodiments, the disease is cancer.

Cancers which can be treated by the method of this aspect of some embodiments of the invention can be any solid or non-solid cancer and/or cancer metastasis. Examples of cancer include but are not limited to, carcinoma, lymphoma, blastoma, sarcoma, and leukemia. More particular examples of such cancers include squamous cell cancer, lung cancer (including small-cell lung cancer, non-small-cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high-grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amenable for treatment of the invention include metastatic cancers.

According to specific embodiments the disease is an infectious disease.

As used herein, the term "infectious disease" refers to a disease induced by a pathogen. Specific examples of pathogens include, viral pathogens, bacterial pathogens e.g., intracellular mycobacterial pathogens (such as, for example, *Mycobacterium tuberculosis*), intracellular bacterial pathogens (such as, for example, *Listeria monocytogenes*), or intracellular protozoan pathogens (such as, for example, *Leishmania* and *Trypanosoma*).

Specific types of viral pathogens causing infectious diseases treatable according to the teachings of the present invention include, but are not limited to, retroviruses, circoviruses, parvoviruses, papovaviruses, adenoviruses, herpesviruses, iridoviruses, poxviruses, hepadnaviruses, picornaviruses, caliciviruses, togaviruses, flaviviruses, reoviruses, orthomyxoviruses, paramyxoviruses, rhabdoviruses, bunyaviruses, coronaviruses, arenaviruses, and filoviruses.

Specific examples of viral infections which may be treated according to the teachings of the present invention include, but are not limited to, human immunodeficiency virus (HIV)-induced acquired immunodeficiency syndrome (AIDS), influenza, rhinoviral infection, viral meningitis, Epstein-Barr virus (EBV) infection, hepatitis A, B or C virus infection, measles, papilloma virus infection/warts, cytomegalovirus (CMV) infection, Herpes simplex virus infection, yellow fever, Ebola virus infection, rabies, etc.

According to specific embodiments, the disease is an autoimmune disease. Specific examples of autoimmune diseases which may be treated according to the teachings of the present invention include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune antisperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine JC. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), Chronic obstructive pulmonary disease (COPD), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16): 660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114);

hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), Crohn's disease, ulcerative colitis, psoriasis autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

According to specific embodiments, the disease is allergy.

Specific examples of allergic diseases which may be treated according to the teachings of the present invention include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

According to other specific embodiments, the disease is a graft rejection disease.

Specific examples of graft rejection diseases which may be treated according to the teachings of the present invention include but are not limited to host vs. graft disease, chronic graft rejection, subacute graft rejection, hyperacute graft rejection, acute graft rejection, allograft rejection, xenograft rejection and graft-versus-host disease (GVHD).

As used herein, the graft may be a cell, a tissue or a whole organ graft. The origin of the graft may be embryonic, fetal, post natal or adult. Thus, the term "graft" refers to a bodily cell (e.g. a single cell or a group of cells) or tissue (e.g. solid tissues or soft tissues, which may be transplanted in full or in part). Exemplary tissues and whole organs which may be transplanted according to the present teachings include, but are not limited to, liver, pancreas, spleen, kidney, heart, lung, skin, intestine and lymphoid/hematopoietic tissues (e.g. lymph node, Peyer's patches, thymus or bone marrow). The cells may be stem cells, progenitors (e.g. immature HSCs) or differentiated cells. Exemplary cells which may be transplanted according to the present teachings include, but are not limited to, hematopoietic stem cells.

The graft can be autologous or non-autologous; it can be syngeneic or non-synegeneic: allogeneic or xenogeneic to the subject. Each possibility represents a separate embodiment of the present invention.

The graft can be autologous or non-autologous; it can be syngeneic or non-synegeneic: allogeneic or xenogeneic to the adoptively transferred T cells. Each possibility represents a separate embodiment of the present invention.

According to specific embodiments, the cells of the invention can be administered to a subject in combination with other established or experimental therapeutic regimen to treat a disease (e.g. cancer) including analgetics, chemotherapeutic agents, radiotherapeutic agents, cytotoxic therapies (conditioning), hormonal therapy and other treatment regimens (e.g., surgery) which are well known in the art.

According to specific embodiments, the T cells are transferred in a therapeutically effective amount.

According to other specific embodiments, a therapeutically effective amount means an amount of active ingredients effective to prevent, alleviate or ameliorate symptoms of a disorder or prolong the survival of the subject being treated.

Determination of a therapeutically effective amount is well within the capability of those skilled in the art, especially in light of the detailed disclosure provided herein. Dosage amount and interval may be adjusted individually to provide sufficient amount of T cells to induce or suppress the biological effect.

The amount of a T cells to be administered will, of course, be dependent on the subject being treated, the severity of the affliction, the manner of administration, the judgment of the prescribing physician, etc.

Depending on the severity and responsiveness of the condition to be treated dosing can be of a single or multiple rounds of adoptive transfer of the cells obtained according to the methods of the present invention, with course of treatment lasting from several days to several weeks or until cure is effected or diminution of the disease state is achieved.

It is appreciated that the T cells obtained via the present disclosure may be administered either alone, or as a pharmaceutical composition in combination with diluents and/or with other components such as established or experimental therapeutic regimen to treat a disease, cytokines or other cell populations. Pharmaceutical compositions of the present disclosure may comprise the T cells as described herein, in combination with one or more pharmaceutically or physiologically acceptable carriers, diluents or excipients.

According to specific embodiments, the compositions of the present invention are formulated for intravenous administration.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Mice—5-20 weeks old C57BL/6 mice were obtained from Harlan Laboratories (Rehovot, Israel) and 5-20 weeks old OT-I and OT-II mice were obtained from Jackson Laboratories (Bar Harbor, ME, USA). Mice were maintained at the Weizmann Institute's Lorry Lokey Pre-Clinical Research Facility and were cared for in accordance with national and institutional guidelines. All experiments were approved by the Institutional Animal Care and Use Committee.

Cell isolation—Spleens were harvested from the indicated mouse strain. For T-cells isolation, the spleen was cut into small 1 mm pieces, crushed and passed through 70 micron mesh and washed with PBS. Red blood cells were excluded from cell pellet by 1 minute incubation with RBC lysis solution (Biological Industries, 01-888-1B). For DCs isolation, the spleen was cut into small 1 mm pieces and incubated in spleen dissociation medium (StemCell, 079-15C) for 30 minutes, then added with 0.1M EDTA for additional 5 minutes. Following, the pieces were tcrushed and passed through 70 μm mesh and washed with PBS. Red blood cells were excluded from cell pellet by 1 minute incubation with RBC lysis solution (Biological Industries, 01-888-1B).

Naïve $CD4^+$ T cells were purified (>95%) from a cell suspension harvested from spleens of OT-II mice, using a MACS $CD4^+CD62L^+$ T Cell Isolation Kit II (Miltenyi Biotec, Bergisch Gladbach, Germany), according to the manufacturer's instructions. $CD8^+$ T cells were purified (>95%) from a cell suspension harvested from spleens of OT-I mice, using a $CD8a^+$ T Cell Isolation Kit and magnetic associated cell sorting (MACS), according to the manufacturer's instructions (Miltenyi Biotec, Bergisch Gladbach, Germany). Similarly, dendritic cells (DCs) were purified (>85%) from spleens of C57BL/6 mice, using MACS CD11c microbeads (Miltenyi Biotec).

Production of Engineered T cells (CARS)—Engineered human T cells expressing a chimeric receptor against a human HER2 protein were produced as described in Globerson-Levin et al. *Mol Ther.* 2014; 22(5):1029-1038. The culture medium used was RPMI 1640, supplemented with 10% serum, 100 U/ml of penicillin, 100 mg/ml of streptomycin, 2 mM glutamine, 1 mM sodium pyruvate, and 50 mM β-mercaptoethanol (Biological Industries, Beit Haemek, Israel).

Construction of CAR: scFvs of the anti-erbB-2 monoclonal antibody (N29) was prepared as described in Yee C. *J Transl Med.* 2005; 3(1):17; and Irvine D J, Stachowiak A N et al. Semin Immunol. 2008; 20(2):137-146. Variable fragment light (VL) chain was linked to a variable fragment heavy (VH) chain through a flexible linker. All the scFv's were ligated with the cytoplasmic domain of the co-stimulatory domain of the CD28 gene, followed by a signaling FcγR (as described in Haddad R, et al. *Biomed Res Int.* 2014; 2014:216806).

Preparation of packaging cells: The retrovector pBullet/pMSGV plasmids, expressing the anti-ErbB2 specific scFv were transfected into PG13 cells using the "ping-pong" method with a Ca2PO4 kit, MBS (mammalian transfection kit, Stratagene, La Jolla, CA), in accordance with the manufacturer's instructions.

Human T-cell isolation: Peripheral Blood Lymphocytes were isolated and frozen from donated blood units. Briefly, Blood was diluted 1:4 with PBS and 30 ml were added to 20 ml of Ficoll Paque Plus and spun down at 600G for 20 minutes at room temperature. Buffy coat ring was collected from the interface and washed with fresh medium and the cells were suspended at a concentration of $1\times10^6$/ml. For future use, the cells were suspended at a concentration of $15\times10^6$ cells in 250 μl RPMI, 250 μl fetal bovine serum and 500 μl of 20% DMSO in RPMI and frozen in at −80° C.

Coating of the pre-activation plates: non-tissue culture treated 6-wells plates (Falcon Corning, NY, NY, USA) were coated with sterile antibody solution of anti-CD3 and anti-CD28 antibodies (BioLegend, San Diego, CA, USA) at a final concentration of 1.2 μg/ml of each, with or without 5 μg/ml CCL21 (R&D Systems, Minneapolis, MN, USA) and 50 μg/ml ICAM1 (R&D) and incubated over night at 4° C.

Pre-activation of T cells: The coating solution was removed from the activation plates and immediately replaced with a 1 ml of 1% BSA blocking solution for 20-60 minutes at room temperature. Plates were then washed with 3 ml PBS and seeded with $4\times10^6$ freshly isolated T cells or $8\times10^6$ defrosted T cells and incubated for 48 hours at 5% $CO_2$ at 37° C.

Coating of the transduction plates: non-tissue culture treated 6-wells plates (Falcon Corning) were coated overnight at 4° C. with 48 μg/ml RetroNectin (Takara Bio, Mountain View, CA, USA) with or without 5 μg/ml CCL21 and 50 μg/ml ICAM1 (R&D).

Loading of the retroviral vector on the transduction plates: The coating solution was removed from the transduction plates and immediately replaced with a 1 ml of 1% BSA blocking solution for 20-60 minutes at room temperature. Plates were then washed with 3 ml PBS and immediately added with 2 ml of filtered retroviral vector-containing supernatant (from 70% confluent culture of packaging cells), with 100 U/ml of FDA approved human IL-2 (Proleukin, Novartis); and incubated for 30 minutes at 7.5% $CO_2$ at 37° C.

Retroviral transduction of T cells was performed as described in Haddad R, et al. *Biomed Res Int.* 2014; 2014:216806. Briefly, the pre-activated T cells were collected, washed and counted. $3\times10^6$ cells were resuspended in 1 ml of filtered retroviral vector-containing supernatant (from 70% confluent culture of packaging cells), with 100 U/ml of FDA approved IL-2 and added to the transduction plates for 6 hours at 7.5% $CO_2$ 37° C. Supernatant from wells was then collected into tubes and 1 ml culture medium containing 100 U/ml human IL-2 was added to the each well. The collected supernatant was spun down, re-suspended in 2 ml culture medium containing 100 U/ml human IL-2 and added back into the same transduction plate for a recovery of overnight incubation at 7.5% $CO_2$ at 37° C. On the next day, cells were collected, spun down, and underwent a second similar round of retroviral transduction and recovery on freshly coated and virus-loaded plates as described above.

Expansion: Following transduction, cells were collected, spun down and suspended at a concentration of $0.5\times10^6$/ml in fresh medium RPMI 1640 medium containing 300 U/ml of human IL-2 and cultured for 3-6 days on un-coated plates or on plates pre-coated with CCL21 and ICAM1 as described above.

Culture conditions—Culture plates [24/96/384-wells plates (Nunc/Costar cell culture treated plates)] were pre-coated by overnight incubation in PBS (control) or PBS with 5 μg/ml CCL21 (R&D Systems, Minneapolis, MN, USA), 50 μg/ml ICAM1 (R&D Systems) and/or 20 μg/ml anti-LFA1 (Leaf-aCD11a; BioLegend, San Diego, CA, USA). For SEM/TEM microscopic evaluations, glass coverslips were placed inside the wells prior treatment. Following, plates were washed with PBS. Following, the isolated cells were seeded at the indicated concentration (between 3250-$10^6$ cells/ml) on the culture plates in complete RPMI 1640 medium [RPMI 1640 w/o phenol red, supplemented with 10% serum, 100 U/ml penicillin, 100 mg/ml streptomycin, 2 mM glutamine, 10 mM HEPES, 1 mM sodium pyruvate, 50 mM β-mercaptoethanol (Biological Industries, Beit Haemek, Israel] containing 1 μg/ml ovalbumin peptide (OVA323-339, InvivoGen, San Diego, CA, USA) and cultured for 24 hours to 7 days in 37° C., 5% $CO_2$. An illustration of the model is shown in FIG. 1R. At the indicated cases, the T cells were activated for 24 hours with antigen-loaded DCs and then reseeded on different surface coatings for an additional incubation time (e.g. 48 hours). When T cells activation was effected using DCs, the freshly isolated T cells and DCs were seeded in a ratio of 3:1, respectively. When CD3/CD28 beads were used for activation, the freshly isolated T cells were incubated 1:1 with activation beads freshly prepared according to manufacturer's instruction (Miltenyi Biotec, Bergisch Gladbach, Germany) and IL-2 30 Units/ml (BioLegend, San Diego, CA, USA). When indicated, 20-100 ng/ml of soluble IL-6 (BioLegend) and/or 2-200 ng/ml of soluble IL-2, IL-12, IL-7, TNF-α, IFNγ, TGF-β, IL-4 and/or GM-CSF (all from BioLegend) were added to the culture media. For blocking LFA1 in culture media, 5 μg/ml of blocking antibody was added 24 hours following cell seeding. For evaluating confinement to surface functionalized areas, SILICON Polydimethylsiloxane (PDMS) [Ibidi, Ltd (Germany)] molds containing 4 separate, bottomless chambers were placed on a 35 mm glass-bottomed dish (MatTek) as shown in FIG. 4A. Different coating solutions were placed in each chamber, to form separate strips containing: no coating, ICAM1 coating, CCL21 coating, and CCL21+ICAM1 coating on the glass surface. Following overnight incubation, the coating solutions and SILICON molds were removed and the surfaces were thoroughly rinsed. OT-II CD4+ T cells were then co-cultured with ovalbumin-loaded DCs and imaged by phase contrast microscopy at the indicated time points.

Labeling with membrane permeable dyes—Prior to seeding, naïve CD4+ T cells were labeled with either 10 µM CPDE-450 (Cell Proliferation Dye eFluor-450), 5 µM CPDE-670 (eBioscience, San Diego, CA, USA) or 2 µM CFSE (Invitrogen, Carlsbad, CA, USA) for 10 minutes at 37° C. Excess dye was removed by three cold washes with 7 volumes of RPMI 1640, prior to cell seeding.

Cell proliferation assay—T cells were stained prior to seeding according to manufacturer's instructions with 5 µM CFSE (Biolegend) for 20 minutes or with 10 µM CPDE-450 (Cell Proliferation Dye eFluor-450; eBioscience, San Diego, CA, USA) for 10 minutes at 37° C. Excess dye was removed by washing with 5-7 volumes of RPMI 1640. Following, $90 \times 10^3$ T cells were seeded with $30 \times 10^3$ DCs in a 96 wells plate with 250 µl complete RPMI 1640 medium containing 1 µg/ml ovalbumin peptide. Five days later, cells were detached from the surface by 10 minutes incubation with PBS without calcium and magnesium, and pipetting. Propidium iodide (PI) 1 µg/ml was added to each well for cell death staining and the single cell suspensions were analyzed by flow cytometry (BD Bioscoence and the software analysis FlowJo, Ashland, OR, USA). Since CFSE is diluted by approximately half with each cell division, live single cells (PI negative cells) were gated and the mean fluorescent intensity of CFSE was used to evaluate the level of proliferation.

Cell viability assays—A microscopic viability assay was performed by staining the cell nuclei with 1 µg/ml Hoechst (33342, ImmunoChemistry Technologies, Bloomington, MN, USA) and with 250 ng/ml propidium iodide (PI, Sigma Aldrich, St. Louis, MO, USA), for identification of dead cells. Cells were pipetted in order to breakdown clusters and spun down. Fluorescent images were taken using a Hermes microscope (IDEA Bio-Medical Ltd.) and the image analysis software (WiSoft, IDEA Bio-Medical Ltd.) was used to quantify viable cell numbers. A metabolic viability assay was performed by adding 20 µl CellTiter-Blue (Promega Corporation, Madison, WI, USA) per 100 µl culture medium for 3 hours. Results were quantified using a fluorescent plate reader (excitation 560 nm; emission 590 nm), and a linear equation of a calibration column, according to manufacturer's instructions.

Live staining of T cells for culture height measurements—For measuring culture height using Z-stack imaging, 5 µg/ml of anti-CD44 (stains activated T cell, BioLegend) and 10 mM CyTRACK Orange (eBioscience, San Diego, CA, USA) were gently added to the culture medium of each well, so not to disturb cell contacts and structures. Cells were incubated for one hour prior to Z-stack imaging using a DeltaVision Elite® microscope (Applied Precision, GE Healthcare, Issaquah, WA, USA) mounted on an inverted IX71 microscope (Olympus, Center Valley, PA, USA) connected to a Photometrics CoolSNAP HQ2 camera (Roper Scientific, Martinsried, Germany). The primary image processing software used was SoftWorX 6.0. This microscope was also used for the production of deconvolution-based 3D.

Microscopy and image analysis—Wide-range phase-contrast images were acquired and stitched, using the 30/× objective of a Ti-eclipse microscope (Nikon Instruments, Konan, Minato-ku, Tokyo, Japan) equipped with an automated stage, and an incubator with a 5% $CO_2$ atmosphere. Time-lapse movies were acquired using a DeltaVision Elite® microscope (Applied Precision, GE Healthcare, Issaquah, WA, USA) mounted on an inverted IX71 microscope (Olympus, Center Valley, PA, USA) connected to a Photometrics CoolSNAP HQ2 camera (Roper Scientific, Martinsried, Germany). The primary image processing software used was SoftWorX 6.0. This microscope was also used for the production of deconvolution-based 3D image reconstructions, rendering supported by BITPlan software (Willich-Schiefbahn, Germany). Wide-range phase-contrast images and high content/high throughput microscopy was conducted on 96-wells plates using a Hermes® microscope (IDEA BioMedical Ltd., Rehovot, Israel) equipped with automated scanning optics, high-precision autofocus, and a closed environmental chamber. The WiSoft® software (IDEA Bio-Medical Ltd.) was utilized for cell counting and cell death analysis. Cluster analysis was carried out using Fiji software: Background was subtracted by means of a rolling ball method, and textured cluster areas were enhanced by a standard deviation filter, prior to thresholding using fixed value. Morphological filtering was applied to fill holes and connect broken clusters; finally, single cells were discarded by size and circularity. Areas of individual clusters and the total area of all clusters in a given image were measured for each condition.

Scanning electronic microscopy—In assays evaluating CD4+ T cells: T cells were seeded and activated as described above on glass coverslips placed inside wells of a 24-wells plate for 72 hours. In assays evaluating CD8+ T cells: T cells were seeded and activated as described above on glass coverslips placed inside wells of a 24-wells plate for 7-9 days, harvested and counted; in the next step, target cells were seeded on glass coverslips placed inside wells of a 24-well plate (250,000/well) with the harvested CD8+ T cells (750,000/well) for 16-24 hours. Following, wells were gently washed in 0.1 M cacodylate buffer, fixed with Karnovsky fixative (2% glutaraldehyde, 3% PFA, in 0.1 M cacodylate buffer) and incubated overnight at 4° C. Coverslips were dehydrated in increasing concentrations of ethanol (30%, 50%, 70%, 96% and 100%) followed by critical-point drying in BAL-TEC CPD030, and sputtering in a gold palladium sputter coater (Edwards, Crawley, UK). Images were taken using a secondary electron (SE) detector in a high-resolution Ultra 55 scanning electron microscope (Zeiss, Oberkochen, Germany).

Transmission electron microscopy—Cells were seeded as described above on glass coverslips placed inside wells of a 24-wells plate. Following 72 hours, cells were fixed in Karnovsky fixative for 2.5 hours at room temperature and washed 4 times with 0.1M cacodylate buffer. Samples were then post-fixed for 1 hour in 1% $OsO_4$, 0.5% $K_2Cr_2O_7$, and 0.5% $K_4[Fe(CN)_6]3H_2O$ in 0.1 M cacodylate buffer; and washed three times in double-distilled water (DDW), followed by 1 hour incubation with uranyl acetate (2% in DDW). Following, samples were washed with DDW, and dehydrated in increasing concentrations of ethanol (30%, 50%, 70%, 96% and 100%). Epon ["hard", EMS (electron microscopy sciences) Ltd.] was gradually infiltrated into the cultures in increasing concentrations (30%, 50%, and 70% in propylene oxide) for 2 hours each and then with 100% Epon for 16 hours following by 100% Epon for three times for 2 hours each. In the next step, samples were transferred in Epon to backing molds, and baked overnight in an oven. The Epon blocks were disconnected from the coverslip by cooling using liquid nitrogen followed by heating with a hot plate. Finally, 70-100 nm ultra-thin slices were cut and stained with uranyl acetate 2% in ethanol and lead citrate. Grids were analyzed in a CM-12 Spirit FEI electron microscope; images were taken with an Eagle 2k×2k FEI (Eindhoven, Netherlands).

CD4+ T cells Sub-differentiations induction—The following differentiation cytokines and neutralizing antibodies were added to the culture media upon cell seeding: for Th1 differentiation IL-12 (10 ng/ml)+anti-IL-4 (10 μg/ml); for Th2 differentiation IL-4 (20 ng/ml)+anti-IFNγ (10 μg/ml)+anti-IL-12 (10 μg/ml); for Treg differentiation TGFβ (10 ng/ml)+IL-2 (5 ng/ml)+anti-IL-4 (10 μg/ml)+anti-IFNγ (10 μg/ml)+anti-IL-12 (10 μg/ml). Following 5 days of culturing as described above, cells were fixated, permbealized, stained with anti-CD4 and anti-Tbet for Th1, anti-GATA3 for Th2, and anti-Foxp3 for Tregs and analyzed by flow cytometry analysis (BD Biosciense and Flowjo). All cytokines and antibodies were obtained from BioLegend.

Re-stimulation and IFNγ analysis—CD4+ T cells were activated and induced to sub-differentiate to Th1 as described above. Following 7 days of incubation, cells were spun down and the medium was replaced with a medium containing PMA and ionomycin (BioLegend, BLG-423301, 1:500) for 4 hours of re-stimulation. Brefeldin (BioLegend, BLG420601) and Monensin (BioLegend, BLG420701) were then added 1:1000 each for 2 hours, for prevention of proteins secretion. Following, cells were collected, fixated, permeablized, stained with anti-CD4 and anti-IFNγ (BioLegend) and analyzed by flow cytometry analysis (BD Biosciense and Flowjo).

In-vitro cytotoxic murine T cells killing assay—B16 cells expressing ovalbumin coupled with GFP (Tali Feferman et al. Imaging regulatory mechanisms that limit intratumoral CTL function in a mouse melanoma model. [abstract]. In: Proceedings of the AACR Special Conference: Tumor Immunology and Immunotherapy: A New Chapter; Dec. 1-4, 2014; Orlando, FL. Philadelphia (PA): AACR; Cancer Immunol Res 2015; 3(10 Suppl): Abstract nr B06) were suspended in a RPMI 1640 complete medium [RPMI 1640 w/o phenol red, supplemented with 10% serum, 100 U/ml of penicillin, 100 mg/ml of streptomycin, 2 mM glutamine, 10 mM HEPES, 1 mM sodium pyruvate, and 50 mM β-mercaptoethanol (Biological Industries, Beit Haemek, Israel)], seeded 1000 cells per 384-plate well, and incubated for 2-3 hours to allow attachment to the surface. OT-I CD8+ T cells activated and cultured for 3 or 7 days as described above, were then added on top of the B16 cells. The entire well was imaged every 6 hours using Hermes® microscope (IDEA BioMedical Ltd., Rehovot, Israel) equipped with automated scanning optics, high precision autofocus and a closed environmental chamber. The number of live (e.g. GFP expressing) B16 cells was counted from the image analysis using the WiSoft® software (IDEA Bio-Medical Ltd.).

In-vivo cytotoxic T cells tumor suppression assay—B16 melanoma cell line expressing ovalbumin (a courtesy of the Lea Eisenach laboratory at the Weizmann institute) were grown in DMEM complete medium [DMEM supplemented with 10% serum, 100 U/ml of penicillin, 100 mg/ml of streptomycin, 2 mM glutamine, 10 m M HEPES, 1 mM sodium pyruvate, and 50 mM β-mercaptoethanol (Biological Industries, Beit Haemek, Israel)]. Cells were harvested using trypsin and washed twice and suspended in PBS (Biological Industries). For each C57BL/6 mouse, 50 μl of cell suspension containing $2\times10^6$ cells was injected or topically into the flank skin. Seven days following the injection of the tumor line cells, tumor size was documented by measuring with a caliper the two longest vertical diameters of the tumor. The multiplication of these diameters was used to exclude mice bearing tumors with smaller than 15 mm$^2$ or larger than 35 mm$^2$. The rest were split into groups with similar average and size distribution. OT-I CD8+ T cells activated and cultured for 8-9 days as described above, were washed twice and suspended in PBS. For each tumor bearing C57BL/6 mouse, 100 μl containing $2\times10^6$ or $4\times10^6$ CD8+ T cells were injected intravenously. Three days following T cell injection, and every 2-3 days onward, tumor size was documented by measuring with a caliper the two longest vertical diameters of the tumor. The average of these two diameters (D) was used to calculate the volume of a ball with the following formula—$4/3\times\pi\times(D/2)^3$.

In-vitro cytotoxic human HER2-CAR T cells killing assay—Renca (murine renal adenocarcinoma cell line) cells, which express human HER2/ErbB2 (human epidermal growth factor receptor 2) coupled with Luciferase and Neomycin resistance (Maurer-Gebhard et al. CANCER RESEARCH (1998) 58: 2661-2666) were suspended in a RPMI 1640 complete medium without phenol red, supplemented with 10% serum, 0.48 mg/ml G418, 100 U/ml of penicillin, 100 mg/ml of streptomycin, 2 mM glutamine, 10 mM HEPES, 1 mM sodium pyruvate, and 50 mM β-mercaptoethanol, (Biological Industries, Beit Haemek, Israel). The cells were seeded 50,000 cells per 96-wells plate and co-cultured with 150,000 human CD8+ T cells (3:1 T cell:target) of which 40-60% were HER2-CAR cells (3 or 6 days following retroviral transduction). The following day, 150 μg/ml final concentration of Luciferin (Promega, Madison, WI, US) was added to each well and luminescence (total photon flux/sec) was measured every few hours using the IVIS 100 Imaging System (Xenogen, Alameda, CA, US).

Example 1

CCL21 and ICAM1 have a Combined Improved Effect on In-Vitro Expantion of CD4+ T Cells In-Vitro Activation of CD4+ T Cells with Antigen Loaded DCs on a CCL21 Coated Surface Increases the Number and Size of T Cell Clusters CD4+ T cells expressing ovalbumin-specific T cell receptors, isolated from TCR transgenic OT-II mice and stimulated with dendritic cells (DCs) loaded with the corresponding cognate ovalbumin peptide were used as a model for antigen-specific T cell stimulation. To distinguish between the two cell types in the culture, the DCs and the T cells were pre-labeled with different cell-permeable dyes. As shown in FIGS. 1A-B and 1D-E, cell clusters formed following stimulation consisted mainly of proliferating CD4+ T cells with only 1-2 DCs per cluster, most of which were dead following 24 hours of culture. Dynamic morphometry indicated that the T cell clusters continuously expanded in size for ~120 hours (FIGS. 1G-H and 1Q); and from that point onwards, they disassembled dramatically, and scattered into single cells. Notably, a similar phenomenon is also observed in the natural niche, when T cells detach from the clusters, leave the lymph node, and translocate into the circulation.[42]

Importantly, activating the T cells on CCL21-coated surfaces induced a major increase in cluster size as compared to activation on uncoated surfaces, as demonstrated using a combination of imaging tools such as light microscopy and scanning electron microscopy (FIGS. 1A-H, 1Q, 2A-B and 2G-H). Comparing between T cell clusters formed on CCL21-coated and uncoated surfaces indicated that CCL21 induced a greater than 2-fold increase in the number of clusters formed (FIG. 1G) and more than a 5-fold increase in cluster projected area (FIG. 1H). To examine the cellular clonality of these large CCL21-induced clusters, equal numbers of OT-II CD4+ T cells were pre-labeled with 3 different dyes, mixed and activated with antigen-loaded DCs on a CCL21-coated surface. The individual clusters were subjected to 3D deconvolution-based fluorescence imaging. As shown in FIGS. 1I-J, all clusters contained cells labeled with all three dyes, confirming that they were formed by a merger of multiple T cell clones. Live-cell imaging further demonstrated that the clusters were highly dynamic; they changed in size following cell proliferation and by merger or splitting of clusters (see FIGS. 1K-P). Further experiments indicated that the cell-cell interactions induced by the immobilized CCL21 are LFA1-dependent, since the formation of large clusters was dramatically reduced by adding an anti-LFA1 blocking antibody to the culture (FIG. 2F). In addition, transmission electron microscopy images revealed that T cells within the large clusters are loosely packed, despite multiple filopodia-mediated contacts between them (FIGS. 3A-C). Comparative 3D imaging of T cells (FIGS. 3I-M), showed that clusters forming on the CCL21-coated surface were significantly thicker (h=26 µm, on average), compared to those forming on the uncoated surface (h=16 µm).

Notably, the formation of large T cell clusters driven by CCL21 coating could potentially exert either beneficial or detrimental effects on T cell activation. On the one hand, clustering may support the activation of many T cells by a small number of DCs, as well as the interplay between T cells residing within the same cluster. Clustered T cells secrete various regulatory factors with autocrine and paracrine activity, and the close proximity of cells within the cluster facilitates intercellular communication in a regulated microenvironment. [3,40,43-45] On the other hand, large T cell clusters may limit or even down-regulate T cell proliferation, by restricting the cells' access to essential signals or nutrients, or even by creating inhibitory environmental conditions. As CCL21 coating induced the formation of very large, yet short-lived 3-dimensional clusters, it was assumed that the conditions within these clusters might be less favorable.

In-Vitro Activation of CD4$^+$ T Cells with Antigen Loaded DCs on a Coated ICAM1 Surface Transforms T Cell Clusters into Substrate-Attached Monolayers Using the same antigen-specific T cell stimulation model described above, the effect of coating the surface with the adhesion molecule ICAM1 was evaluated.

Light and electron microscopy revealed a major morphological transformation of CD4$^+$ T cells plated on the ICAM1 coated surface. Specifically, as shown in FIGS. 2A-J, in contrast with the clusters formed on either uncoated or CCL21-coated surfaces, T cells activated on an ICAM1-coated surface alone or on a CCL21-ICAM1 coated surface formed 2D monolayers of flat cells. Notably, cultures on ICAM1 coated surface without CCL21, contained lower cell densities as compared to CCL21+ICAM1. Coating the surface with ICAM1 and CCL21 also exerted a strong effect on the morphology of single T cells (FIGS. 2G-J): cells interacting with uncoated surfaces were mostly round, with hardly any stable cell contacts while on the CCL21 coated surface, they developed an elongated morphology; in addition, ICAM1 coating, with or without CCL21, induced massive cell spreading on the surface, and multiple cell-cell contacts, some by means of long, thin tethers. Transmission electron microscopy images revealed that following CD4$^+$ T cells activation on a CCL21+ICAM1-coated surface, cells spread and formed extended and tight membrane contacts with the surface, along with peripheral interactions with neighboring cells (FIGS. 3D-H) compared to the T cells within the large clusters formed on CCL21-coated surface which were loosely packed, despite multiple filopodia-mediated contacts between them (FIG. 3A-C). Notably, while T cell clusters on uncoated or CCL21-coated surfaces were loosely attached to each other and to the culture substrate and could be easily displaced by gentle mechanical perturbation, detaching the cells from the ICAM1-coated surface was difficult even with vigorous pipetting. This demonstrates that surface-bound ICAM1 formed tighter, more stable contacts with cellular LFA1 compared to intercellular ICAM1-LFA1 interactions, and might thus reinforce and sustain the cells' interactions with the stimulatory, substrate-bound CCL21.

Comparative 3D imaging of T cells (FIGS. 3I-M), further showed that clusters forming on the dual CCL21+ICAM1 coating surface became thinner (h=11 µm), and even thinner still (h=7 µm) when ICAM1 alone was used, as compared to clusters forming on the CCL21-coated surface (h=26 µm, on average) or those forming on the uncoated surface (h=16 µm).

Culturing cells on a patterned surface characterized by separate uncoated areas and areas coated with ICAM1-1, CCL21 or both, verified that the observed differences in T cell clustering, cell spreading and cell density are indeed local, confined to the coated area, and unaffected by both the relative order of the coatings on the surface, as well as by the number of seeded cells (FIGS. 4A-E). Specifically, T cells were found mainly within the coated areas, which display a higher cell density compared to that of the uncoated area; the induction of large clusters by CCL21 coating and the cell spreading and culture flattening induced by ICAM1 were confined to the coated area and did not affect the morphology of T cells in other areas that share the same original cell pool and culture medium.

Taken together, these findings confirm that ICAM1 drives T cells adhesion to the surface and can effectively compete with their ability to cluster with each other.

In-Vitro Activation of CD4$^+$ T Cells with Antigen Loaded DCs on a Coated CCL21 and ICAM1 Surface Improves Antigen-Specific T Cells' Expansion The impact of the surface coating on CD4$^+$ T cells was not limited to morphological rearrangement, but also exerted a major effect on T cells yield. To quantify this effect, nuclear staining and automated image analysis was used to count the number of viable cells at different time points during culture analysis. A shown in FIGS. 5A-I, cell numbers in the cultures coated with either CCL21 alone or ICAM1 alone were up to 2-fold greater than cell numbers in cultures on uncoated surfaces (FIG. 5I). When CCL21 and ICAM1 were combined, the increase in cell number rose to 4.5-fold at 7 days (FIG. 5I) and was restricted to antigen-specific activated T cells. This effect was also demonstrated by image quantification of OT-II-GFP-expressing cells that were mixed with unstained non-ova T cells at a ratio of 1:99 (FIG. 5J-M). OT-II CD4$^+$ T cells expanded more than 8-fold on uncoated surfaces, and over 16-fold on surfaces coated with CCL21+ICAM1, following 7 days in culture (FIG. 5L), while the vast majority of non-ova T cells died (FIG. 5M).

To determine whether the increase in viable cells number on the double-coated surface was merely the result of geometrical changes and physical tethering of the cells to the surface, T cell adhesion and expansion on a surface coated with anti-LFA1 blocking antibodies was examined. In this experimental setting, OT-II CD4$^+$ T cells were activated for 24 hours with antigen-loaded DCs and only then reseeded on different surface coatings for additional 48 hours. Similarly to findings on the ICAM1 coating, the immobilized anti-LFA1 mediated T cell binding to the surface via the LFA1 receptor (FIGS. 6A-C). Nevertheless, despite similar degrees of cell spreading and attachment to the surface through the LFA1 T cell receptor, there was no apparent increase in cell expansion in these cultures, suggesting that stimulation of cell proliferation is not driven merely by adhesion to the substrate and reduction of the clusters per se, but rather depends on genuine ICAM1-LFA1 interactions (FIG. 6D). It should be noted that the effects of surface coatings on T cells are direct and not mediated by the DCs, since when the cells were transferred to the coated surface (at the 24 hours time point) the vast majority of the DCs were already dead (data not shown).

Finally, the possibility of further augmenting cell number by means of selected cytokines added to the culture medium at a wide range of concentrations was evaluated. The tested cytokines included: IL-2, IL-12, IL-6, IL-7, TNF-α, IFNγ, TGF-β, IL-4 and GM-CSF. Most of the cytokines tested had no significant effect on T cell expansion, either alone, or in combination with CCL21 and/or ICAM1 coatings (data not shown). However, as shown in FIG. 7A-H, IL-6 decreased the percentage of dead cells by nearly a factor of 2 on uncoated surfaces and increased expansion by over 3-fold. More importantly, this increase induced by IL-6 was greatly enhanced when cells were seeded on CCL21+ICAM1 coated surfaces, yielding an up to 8-fold increase in the number of viable T cells at 7 days, compared to the culturing on uncoated surface, and up to a 1.6-fold increase, compared to culturing on CCL21+ICAM1 coated surface. Notably, CFSE staining of cells prior to seeding and flow cytometry analysis, demonstrated that the contribution of CCL21+ICAM1 coating to cell yield was mediated primarily through increased proliferation, as demonstrated by a nearly 4-fold decrease in florescent intensity of CFSE, compared to the uncoated cultures (FIGS. 7G-H).

In-Vitro Activation of CD4+ T Cells with Non-Specific CD3 Anti-CD28 Coated Beads on a Coated CCL21 and ICAM1 Surface Improves T Cells' Expansion The antigen-loaded DCs were chosen as the primary model for T cell activation, as this model has several important advantages over activation with non-specific activation using e.g. commercially available anti-CD3 anti-CD28 coated beads. In addition to being a more native, antigen-specific and less artificial form of activation, activation with DCs was found to provide a greater T cell yield while requiring a minimal number of T cells, smaller by 7-fold than that needed with beads (FIGS. 8A-E). However, Similarly to DCs activation, T cells activation with beads on CCL21+ICAM1 coated surface significantly augmented T cell proliferation and yield (FIGS. 8A-G) compared to activation on an uncoated surface, indicating surface-bound CCL21 and ICAM1 has a synergistic effect on T cells' expansion with other forms of activation.

In-Vitro Activation of CD4+ T Cells on a Coated CCL21 and ICAM1 Surface Does Not Affect CD4+ T Cell Sub-Differentiation and Function As shown in FIGS. 9A-D, in-vitro activation of CD4+ T cells with DCs or with anti-CD3 anti-CD28 coated beads on a CCL21-ICAM1 coated surface did not significantly affect the proportions of sub-differentiations to Th1, Th2 or Tregs. In addition, following re-stimulation with or without induction of Th1, cells grown on CCL21+ICAM1 coated surfaces secreted similar amounts of IFNγ.

Example 2

CCL21 and ICAM1 have a Combined Improved Effect on In-Vitro Expantion of CD8+ Cytotoxic T Cells CD8+ T cells expressing ovalbumin-specific T cell receptors, isolated from TCR transgenic OT-I mice and stimulated with dendritic cells (DCs) loaded with the corresponding cognate ovalbumin peptide were used as a model for antigen-specific T cell stimulation.

Figure 10A:
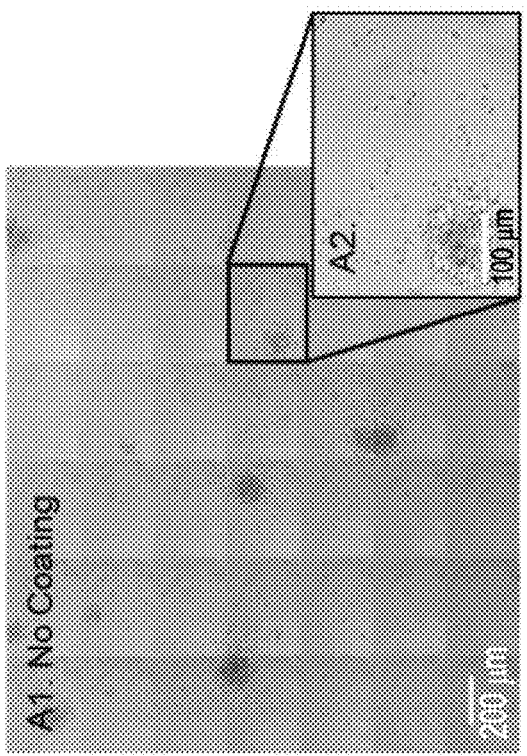
Figure 10C:
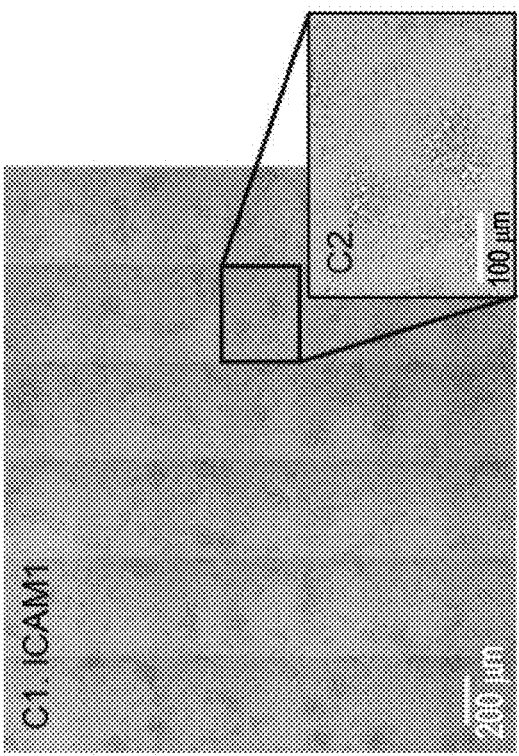

In-Vitro Activation of CD8+ T Cells with Antigen Loaded DCs on a CCL21 Coated Surface Increases the Size of T Cell Clusters while Activation on an ICAM1 Coated Surface Transforms the Clusters into Substrate-Attached Monolayers The effect of coating the culture surface with CCL21 and/or ICAM1 had a similar effect on the topology of CD8+ T cells culture as it did on CD4+ T cells culture (FIGS. 10A-D). Specifically, in-vitro activation of OT-I CD8+ T cells with antigen loaded DCs on a CCL21 coated surface induced large CD8+ T cell clusters (FIG. 10B) compared the activation on an uncoated surface (FIG. 10A); CD8+ T cells activation in-vitro on an ICAM1 coated surface or on a CCL21+ICAM1-coated surface (FIGS. 10C-D) formed 2D monolayers of spread cells; and in addition cultures on ICAM1 alone, without CCL21, contained lower cell densities. Notably, the T cells were firmly attached to the ICAM1 coated surface and detaching them was difficult, even with vigorous pipetting, while clusters on uncoated or CCL21 only coated surfaces were easily scattered.

In-Vitro Activation of CD8+ T Cells with Antigen Loaded DCs on a Coated CCL21 and ICAM1 Surface Improves Antigen-Specific T Cells' Expansion Surface-immobilized CCL21+ICAM1 did not only alter cell organization and culture topology of CD8+ T cells, but also exerted a major effect on T cell yield. This effect was quantified with nuclear staining and automated image analysis used to count the number of viable cells. Representative images (FIGS. 11A-H) as well as image analysis quantification of viable cell numbers (FIGS. 11I and 11K) and percentage of cell death (FIGS. 11J and 11L), revealed that in-vitro activation on a CCL21+ICAM1 coated surface approximately doubled viable CD8+ T cell numbers, compared to activation on an uncoated surface (FIGS. 11I and 11K). Hence, similarly to CD4+ T cells, CCL21+ICAM1 had an effect on CD8+ in-vitro activation. In addition; and similarly to the results with the CD4+ T cells; CCL21+ICAM1 effect was a result of augmenting CD8+ T cells proliferation rather than cell survival (FIGS. 11J and 11L). Furthermore, addition of soluble IL-6, collectively with CCL21+ICAM1, increased viable CD8+ T cell numbers by up to 7 times at 72 hours and 12 times at 7 days of culture, as compared to activation on an uncoated surface with no IL-6 (FIGS. 11I and 11K), possibly by decreasing the percentage of dead T cells by up to 25% and 55%, respectively (FIGS. 11J and 11L). These findings, correlating with the effect of IL-6 on CD4+ T cells suggests that combining soluble IL-6 with surface bound CCL21+ICAM1 significantly improves the expansion and cell survival of both CD4+ and CD8+ T cells.

Interestingly, in-vitro activation of the cells on the ICAM1 coated surface and on the CCL21+ICAM1 coated surface had an even greater effect on cell density in the culture, when the number of CD8+ T cells seeded was extremely low (FIGS. 11P-U). Thus, for instance, when seeding just 750 cells per well (7500 cells/ml), only few small clusters were visible in the uncoated well, while the ICAM1 coated well had demonstrated a relatively high density and spread culture; and an even denser culture, with a few spread clusters was evident in the CCL21+ICAM1 coated well. Since T cell survival is often dependent on stimulatory paracrine signals from other adjacent T cells, they are hard to expand when starting from a low number of cells. Thus, this effect of ICAM1 could be extremely helpful for instance, when only a low number of tumor infiltrating T cells are isolated from a given tumor for adoptive cell therapy.

In-Vitro Activation of CD8⁺ T Cells with Non-Specific CD3 Anti-CD28 Coated Beads on a Coated CCL21 and ICAM1 Improves T Cells' Expansion Activation of the CD8⁺ cells with commercially available anti-CD3 anti-CD28 coated beads, was found to provide significantly less T cells as compared to activation with antigen-loaded DCs (FIG. 11M). However, similarly to DCs activation, T cells activation with beads on CCL21+ICAM1 coated surface significantly augmented T cell proliferation and yield (FIGS. 11M-O) compared to activation on an uncoated surface.

Example 3

CCL21 and ICAM1 During In-Vitro Activation of CD8⁺ T Cells have a Combined Improved Effect of the Cells In-Vitro and In-Vivo Cytotoxic Efficiency In-Vitro Activation of CD8⁺ T Cells with Antigen Loaded DCs on a Coated CCL21 and ICAM1 Surface Improves the Cells In-Vitro Killing Efficiency Given the effect of CCL21+ICAM1 for increasing T cells yield and use in adoptive therapy, in the next step the yielded pool was evaluated for functional activity. To this end, a microscopic killing assay was established, comprising co-cultures of B16 target cells, expressing ovalbumin coupled with GFP and OT-I CD8⁺ T cells pre-cultured on an uncoated surface or on a surface coated with CCL21+ ICAM1. Following, the number of live (e.g. GFP expressing) B16 cells was counted from the image analysis of each entire well of the co-cultures and used to assess the killing efficiency of the T cells.

As shown in FIGS. 12A-J, T cells pre-cultured for 72 hours on a CCL21+ICAM1 coated surface, were able to kill more target cells by 24 hours of co-culturing compared to those pre-cultured on an uncoated surface or those pre-cultured on a CCL21+ICAM1 coated surface with addition of IL-6 (FIGS. 12A-D and 12I). Interestingly, this advantage was lost at 36 hours and onward (FIG. 12I). Moreover, T cells pre-cultured for 7 days on a CCL21+ICAM1 coated surface, killed target cells more rapidly, with up to 2.5 times less live target cells by 24-72 hours of co-culturing, compared to those cultured on an uncoated surface (FIGS. 12E-G, 12J and 13A1-G3).

Despite the significant improvement in T cell survival induced by soluble IL-6 (FIGS. 11J and 11L), when added to T cells cultured on CCL21+ICAM1 for 72 hours or 7d, killing of target cells was significantly attenuated and slowed down, with up to two times more live target cells than in the uncoated group and nearly six times more than in the CCL21+ICAM without IL-6 group (FIGS. 12E-H, 12J and 13A1-G3). The more efficient killing by T-cells cultured on CCL21+ICAM1 coating could be attributed to T cells' increased expression of granzyme B which mediates the killing process (6.5-fold following 24 hours incubation with the target cells, FIG. 12K). Furthermore, T cells pre-cultured on a CCL21+ICAM1 coated surface, not only killed more target cells more rapidly (FIGS. 13C1-C5 and 13G1-G3), but formed larger clusters (which could indicate increased proliferation), compared to T cells grown on an uncoated surface (FIGS. 13B1-B5 and 13F1-F3).

Given that no surface manipulation was done in the co-cultures of T and target-cells during the killing assays, there is probably no need for continuous stimulation by CCL21+ICAM1 at the target site, for their beneficial effects of increased T cell proliferation and faster killing to persist, further supporting their use in ex-vivo manipulation for adoptive cell therapy.

In-Vitro Activation of CD8⁺ T Cells with Antigen Loaded DCs on a Coated CCL21 and ICAM1 Surface Improves the Cells In-Vivo Tumor Suppression To validate the in-vitro findings in-vivo, B 16-OVA tumor-bearing mice were injected, intravenously, with T cells activated and pre-cultured for 7-9 days activated on an uncoated surface, or on a CCL21+ICAM1 coated surface (a schematic representation of the experimental design is depicted in FIG. 14A). As shown in FIGS. 14A-D, the in-vivo results correlated with the in-vitro results (FIG. 13A1-G3). Specifically, OT-I CD8⁺ T cells cultured on both an uncoated surface or on a CCL2+ICAM1 coated surface suppressed tumor growth, in a dose dependent manner compared to non-treated group (FIGS. 14B-C). However, treatment with T cells pre-activated on a CCL21+ICAM1 coated surface suppressed tumor growth to a significantly greater extent, with an over 3-fold smaller (FIG. 14B) and 8-fold smaller (FIG. 14C) end-point tumor average volume compared to that of T cells activated on uncoated surfaces. In addition, tumors treated with T cells activated on a CCL21+ICAM1 surface, had almost no increase in tumor size throughout the follow up, while tumors treated with T cells activated on an uncoated surface continuously grew in size over time.

Example 4

CCL21 and ICAM1 During In-Vitro Production and Activation of Human CAR T Cells have a Combined Improved Effect on Cells Expantion and In-Vitro Cytotoxic Efficiency To further validate the results described above, engineered T cells expressing a chimeric antigen receptor (CAR) (for an overview on CAR T cells see Almasbak H, et al. *J Immunol Res.* 2016; 2016:5474602) were used as an additional model. In this model, the specificity of a monoclonal antibody is grafted onto autologous T cells from the patient's blood, along with a signaling domain taken from activating and co-stimulatory immune receptors. As a result, these engineered T cells could be both activated and co-stimulated through their CAR when binding a desired tumor associated antigen. Specifically, the model used was a HER2-CAR (see Globerson-Levin A et al. *Mol Ther.* 2014; 22(5):1029-1038). In this model, all T cells (comprising both CD4⁺ and CD8⁺ T cells), are isolated from a donated human blood, activated using anti-CD3 and anti-CD28 antibodies for 48 hours and then virally transduced with a chimeric receptor against the human oncogene HER2, for additional 48 hours. This CAR is composed of a single chain variable fragment (scFv) of the anti-ErbB-2 (HER2) monoclonal antibody (N29), linked to a variable fragment heavy (VH) chain through a flexible linker. In addition, it is ligated with the cytoplasmic domain of the co-stimulatory CD28 gene, followed by a signaling FcγR. Following transduction, the cells are expanded in IL-2 containing culture medium for additional 3-6 days before testing. Upon successful transduction, these engineered T cells could be both activated and co-stimulated through their CAR, when binding the HER2 oncogene. HER2, known as human epidermal growth factor receptor 2, is one of four tyrosine kinases in the ErbB family and a preferred dimerization partner of the other ErbB receptors. Its dimerization results in the auto-phosphorylation of its cytoplasmic tyrosine residues and several signaling pathways, whose dysregulation is strongly associated with a variety of cancers and poor prognosis (Iqbal N. *Mol Biol Int.* 2014; 2014:852748). Utilizing this CAR model allowed validating the results in a different organism (i.e. human vs. mouse) with a different antigen (HER2 vs. ovalbumin) and different T cells subtypes involved (mixed human CD4+ and CD8+ T cells vs. mouse CD8+ T cells only).

In the CAR model, in-vitro activation of human HER2-CAR cells on a CCL21+ICAM1 surface reduced human T cell clustering as compared to activation on an uncoated surface and induced cell spreading on the surface instead (FIGS. 15A-C). Importantly, the cells were more spread on the surface when cultured on the CCL1+ICAM1 coated surface at all stages of CARs production and expansion as compared to when cultured on a CCL1+ICAM1 coated surface only at cell expansion and not during production (FIGS. 15B-C). In addition, while there were no changes in the percentages of human T cells expressing CD8 (FIG. 15D), CD4 (FIG. 15E) or HER2-CAR (FIG. 15F); the expression level of HER2-CAR, measured by the mean fluorescent intensity of GFP, was significantly increased by 25% at day 3, when production and expansion of the cells was done on a CCL21+ICAM1 coated surface, and by 12% when only the expanstion was done on the CCL21+ICAM1 coated surface (FIG. 15G).

In addition, in accordance with the results in the murine model, immobilized CCL21+ICAM1 augmented the killing efficiency of HER2-CAR T cells (FIGS. 16A-J). Since the target cell line (RENCA-ErbB2) was of a murine origin and the T cells were of human origin, a group of T cells which were not transduced with the CAR antigen was used as a negative control to eliminate non-HER2 specific killing (grey column in FIGS. 16E-J). In addition, when the killing assay was performed 3 days following transduction of HER2-CAR, CCL21+ICAM1 shortened the killing time, with up to 5 times less live target cells in the group of HER2-CAR T cells produced and expanded on a CCL21+ICAM1 coated surface, compared to those produced and expanded on an uncoated surface (FIG. 16G). Furthermore, a smaller, yet significant increase in killing, of up to 2 times less live target cells, was seen in the group of HER2-CAR T cells produced without coating but expanded on a CCL21+ICAM1 coated surface, compared to those produced and expanded on an uncoated surface (FIG. 16G). When the killing assay was performed 6 days following transduction of HER2-CAR, production and expansion of the cells on a CCL21+ICAM1 coated surface as well as only expansion of the cells on a CCL21+ICAM1 coated surface similarly augmented the killing efficiency, with up to 2 times less target cells than in the group cultured on an uncoated surface (FIGS. 16H-J).

Taken together, an ex-vivo environment for the efficient expansion of functional CD4+ and/or CD8+ T cells was created by immobilization of the chemokine CCL21 and the adhesion molecule ICAM1 on the surface on which the cells were cultured. The results are summarized in Table 1 below in addition to results obtained by other ex-vivo environments tested by the present inventors. Both antigen-specific and non-specific activation of T cells in this environment induced a dramatic shift in the organization and morphology of the T cells, as well as greatly improved their expansion and in the case of CD8+ T cells also the in-vitro killing efficiency and in-vivo tumor suppression. Without being bound by theory, it is suggested that the strength of this combination might arise from preserving the potentially beneficial effects of intercellular interactions through LFA1-ICAM1, while avoiding the down-regulatory activity observed in the large 3D clusters. Another possible explanation for the mechanism underlying the collective effect of CCL21-ICAM1 involves the activation of LFA1, the ICAM1 receptor, by CCL21, thereby reinforcing the cells' interactions with the surface. Most importantly, the results indicate that activating T cells on a CCL21+ICAM1 coated surface increases their proliferation even several days following the end of exposure to the coating, indicating that a continuous CCL21 and ICAM1 signal at the e.g. tumor site is unnecessary.

TABLE 1

Summary of the results obtained with differed coating and soluble factors.

| Cell Type | Immobilized factor | Soluble factor | Tested effects | Findings* |
|---|---|---|---|---|
| CD4 | CCL21 | — | Cell Yield/Clustering/Cell spreading | Increases cluster number, size and cell yield |
| | ICAM1 | — | | Decreases cluster size and increases cell spreading and yield |
| | CCL21 + ICAM1 | — | | Spread cells, increased proliferation and cell yield compared to CCL21 only or ICAM1 only |
| | Fibronectin | — | Clustering/Cell spreading | No effect |
| | Poly Lysine | — | | No effect |
| | Anti-LFA1 | — | Cell Yield/Clustering/Cell spreading | Cell spreading, few clustering, low yield |
| | Anti-LFA1 + CCL21 | — | | Cell spreading, few clustering, low yield |
| | — | IL-2 | | Inconsistent changes in cell yield |
| | CCL21 + ICAM1 | | | Did not add to cell yield compared to CCL21 + ICAM1 or CCL21 + ICAM1 + IL-6 |
| | — | IL-12 | | Slightly bigger clusters |
| | CCL21 + ICAM1 | | | Did not add to cell yield compared to CCL21 + ICAM1 |
| | — | IL-6 | | Higher cell yield |
| | CCL21 + ICAM1 | | | Higher cell yield compared to CCL21 + ICAM1 |
| | — | IL-7 | | Higher cell yield |
| | CCL21 + ICAM1 | | | Did not add to cell yield compared to CCL21 + ICAM1 |
| | — | IFNg | | Higher cell yield |

TABLE 1-continued

Summary of the results obtained with differed coating and soluble factors.

| Cell Type | Immobilized factor | Soluble factor | Tested effects | Findings* |
|---|---|---|---|---|
| | CCL21 + ICAM1 | | | Did not add to cell yield compared to CCL21 + ICAM1 or CCL21 + ICAM1 + IL-6 |
| | — | TGFb | Clustering/Cell spreading | No effect |
| | — | IL-4 | | No effect |
| | — | LPS | | No effect |
| | — | TNFa | | No effect |
| | — | GM-CSF | | No effect |
| CD8 | CCL21 | — | Cell Yield/Clustering/Cell spreading | Increases cluster number, size and cell yield |
| | ICAM1 | — | Cell Yield/Clustering/Cell spreading/functional killing of target cells | Decreases cluster size and increases cell spreading and yield, inconsistent changes in killing neither alone or with IL-6 |
| | CCL21 + ICAM1 | — | | Spread cells, increased proliferation and cell yield compared to CCL21 only or ICAM1 only. Improved killing without IL-6 and impaired killing with IL-6, both compared to control of no coating or cytokines |
| | — | IL-6 | | Higher cell yield, impaired killing |
| | CCL21 + ICAM1 | | | Higher cell yield compared to CCL21 + ICAM1, but impaired killing |
| | CD40L | — | Cell Yield/Clustering/Cell spreading/ | Inconsistent slight increase in cell yield |
| | CD40L + CCL21 | | | Inconsistent slight increase in cell yield on top of CCL21 alone |
| | CD40L + ICAM1 | | | Inconsistent slight increase in cell yield on top of ICAM1 alone |
| | CD40L + CCL21 + ICAM1 | | | Inconsistent slight increase in cell yield on top of CCL21 + ICAM1 |
| | — | IL-2 | | Inconsistent changes in cell yield |
| | CCL21 + ICAM1 | | | Did not add to cell yield compared to CCL21 + ICAM1 or CCL21 + ICAM1 + IL-6 |
| | — | IL-12 | | Higher cell yield |
| | CCL21 + ICAM1 | | | Did not add to cell yield compared to CCL21 + ICAM1 or CCL21 + ICAM1 + IL-6 |
| | — | IL-7 | | Slightly higher cell yield |
| | CCL21 + ICAM1 | | | Did not add to cell yield compared to CCL21 + ICAM1 |
| | — | IFNg | | Higher cell yield |
| | CCL21 + ICAM1 | | | Did not add to cell yield compare to CCL21 + ICAM1 or CCL21 + ICAM1 + IL-6 |
| | — | IL-15 | | Inconsistent changes in cell yield |
| | CCL21 + ICAM1 | | | Did not add to cell yield compared to CCL21 + ICAM1 |
| | — | IL-2 + IL6 + IL-12 | | Higher cell yield |
| | CCL21 + ICAM1 | | | Did not add to cell yield compared to CCL21 + ICAM1 |

*Finding are presented in comparison to cell cultures of the same species under the same culture conditions without the indicated immobilized factor and/or the soluble factor, unless stated otherwise.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited Throughout the Application

1. Rosenberg S A. Progress in human tumour immunology and immunotherapy. Nature. 2001; 411(6835):380-384. Prepublished on May 18, 2001 as DOI 10.1038/35077246.
2. Weigelin B, Krause M, Friedl P. Cytotoxic T lymphocyte migration and effector function in the tumor microenvironment. Immunology letters. 2011; 138(1):19-21. Prepublished on Feb. 22, 2011 as DOI 10.1016/j.imlet.2011.02.016.
3. Gerard A, Khan O, Beemiller P, et al. Secondary T cell-T cell synaptic interactions drive the differentiation of protective CD8+ T cells. Nat Immunol. 2013; 14(4):356-363. Prepublished on Mar. 12, 2013 as DOI 10.1038/ni.2547.

4. Xie J T C, Davis M M. How the immune system talks to itself: the varied role of synapses. *Immunol Rev.* 2013; 251(1):14.
5. Adutler-Lieber S, Zaretsky I, Platzman I, et al. Engineering of synthetic cellular microenvironments: Implications for immunity. *J Autoimmun.* 2014. Prepublished on Jun. 22, 2014 as DOI 10.1016/j.jaut.2014.05.003.
6. Dudley M E, Rosenberg S A. Adoptive-cell-transfer therapy for the treatment of patients with cancer. *Nat Rev Cancer.* 2003; 3(9):666-675. Prepublished on Sep. 3, 2003 as DOI 10.1038/nrc1167.
7. Gattinoni L, Powell D J, Jr., Rosenberg S A, Restifo N P. Adoptive immunotherapy for cancer: building on success. *Nat Rev Immunol.* 2006; 6(5):383-393. Prepublished on Apr. 20, 2006 as DOI 10.1038/nri1842.
8. Tibbitt M W, Anseth K S. Hydrogels as extracellular matrix mimics for 3D cell culture. *Biotechnol Bioeng.* 2009; 103(4):655-663. Prepublished on May 28, 2009 as DOI 10.1002/bit.22361.
9. Holmes B, Castro N J, Zhang L G, Zussman E. Electrospun fibrous scaffolds for bone and cartilage tissue generation: recent progress and future developments. *Tissue Eng Part B Rev.* 2012; 18(6):478-486. Prepublished on Jun. 29, 2012 as DOI 10.1089/ten.TEB.2012.0096.
10. Hughes C S, Postovit L M, Lajoie G A. Matrigel: a complex protein mixture required for optimal growth of cell culture. *Proteomics.* 2010; 10(9):1886-1890. Prepublished on Feb. 18, 2010 as DOI 10.1002/pmic.200900758.
11. Okamoto N, Chihara R, Shimizu C, Nishimoto S, Watanabe T. Artificial lymph nodes induce potent secondary immune responses in naïve and immunodeficient mice. *J Clin Invest.* 2007; 117(4):997-1007. Prepublished on Mar. 17, 2007 as DOI 10.1172/JCI30379.
12. Mirsadraee S, Wilcox H E, Korossis S A, et al. Development and characterization of an acellular human pericardial matrix for tissue engineering. *Tissue Eng.* 2006; 12(4):763-773. Prepublished on May 6, 2006 as DOI 10.1089/ten.2006.12.763.
13. Guillotin B, Guillemot F. Cell patterning technologies for organotypic tissue fabrication. *Trends Biotechnol.* 2011; 29(4):183-190. Prepublished on Jan. 25, 2011 as DOI 10.1016/j.tibtech.2010.12.008.
14. Cupedo T, Stroock A, Coles M. Application of tissue engineering to the immune system: development of artificial lymph nodes. *Front Immunol.* 2012; 3:343. Prepublished on Nov. 20, 2012 as DOI 10.3389/fimmu.2012.00343.
15. Tan J K, Watanabe T. Artificial engineering of secondary lymphoid organs. *Adv Immunol.* 2010; 105:131-157. Prepublished on Jun. 1, 2010 as DOI 10.1016/S0065-2776 (10)05005-4.
16. Irvine D J, Stachowiak A N, Hori Y. Lymphoid tissue engineering: invoking lymphoid tissue neogenesis in immunotherapy and models of immunity. *Semin Immunol.* 2008; 20(2):137-146. Prepublished on Nov. 24, 2007 as DOI 10.1016/j.smim.2007.10.010.
17. Kobayashi Y, Kato K, Watanabe T. Synthesis of functional artificial lymphoid tissues. *Discov Med.* 2011; 12(65):351-362. Prepublished on Oct. 28, 2011 as DOI.
18. Suematsu S, Watanabe T. Generation of a synthetic lymphoid tissue-like organoid in mice. *Nat Biotechnol.* 2004; 22(12):1539-1545. Prepublished on Nov. 30, 2004 as DOI 10.1038/nbt1039.
19. Zheng Y, Chen J, Craven M, et al. In vitro microvessels for the study of angiogenesis and thrombosis. *Proc Natl Acad Sci USA.* 2012; 109(24):9342-9347. Prepublished on May 31, 2012 as DOI 10.1073/pnas.1201240109.
20. Giese C, Lubitz A, Demmler C D, Reuschel J, Bergner K, Marx U. Immunological substance testing on human lymphatic micro-organoids in vitro. *J Biotechnol.* 2010; 148(1):38-45. Prepublished on Apr. 27, 2010 as DOI 10.1016/j.jbiotec.2010.03.001.
21. Benezech C, Mader E, Desanti G, et al. Lymphotoxin-beta receptor signaling through NF-kappaB2-RelB pathway reprograms adipocyte precursors as lymph node stromal cells. *Immunity.* 2012; 37(4):721-734. Prepublished on Sep. 4, 2012 as DOI 10.1016/j.immuni.2012.06.010.
22. von Andrian U H, Mempel T R. Homing and cellular traffic in lymph nodes. *Nat Rev Immunol.* 2003; 3(11): 867-878. Prepublished on Dec. 12, 2003 as DOI 10.1038/nri1222.
23. Willard-Mack C L. Normal structure, function, and histology of lymph nodes. *Toxicol Pathol.* 2006; 34(5): 409-424. Prepublished on Oct. 28, 2006 as DOI 10.1080/01926230600867727.
24. Mueller S N, Germain R N. Stromal cell contributions to the homeostasis and functionality of the immune system. *Nat Rev Immunol.* 2009; 9(9):618-629. Prepublished on Aug. 1, 2009 as DOI 10.1038/nri2588.
25. Ruco L P, Pomponi D, Pigott R, Gearing A J, Baiocchini A, Baroni C D. Expression and cell distribution of the intercellular adhesion molecule, vascular cell adhesion molecule, endothelial leukocyte adhesion molecule, and endothelial cell adhesion molecule (CD31) in reactive human lymph nodes and in Hodgkin's disease. *Am J Pathol.* 1992; 140(6):1337-1344. Prepublished on Jun. 1, 1992 as DOI.
26. Gretz J E, Kaldjian E P, Anderson A O, Shaw S. Sophisticated strategies for information encounter in the lymph node: the reticular network as a conduit of soluble information and a highway for cell traffic. *J Immunol.* 1996; 157(2):495-499. Prepublished on Jul. 15, 1996 as DOI.
27. Kaldjian E P, Gretz J E, Anderson A O, Shi Y, Shaw S. Spatial and molecular organization of lymph node T cell cortex: a labyrinthine cavity bounded by an epithelium-like monolayer of fibroblastic reticular cells anchored to basement membrane-like extracellular matrix. *Int Immunol.* 2001; 13(10):1243-1253. Prepublished on Oct. 3, 2001 as DOI.
28. Dienz O, Rincon M. The effects of IL-6 on CD4 T cell responses. *Clin Immunol.* 2009; 130(1):27-33. Prepublished on Oct. 11, 2008 as DOI 10.1016/j.clim.2008.08.018.
29. Rochman I, Paul W E, Ben-Sasson S Z. IL-6 increases primed cell expansion and survival. *J Immunol.* 2005; 174(8):4761-4767. Prepublished on Apr. 9, 2005 as DOI.
30. Stein J V, Rot A, Luo Y, et al. The CC chemokine thymus-derived chemotactic agent 4 (TCA-4, secondary lymphoid tissue chemokine, 6Ckine, exodus-2) triggers lymphocyte function-associated antigen 1-mediated arrest of rolling T lymphocytes in peripheral lymph node high endothelial venules. *J Exp Med.* 2000; 191(1):61-76. Prepublished on Jan. 6, 2000 as DOI.
31. Sherven Sharma L Z, Minu K Srivastava, et al. CCL21 Therapy for Lung Cancer. *Internatinal Trends in Immunity.* 2013; 1(1):10-15.
32. Shields J D, Kourtis I C, Tomei A A, Roberts J M, Swartz M A. Induction of lymphoidlike stroma and immune escape by tumors that express the chemokine CCL21. *Science.* 2010; 328(5979):749-752. Prepublished on Mar. 27, 2010 as DOI 10.1126/science.1185837.

33. Yang S C, Hillinger S, Riedl K, et al. Intratumoral administration of dendritic cells overexpressing CCL21 generates systemic antitumor responses and confers tumor immunity. *Clin Cancer Res*. 2004; 10(8):2891-2901. Prepublished on Apr. 23, 2004 as DOI.
34. Gonen-Wadmany M, Oss-Ronen L, Seliktar D. Protein-polymer conjugates for forming photopolymerizable biomimetic hydrogels for tissue engineering. *Biomaterials*. 2007; 28(26):3876-3886. Prepublished on Jun. 20, 2007 as DOI 10.1016/j.biomaterials.2007.05.005.
35. Dikovsky D, Bianco-Peled H, Seliktar D. The effect of structural alterations of PEG-fibrinogen hydrogel scaffolds on 3-D cellular morphology and cellular migration. *Biomaterials*. 2006; 27(8):1496-1506. Prepublished on Oct. 26, 2005 as DOI 10.1016/j.biomaterials.2005.09.038.
36. Friedman R S, Jacobelli J, Krummel M F. Surface-bound chemokines capture and prime T cells for synapse formation. *Nat Immunol*. 2006; 7(10):1101-1108. Prepublished on Sep. 12, 2006 as DOI 10.1038/ni1384.
37. Flanagan K, Moroziewicz D, Kwak H, Horig H, Kaufman H L. The lymphoid chemokine CCL21 costimulates naïve T cell expansion and Th1 polarization of non-regulatory CD4+ T cells. *Cell Immunol*. 2004; 231(1-2):75-84. Prepublished on May 28, 2005 as DOI 10.1016/j.cellimm.2004.12.006.
38. Mitchison N A. An exact comparison between the efficiency of two- and three-cell-type clusters in mediating helper activity. *Eur J Immunol*. 1990; 20(3):699-702. Prepublished on Mar. 1, 1990 as DOI 10.1002/eji.1830200335.
39. Ingulli E, Mondino A, Khoruts A, Jenkins M K. In vivo detection of dendritic cell antigen presentation to CD4(+) T cells. *J Exp Med*. 1997; 185(12):2133-2141.
40. Schuhbauer D M, Mitchison N A, Mueller B. Interaction within clusters of dendritic cells and helper T cells during initial Th1/Th2 commitment. *Eur J Immunol*. 2000; 30(5): 1255-1262. Prepublished on May 23, 2000 as DOI 10.1002/(SICI)1521-4141(200005)30:5< 1255:: AID-IMMU1255> 3.0.CO;2-W.
41. Woolf E, Grigorova I, Sagiv A, et al. Lymph node chemokines promote sustained T lymphocyte motility without triggering stable integrin adhesiveness in the absence of shear forces. *Nat Immunol*. 2007; 8(10):1076-1085. Prepublished on Aug. 28, 2007 as DOI 10.1038/ni1499.
42. Miller M J, Safrina O, Parker I, Cahalan M D. Imaging the single cell dynamics of CD4+ T cell activation by dendritic cells in lymph nodes. *J Exp Med*. 2004; 200(7): 847-856. Prepublished on Oct. 7, 2004 as DOI 10.1084/jem.20041236.
43. Thurley K, Gerecht D, Friedmann E, Hofer T. Three-dimensional gradients of cytokine signaling between T cells. *PLoS Comput Biol*. 2015; 11(4):e1004206. Prepublished on Apr. 30, 2015 as DOI 10.1371/journal.pcbi.1004206.
44. Gerard A, Khan O, Beemiller P, et al. Secondary T cell-T cell synaptic interactions drive the differentiation of protective CD8+ T cells. *Nature Immunology*. 2013; 14(4): 356-363. Prepublished on Mar. 12, 2013 as DOI 10.1038/ni.2547.
45. Schwartz R H. A cell culture model for T lymphocyte clonal anergy. *Science*. 1990; 248(4961): 1349-1356.
46. Zumwalde N A, Domae E, Mescher M F, Shimizu Y. ICAM1-dependent homotypic aggregates regulate CD8 T cell effector function and differentiation during T cell activation. *J Immunol*. 2013; 191(7):3681-3693. Prepublished on Sep. 3, 2013 as DOI 10.4049/jimmunol.1201954.
47. Sowinski S, Jolly C, Berninghausen O, et al. Membrane nanotubes physically connect T cells over long distances presenting a novel route for HIV-1 transmission. *Nat Cell Biol*. 2008; 10(2):211-219. Prepublished on Jan. 15, 2008 as DOI 10.1038/ncb1682.

---

What is claimed is:

1. A method of culturing T cells, the method comprising culturing T cells in a culture vessel in the presence of a T cell stimulator, an exogenous CCL21 and an exogenous ICAM1, thereby culturing the T cells, wherein each of said CCL21 and ICAM1 are immobilized to a solid support, wherein said T cell stimulator is an antigen-specific stimulator comprising a dendritic cell loaded with an antigen, wherein said immobilized CCL21 and ICAM1 are attached to said culture vessel, and wherein said T cells comprise engineered T cells transduced with a nucleic acid encoding a T cell receptor (TCR) or a chimeric antigen receptor (CAR).

2. The method of claim 1, wherein said culturing is effected for 3-7 days.

3. The method of claim 1, further comprising adding a cytokine to the culture.

4. The method of claim 3, wherein said T cells comprise CD4$^+$ T cells and said cytokine is IL-6.

5. The method of claim 3, wherein said T cells comprise CD8$^+$ T cells and said cytokine is not IL-6.

6. The method of claim 1, wherein said T cells comprise CD4$^+$ T cells.

7. The method of claim 1, wherein said T cells comprise CD8$^+$ T cells.

8. A method of producing engineered T cells, the method comprising transducing T cells with a nucleic acid encoding an expression product of interest and further comprising culturing said T cells in a culture vessel in the presence of an exogenous chemokine, an exogenous adhesion molecule and a T cell stimulator, thereby producing the engineered T cells, wherein said chemokine is CCL21, and said adhesion molecule is ICAM1, and wherein each of said chemokine and adhesion molecule are immobilized to a solid support, wherein said T cell stimulator is an antigen-specific stimulator comprising a dendritic cell loaded with an antigen, wherein said immobilized CCL21 and ICAM 1 are attached to said culture vessel, and wherein said expression product of interest is a T cell receptor (TCR) or a chimeric antigen receptor (CAR).

9. The method of claim 1 or claim 8, wherein said antigen is a cancer antigen.

10. The method of claim 1 or claim 8, wherein the T cells seeding concentration in the culture is less than $5 \times 10^4$ cells/ml culture medium.

* * * * *